United States Patent
Martinez et al.

(10) Patent No.: US 11,629,118 B2
(45) Date of Patent: Apr. 18, 2023

(54) FORMULATIONS WITH IMPROVED STABILITY

(71) Applicant: INSPIRNA, INC., New York, NY (US)

(72) Inventors: Eduardo Martinez, Bryn Mawr, PA (US); Peter Rix, San Diego, CA (US); Eric Gruff, Poway, CA (US)

(73) Assignee: INSPIRNA, INC., New York, NY (US)

(*) Notice: Subject to any disclaimer, the term of this patent is extended or adjusted under 35 U.S.C. 154(b) by 0 days.

(21) Appl. No.: 15/911,062

(22) Filed: Mar. 2, 2018

(65) Prior Publication Data

US 2018/0251422 A1 Sep. 6, 2018

Related U.S. Application Data

(60) Provisional application No. 62/466,955, filed on Mar. 3, 2017.

(51) Int. Cl.

| | |
|---|---|
| *C07C 229/34* | (2006.01) |
| *A61K 31/195* | (2006.01) |
| *A61K 47/14* | (2017.01) |
| *A61K 9/107* | (2006.01) |
| *A61K 47/24* | (2006.01) |
| *A61K 47/22* | (2006.01) |
| *A61K 47/18* | (2017.01) |
| *A61K 47/10* | (2017.01) |
| *A61K 9/48* | (2006.01) |
| *A61K 47/44* | (2017.01) |
| *A61K 9/00* | (2006.01) |
| *A61P 35/00* | (2006.01) |

(52) U.S. Cl.
CPC .......... *C07C 229/34* (2013.01); *A61K 9/0053* (2013.01); *A61K 9/107* (2013.01); *A61K 9/1075* (2013.01); *A61K 9/4858* (2013.01); *A61K 31/195* (2013.01); *A61K 47/10* (2013.01); *A61K 47/14* (2013.01); *A61K 47/183* (2013.01); *A61K 47/22* (2013.01); *A61K 47/24* (2013.01); *A61K 47/44* (2013.01); *A61P 35/00* (2018.01)

(58) Field of Classification Search
CPC .... C07C 229/34; A61K 47/10; A61K 47/183; A61K 47/24; A61K 9/107; A61K 47/14; A61K 31/195; A61K 47/44
See application file for complete search history.

(56) References Cited

U.S. PATENT DOCUMENTS

| | | | |
|---|---|---|---|
| 2,680,749 A | 6/1954 | Cawley et al. | |
| 3,102,078 A | 8/1963 | Robeson | |
| 6,340,473 B1 | 1/2002 | Tanner et al. | |
| 6,582,727 B2 | 6/2003 | Tanner et al. | |
| 6,884,060 B2 | 4/2005 | Tanner et al. | |
| 7,247,748 B2 | 7/2007 | Thompson et al. | |
| 7,323,494 B2 | 1/2008 | Thompson et al. | |
| 7,365,085 B2 | 4/2008 | Bhat et al. | |
| 7,560,586 B2 | 7/2009 | Thompson et al. | |
| 8,231,896 B2 | 7/2012 | Tanner et al. | |
| 8,377,470 B2 | 2/2013 | Tanner et al. | |
| 2006/0153913 A1 | 7/2006 | Yamane et al. | |
| 2007/0141203 A1 | 6/2007 | Cook | |
| 2007/0184117 A1 | 8/2007 | Gregory et al. | |
| 2017/0066791 A1 | 3/2017 | Martinez et al. | |

FOREIGN PATENT DOCUMENTS

| | | |
|---|---|---|
| JP | 2015-532642 A | 11/2015 |
| WO | 03/082802 A1 | 10/2003 |
| WO | 2014/028461 A2 | 2/2014 |
| WO | 2015/106164 A1 | 7/2015 |

OTHER PUBLICATIONS

Kalepu, "Oral lipid-based drug delivery systems—an overview", Acta Pharmaceutica Sinica B, 2013;3(6):361-372.*
Collins et al., "Identification of a Nonsteroidal Liver X Receptor Agonist Through Parallel Array Synthesis of Tertiary Amines" J. Med. Chem., Apr. 2002, 45:1963-1966.
Childs et al., "The Salt-Cocrystal Continuum: The Influence of Crystal Structure on Ionization State" Mol. Pharmaceutics, Apr. 2007, 4(3):323-338.
International Search Report and Written Opinion in International Application No. PCT/US2018/020797, dated May 16, 2018 (10 pages).
Examination Report issued in counterpart European Application No. 18712347.6, dated Oct. 30, 2020 (6 pages).
First Office Action in Chinese Application No. 201880021207.3 (dated May 2022).
Vincent Jannin, "Lauroyl Polyoxylglycerides, Functionalized Coconut Oil, Enhancing the Bioavailability of Poorly Soluble Active Substances," 16(4) OCL 267-272 (Jul.-Dec. 2009).
Official Action in Mexican Application No. MX/a/2019/010330 (dated Sep. 2021).
Official Action in Mexican Application No. MX/a/2019/010330 (dated Feb. 2022).
Notification of Reasons for Refusal in Japanese Patent Application No. 2019-569659 (dated Nov. 2021).
Notice of Reasons for Refusal in Japanese Application No. 2019-569659 (dated Jul. 2022).
Decision of Refusal in Japanese Application No. 2019-569659 (dated Nov. 2022).
Second Office Action in Chinese Application No. 201880021207.3 (dated Dec. 2022).

* cited by examiner

*Primary Examiner* — Sahar Javanmard
(74) *Attorney, Agent, or Firm* — Venable LLP

(57) ABSTRACT

Formulations containing pharmaceutically active compounds with improved stability.

20 Claims, No Drawings

FORMULATIONS WITH IMPROVED STABILITY

CROSS-REFERENCE TO RELATED APPLICATION

This application claims the benefit of Provisional Application No. 62/466,955, filed Mar. 3, 2017, which is incorporated herein by reference in its entirety.

FIELD OF THE INVENTION

This invention relates to formulations with improved stability.

BACKGROUND OF THE INVENTION

The Liver X Receptor (LXR) is a nuclear receptor transcription factor. It has been found that LXR modulators are useful in the treatment of a variety of diseases, including cancers. There is a need to provide formulations of such compounds with improved stability.

SUMMARY OF THE INVENTION

One aspect of this invention pertains to a pharmaceutically acceptable salt of formula I:

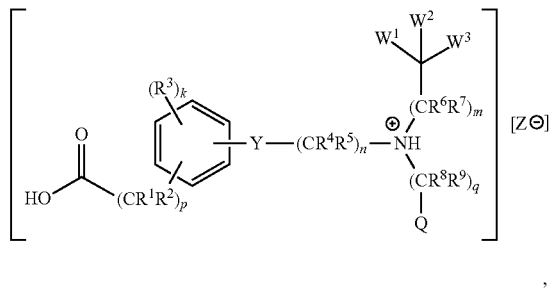

wherein:

$Z^{\ominus}$ is a fatty acid carboxylate;

Y is selected from —O—, —S—, —N($R^{12}$)—, and —C($R^4$)($R^5$)—;

$W^1$ is selected from $C_1$-$C_6$ alkyl, $C_0$-$C_6$ alkyl, $C_3$-$C_6$ cycloalkyl, aryl and Het, wherein said $C_1$-$C_8$ alkyl, $C_3$-$C_8$ cycloalkyl, Ar and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl-$CO_2R^{12}$, —$C_0$-$C_6$ alkyl-C(O)$SR^{12}$, —$C_0$-$C_6$ alkyl-$CONR^{13}R^{14}$, —$C_0$-$C_6$ alkyl-$COR^{15}$, —$C_0$-$C_6$ alkyl-$NR^{13}R^{14}$, —$C_0$-$C_6$ alkyl-$SR^{12}$, —$C_0$-$C_6$ alkyl-$OR^{12}$, —$C_0$-$C_6$ alkyl-$SO_3H$, —$C_0$-$C_6$ alkyl-$SO_2NR^{13}R^{14}$, —$C_0$-$C_6$ alkyl-$SO_2R^{12}$, —$C_0$-$C_6$ alkyl-$SOR^{15}$, —$C_0$-$C_6$ alkylO$COR^{15}$, —$C_0$-$C_6$ alkyl-OC(O)$NR^{13}R^{14}$, —$C_0$-$C_6$ alkyl-OC(O)$OR^{15}$, —$C_0$-$C_6$ alkyl-$NR^{13}$C(O)$OR^{15}$, —$C_0$-$C_6$ alkyl-$NR^{13}$C(O)$NR^{13}R^{14}$, and —$C_0$-$C_6$ alkyl-$NR^{13}COR^{15}$, where said $C_1$-$C_6$ alkyl, is optionally unsubstituted or substituted by one or more halo substituents;

$W^2$ is selected from H, halo, $C_1$-$C_6$ alkyl, $C_2$-$C_6$ alkenyl, $C_2$-$C_6$ alkynyl, —$C_0$-$C_6$ alkyl-$NR^{13}R^{14}$, —$C_0$-$C_6$ alkyl-$SR^{12}$, —$C_0$-$C_6$ alkyl-$OR^{12}$, —$C_0$-$C_6$ alkyl$CO_2R^{12}$, —$C_0$-$C_6$ alkyl-C(O)$SR^{12}$, —$C_0$-$C_6$ alkyl$CONR^{13}R^{14}$, —$C_0$-$C_6$ alkyl-$COR^{15}$, —$C_0$-$C_6$ alkylO$COR^{15}$, —$C_0$-$C_6$ alkyl-OCON$R^{13}R^{14}$, —$C_0$-$C_6$ alkyl-$NR^{13}$CON$R^{13}R^{14}$, —$C_0$-$C_6$ alkyl-$NR^{13}COR^{15}$, —$C_0$-$C_6$ alkyl-Het, —$C_0$-$C_6$ alkyl-Ar, and —$C_0$-$C_6$ alkyl-$C_3$-$C_7$ cycloalkyl, wherein said $C_1$-$C_6$ alkyl is optionally unsubstituted or substituted by one or more halo substituents, and wherein the $C_3$-$C_7$ cycloalkyl, Ar and Het moieties of said —$C_0$-$C_6$ alkyl-Het, —$C_0$-$C_6$ alkyl-Ar and —$C_0$-$C_6$ alkyl-$C_3$-$C_7$ cycloalkyl are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl-$CO_2R^{12}$, —$C_0$-$C_6$ alkyl-C(O)$SR^{12}$, —$C_0$-$C_6$ alkyl-$CONR^{13}R^{14}$, —$C_0$-$C_6$ alkyl-$COR^{15}$, —$C_0$-$C_6$ alkyl-$NR^{13}R^{14}$, —$C_0$-$C_6$ alkyl-$SR^{12}$, —$C_0$-$C_6$ alkyl-$OR^{12}$, —$C_0$-$C_6$ alkyl-$SO_3H$, —$C_0$-$C_6$ alkyl-$SO_2NR^{13}R^{14}$, —$C_0$-$C_6$ alkyl-$SO_2R^{12}$, —$C_0$-$C_6$ alkyl-$SOR^{15}$, —$C_0$-$C_6$ alkyl-$OCOR^{15}$, —$C_0$-$C_6$ alkyl-OC(O)$NR^{13}R^{14}$, —$C_0$-$C_6$ alkyl-OC(O)$OR^{15}$, —$C_0$-$C_6$ alkyl-$NR^{13}$C(O)$OR^{15}$, —$C_0$-$C_6$ alkyl-$NR^{13}$C(O)$NR^{13}R^{14}$, and —$C_0$-$C_6$ alkyl-$NR^{13}COR^{15}$, where said $C_1$-$C_6$ alkyl, is optionally unsubstituted or substituted by one or more halo substituents;

$W^3$ is selected from the group consisting of: H, halo, $C_1$-$C_6$ alkyl, —$C_0$-$C_6$ alkyl-$NR^{13}R^{14}$, —$C_0$-$C_6$ alkyl$SR^{12}$, —$C_0$-$C_6$ alkyl-$OR^{12}$, —$C_0$-$C_6$ alkyl-$CO_2R^{12}$, —$C_0$-$C_6$ alkyl-C(O)$SR^{12}$, —$C_0$-$C_6$ alkyl-$CONR^{13}R^{14}$, —$C_0$-$C_6$ alkyl-$COR^{15}$, —$C_0$-$C_6$ alkyl-$OCOR^{15}$, —$C_0$-$C_6$ alkyl-OCON$R^{13}R^{14}$, —$C_0$-$C_6$ alkylN$R^{13}$CON$R^{13}R^{14}$, —$C_0$-$C_6$ alkyl-$NR^{13}COR^{15}$, —$C_0$-$C_6$ alkyl-Het, —$C_1$-$C_6$ alkyl-Ar and —$C_1$-$C_6$ alkyl-$C_3$-$C_7$ cycloalkyl, wherein said $C_1$-$C_6$ alkyl is optionally unsubstituted or substituted by one or more halo substituents;

Q is selected from $C_3$-$C_8$ cycloalkyl, Ar, and Het; wherein said $C_3$-$C_8$ cycloalkyl, Ar, and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl$CO_2R^{12}$, —$C_0$-$C_6$ alkyl-C(O)$SR^{12}$, —$C_0$-$C_6$ alkyl$CONR^{13}R^{14}$, —$C_0$-$C_6$ alkyl-$COR^{15}$, —$C_0$-$C_6$ alkylN$R^{13}R^{14}$, —$C_0$-$C_6$ alkyl-$SR^{12}$, —$C_0$-$C_6$ alkyl-$OR^{12}$, —$C_0$-$C_6$ alkyl-$SO_3H$, —$C_0$-$C_6$ alkyl-$SO_2NR^{13}R^{14}$, —$C_0$-$C_6$ alkyl-$SO_2R^{12}$, —$C_0$-$C_6$ alkyl-$SOR^{15}$, —$C_0$-$C_6$ alkyl-$OCOR^{15}$, —$C_0$-$C_6$ alkyl-OC(O)$NR^{13}R^{14}$, —$C_0$-$C_6$ alkyl-OC(O)$OR^{15}$, —$C_0$-$C_6$ alkylN$R^{13}$C(O)$OR^{15}$, —$C_0$-$C_6$ alkyl-$NR^{13}$C(O)$NR^{13}R^{14}$, and —$C_0$-$C_6$ alkyl-$NR^{13}COR^{15}$, where said $C_1$-$C_6$ alkyl is optionally unsubstituted or substituted by one or more halo substituents;

p is 0-8;

n is 2-8;

m is 0 or 1;

q is 0 or 1;

each $R^1$ and $R^2$ are independently selected from H, halo, $C_1$-$C_6$ alkyl, $C_3$-$C_6$ alkenyl, $C_3$-$C_6$ alkynyl, —$C_0$-$C_6$ alkyl-$NR^{13}R^{14}$, —$C_0$-$C_6$ alkyl-$OR^{12}$, —$C_0$-$C_6$ alkyl-$SR^{12}$, —$C_1$-$C_6$ alkyl-Het, —$C_1$-$C_6$ alkyl-Ar, and —$C_1$-$C_6$ alkyl-$C_3$-$C_7$ cycloalkyl, or $R^1$ and $R^2$ together with the carbon to which they are attached form a 3-5 membered carbocyclic or heterocyclic ring, wherein said heterocyclic ring contains one, or more heteroatoms selected from N, O, and S, where any of said $C_1$-$C_6$ alkyl is optionally unsubstituted or substituted by one or more halo substituents;

each $R^3$ is the same or different and is independently selected from halo, cyano, nitro, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het, —$C_0$-$C_6$ alkyl-$C_3$-$C_7$ cycloalkyl, —$C_0$-$C_6$ alkyl-$CO_2R^{12}$, —$C_0$-$C_6$ alkyl-C(O)$SR^{12}$, —$C_0$-$C_6$ alkyl-$CONR^{13}R^{14}$, —$C_0$-$C_6$ alkyl-$COR^{15}$, —$C_0$-$C_6$ alkyl-$NR^{13}R^{14}$, —$C_0$-$C_6$ alkyl-$SR^{12}$, —$C_0$-$C_6$ alkyl-$OR^{12}$, —$C_0$-$C_6$ alkyl-$SO_3H$, —$C_0$-$C_6$ alkyl$SO_2NR^{13}R^{14}$, —$C_0$-$C_6$ alkyl-$SO_2R^{12}$, —$C_0$-$C_6$ alkyl-$SOR^{15}$, —$C_0$-$C_6$ alkyl-$OCOR^{15}$, —$C_0$-$C_6$ alkyl-OC(O)

$NR^{13}R^{14}$, —$C_0$-$C_6$ alkyl-OC(O)OR$^{15}$, —$C_0$-$C_6$ alkyl-NR$^{13}$C(O)OR$^{15}$, —$C_0$-$C_6$ alkyl-NR$^{13}$C(O)NR$^{13}R^{14}$, and —$C_0$-$C_6$ alkyl-NR$^{13}$COR$^{15}$, wherein said $C_1$-$C_6$ alkyl is optionally unsubstituted or substituted by one or more halo substituents;

each $R^4$ and $R^5$ is independently selected from H, halo, $C_1$-$C_6$ alkyl, —$C_0$-$C_6$ alkyl-Het, —$C_0$-$C_6$ alkyl-Ar, and —$C_0$-$C_6$ alkyl-$C_3$-$C_7$ cycloalkyl; $R^6$ and $R^7$ are each independently selected from H, halo, $C_1$-$C_6$ alkyl, —$C_0$-$C_6$ alkyl-Het, —$C_0$-$C_6$ alkyl-Ar and —$C_0$-$C_6$ alkyl-$C_3$-$C_7$ cycloalkyl;

$R^8$ and $R^9$ are each independently selected from H, halo, $C_1$-$C_6$ alkyl, —$C_0$-$C_6$ alkyl-Het, —$C_0$-$C_6$ alkyl-Ar and —$C_0$-$C_6$ alkyl-$C_3$-$C_7$ cycloalkyl;

$R^{10}$ and $R^{11}$ are each independently selected from H, $C_1$-$C_{12}$ alkyl, $C_3$-$C_{12}$ alkenyl, $C_3$-$C_{12}$ alkynyl, —$C_0$-$C_8$ alkyl-Ar, —$C_0$-$C_8$ alkyl-Het, —$C_0$-$C_8$ alkyl-$C_3$-$C_7$ cycloalkyl, —$C_0$-$C_8$ alkyl-O—Ar, —$C_0$-$C_8$ alkyl-O-Het, —$C_0$-$C_8$ alkyl-O—$C_3$-$C_7$ cycloalkyl, —$C_0$-$C_8$ alkyl-S(OX)—$C_0$-$C_8$ alkyl, —$C_0$-$C_8$ alkyl-S(O)$_x$—Ar, —$C_0$-$C_8$ alkyl-S(O)$_x$-Het, —$C_0$-$C_8$ alkyl-S(O)$_x$—$C_3$-$C_7$ cycloalkyl, —$C_0$-$C_8$ alkyl-NH—Ar, —$C_0$-$C_8$ alkyl-NH-Het, —$C_0$-$C_8$ alkyl-NH—$C_3$-$C_7$ cycloalkyl, —$C_0$-$C_8$ alkyl-N($C_1$-$C_4$ alkyl)-Ar, —$C_0$-$C_8$ alkyl-N($C_1$-$C_4$ alkyl)-Het, —$C_0$-$C_8$ alkyl-N($C_1$-$C_4$ alkyl-$C_3$-$C_7$ cycloalkyl, —$C_0$-$C_8$ alkyl-Ar, —$C_0$-$C_8$ alkyl-Het, and —$C_0$-$C_8$ alkyl-$C_3$-$C_7$ cycloalkyl, where x is 0, 1, or 2, or $R^{10}$ and $R^{11}$, together with the nitrogen to which they are attached, form a 4-7 membered heterocyclic ring which optionally contains one or more additional heteroatoms selected from N, O, and S, wherein said $C_1$-$C_{12}$ alkyl, $C_3$-$C_{12}$ alkenyl, or $C_3$-$C_{12}$ alkynyl is optionally substituted by one or more of the substituents independently selected from the group halo, —OH, —SH, —NH$_2$, —NH(unsubstituted $C_1$-$C_6$ alkyl), —N(unsubstituted $C_1$-$C_6$ alkyl)(unsubstituted $C_1$-$C_6$ alkyl), unsubstituted —O$C_1$-$C_6$ alkyl, —CO$_2$H, —CO$_2$(unsubstituted $C_1$-$C_6$ alkyl), —CONH$_2$, —CONH(unsubstituted $C_1$-$C_6$ alkyl), —CON(unsubstituted $C_1$-$C_6$ alkyl)(unsubstituted $C_1$-$C_6$ alkyl), —SO$_3$H, —SO$_2$NH$_2$, —SO$_2$NH(unsubstituted $C_1$-$C_6$ alkyl) and —SO$_2$N(unsubstituted $C_1$-$C_6$ alkyl)(unsubstituted $C_1$-$C_6$ alkyl);

$R^{12}$ is selected from H, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het and —$C_0$-$C_6$ alkyl-$C_3$-$C_7$ cycloalkyl;

each $R^{13}$ and each $R^{14}$ are independently selected from H, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het, and —$C_0$-$C_6$ alkyl-$C_3$-$C_7$ cycloalkyl, or $R^{13}$ and $R^{14}$ together with the nitrogen to which they are attached form a 4-7 membered heterocyclic ring which optionally contains one or more additional heteroatoms selected from N, O, and S; and $R^{15}$ is selected from $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het, and —$C_0$-$C_6$ alkyl-$C_3$-$C_7$ cycloalkyl.

Another aspect of this invention pertains to a formulation comprising a compound of formula II:

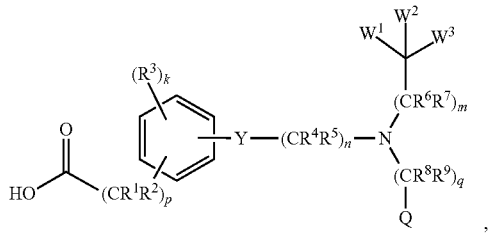

II or a pharmaceutically acceptable salt thereof, wherein:

Y is selected from —O—, —S—, —N($R^{12}$)—, and —C($R^4$)($R^5$)—;

$W^1$ is selected from $C_1$-$C_6$ alkyl, $C_0$-$C_6$ alkyl, $C_3$-$C_6$ cycloalkyl, aryl and Het, wherein said $C_1$-$C_8$ alkyl, $C_3$-$C_8$ cycloalkyl, Ar and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl-CO$_2$R$^{12}$, —$C_0$-$C_6$ alkyl-C(O)SR$^{12}$, —$C_0$-$C_6$ alkyl-CONR$^{13}R^{14}$, —$C_0$-$C_6$ alkyl-COR$^{15}$, —$C_0$-$C_6$ alkyl-NR$^{13}R^{14}$, —$C_0$-$C_6$ alkyl-SR$^{12}$, —$C_0$-$C_6$ alkyl-OR$^{12}$, —$C_0$-$C_6$ alkyl-SO$_3$H, —$C_0$-$C_6$ alkyl-SO$_2$NR$^{13}R^{14}$, —$C_0$-$C_6$ alkyl-SO$_2$R$^{12}$, —$C_0$-$C_6$ alkyl-SOR$^{15}$, —$C_0$-$C_6$ alkylOCOR$^{15}$, —$C_0$-$C_6$ alkyl-OC(O)NR$^{13}R^{14}$, —$C_0$-$C_6$ alkyl-OC(O)OR$^{15}$, —$C_0$-$C_6$ alkyl-NR$^{13}$C(O)OR$^{15}$, —$C_0$-$C_6$ alkyl-NR$^{13}$C(O)NR$^{13}R^{14}$, and —$C_0$-$C_6$ alkyl-NR$^{13}$COR$^{15}$, where said $C_1$-$C_6$ alkyl, is optionally unsubstituted or substituted by one or more halo substituents;

$W^2$ is selected from H, halo, $C_1$-$C_6$ alkyl, $C_2$-$C_6$ alkenyl, $C_2$-$C_6$ alkynyl, —$C_0$-$C_6$ alkyl-NR$^{13}R^{14}$, —$C_0$-$C_6$ alkyl-SR$^{12}$, —$C_0$-$C_6$ alkyl-OR$^{12}$, —$C_0$-$C_6$ alkylCO$_2$R$^{12}$, —$C_0$-$C_6$ alkyl-C(O)SR$^{12}$, —$C_0$-$C_6$ alkylCONR$^{13}R^{14}$, —$C_0$-$C_6$ alkyl-COR$^{15}$, —$C_0$-$C_6$ alkylOCOR$^{15}$, —$C_0$-$C_6$ alkyl-OCONR$^{13}R^{14}$, —$C_0$-$C_6$ alkyl-NR$^{13}$CONR$^{13}R^{14}$, —$C_0$-$C_6$ alkyl-NR$^{13}$COR$^{15}$, —$C_0$-$C_6$ alkyl-Het, —$C_0$-$C_6$ alkyl-Ar, and —$C_0$-$C_6$ alkyl-$C_3$-$C_7$ cycloalkyl, wherein said $C_1$-$C_6$ alkyl is optionally unsubstituted or substituted by one or more halo substituents, and wherein the $C_3$-$C_7$ cycloalkyl, Ar and Het moieties of said —$C_0$-$C_6$ alkyl-Het, —$C_0$-$C_6$ alkyl-Ar and —$C_0$-$C_6$ alkyl-$C_3$-$C_7$ cycloalkyl are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl-CO$_2$R$^{12}$, —$C_0$-$C_6$ alkyl-C(O)SR$^{12}$, —$C_0$-$C_6$ alkyl-CONR$^{13}R^{14}$, —$C_0$-$C_6$ alkyl-COR$^{15}$, —$C_0$-$C_6$ alkyl-NR$^{13}R^{14}$, —$C_0$-$C_6$ alkyl-SR$^{12}$, —$C_0$-$C_6$ alkyl-OR$^{12}$, —$C_0$-$C_6$ alkyl-SO$_3$H, —$C_0$-$C_6$ alkyl-SO$_2$NR$^{13}R^{14}$, —$C_0$-$C_6$ alkyl-SO$_2$R$^{12}$, —$C_0$-$C_6$ alkyl-SOR$^{15}$, —$C_0$-$C_6$ alkyl-OCOR$^{15}$, —$C_0$-$C_6$ alkyl-OC(O)NR$^{13}R^{14}$, —$C_0$-$C_6$ alkyl-OC(O)OR$^{15}$, —$C_0$-$C_6$ alkyl-NR$^{13}$C(O)OR$^{15}$, —$C_0$-$C_6$ alkyl-NR$^{13}$C(O)NR$^{13}R^{14}$, and —$C_0$-$C_6$ alkyl-NR$^{13}$COR$^{15}$, where said $C_1$-$C_6$ alkyl, is optionally unsubstituted or substituted by one or more halo substituents;

$W^3$ is selected from the group consisting of: H, halo, $C_1$-$C_6$ alkyl, —$C_0$-$C_6$ alkyl-NR$^{13}R^{14}$, —$C_0$-$C_6$ alkylSR$^{12}$, —$C_0$-$C_6$ alkyl-OR$^{12}$, —$C_0$-$C_6$ alkyl-CO$_2$R$^{12}$, —$C_0$-$C_6$ alkyl-C(O)SR$^{12}$, —$C_0$-$C_6$ alkyl-CONR$^{13}R^{14}$, —$C_0$-$C_6$ alkyl-COR$^{15}$, —$C_0$-$C_6$ alkyl-OCOR$^{15}$, —$C_0$-$C_6$ alkyl-OCONR$^{13}R^{14}$, —$C_0$-$C_6$ alkylNR$^{13}$CONR$^{13}R^{14}$, —$C_0$-$C_6$ alkyl-NR$^{13}$COR$^{15}$, —$C_0$-$C_6$ alkyl-Het, —$C_1$-$C_6$ alkyl-Ar and —$C_1$-$C_6$ alkyl-$C_3$-$C_7$ cycloalkyl, wherein said $C_1$-$C_6$ alkyl is optionally unsubstituted or substituted by one or more halo substituents;

Q is selected from $C_3$-$C_8$ cycloalkyl, Ar, and Het; wherein said $C_3$-$C_8$ cycloalkyl, Ar, and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkylCO$_2$R$^{12}$, —$C_0$-$C_6$ alkyl-C(O)SR$^{12}$, —$C_0$-$C_6$ alkylCONR$^{13}R^{14}$, —$C_0$-$C_6$ alkyl-COR$^{15}$, —$C_0$-$C_6$ alkylNR$^{13}R^{14}$, —$C_0$-$C_6$ alkyl-SR$^{12}$, —$C_0$-$C_6$ alkyl-OR$^{12}$, —$C_0$-$C_6$ alkyl-SO$_3$H, —$C_0$-$C_6$ alkyl-SO$_2$NR$^{13}R^{14}$, —$C_0$-$C_6$ alkyl-SO$_2$R$^{12}$, —$C_0$-$C_6$ alkyl-SOR$^{15}$, —$C_0$-$C_6$ alkyl-OCOR$^{15}$, —$C_0$-$C_6$ alkyl-OC(O)NR$^{13}R^{14}$, —$C_0$-$C_6$ alkyl-OC(O)OR$^{15}$, —$C_0$-$C_6$ alkylNR$^{13}$C(O)OR$^{15}$, —$C_0$-$C_6$ alkyl-NR$^{13}$C(O)NR$^{13}R^{14}$, and —$C_0$-$C_6$ alkyl-NR$^{13}$COR$^{15}$, where said $C_1$-$C_6$ alkyl is optionally unsubstituted or substituted by one or more halo substituents;
p is 0-8;
n is 2-8;
m is 0 or 1;
q is 0 or 1;
each $R^1$ and $R^2$ are independently selected from H, halo, $C_1$-$C_6$ alkyl, $C_3$-$C_6$ alkenyl, $C_3$-$C_6$ alkynyl, —$C_0$-$C_6$ alkyl-$NR^{13}R^{14}$, —$C_0$-$C_6$ alkyl-$OR^{12}$, —$C_0$-$C_6$ alkyl-$SR^{12}$, —$C_1$-$C_6$ alkyl-Het, —$C_1$-$C_6$ alkyl-Ar, and —$C_1$-$C_6$ alkyl-$C_3$-$C_7$ cycloalkyl, or $R^1$ and $R^2$ together with the carbon to which they are attached form a 3-5 membered carbocyclic or heterocyclic ring, wherein said heterocyclic ring contains one, or more heteroatoms selected from N, O, and S, where any of said $C_1$-$C_6$ alkyl is optionally unsubstituted or substituted by one or more halo substituents; each $R^3$ is the same or different and is independently selected from halo, cyano, nitro, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het, —$C_0$-$C_6$ alkyl-$C_3$-$C_7$ cycloalkyl, —$C_0$-$C_6$ alkyl-$CO_2R^{12}$, —$C_0$-$C_6$ alkyl-$C(O)SR^{12}$, —$C_0$-$C_6$ alkyl-$CONR^{13}R^{14}$, —$C_0$-$C_6$ alkyl-$COR^{15}$, —$C_0$-$C_6$ alkyl-$NR^{13}R^{14}$, —$C_0$-$C_6$ alkyl-$SR^{12}$, —$C_0$-$C_6$ alkyl-$OR^{12}$, —$C_0$-$C_6$ alkyl-$SO_3H$, —$C_0$-$C_6$ alkyl$SO_2NR^{13}R^{14}$, —$C_0$-$C_6$ alkyl-$SO_2R^{12}$, —$C_0$-$C_6$ alkyl$SOR^{15}$, —$C_0$-$C_6$ alkyl-$OCOR^{15}$, —$C_0$-$C_6$ alkyl-$OC(O)NR^{13}R^{14}$, —$C_0$-$C_6$ alkyl-$OC(O)OR^{15}$, —$C_0$-$C_6$ alkyl-$NR^{13}C(O)OR^{15}$, —$C_0$-$C_6$ alkyl-$NR^{13}C(O)NR^{13}R^{14}$, and —$C_0$-$C_6$ alkyl-$NR^{13}COR^{15}$, wherein said $C_1$-$C_6$ alkyl is optionally unsubstituted or substituted by one or more halo substituents;
each $R^4$ and $R^5$ is independently selected from H, halo, $C_1$-$C_6$ alkyl, —$C_0$-$C_6$ alkyl-Het, —$C_0$-$C_6$ alkyl-Ar, and —$C_0$-$C_6$ alkyl-$C_3$-$C_7$ cycloalkyl; $R^6$ and $R^7$ are each independently selected from H, halo, $C_1$-$C_6$ alkyl, —$C_0$-$C_6$ alkyl-Het, —$C_0$-$C_6$ alkyl-Ar and —$C_0$-$C_6$ alkyl-$C_3$-$C_7$ cycloalkyl;
$R^8$ and $R^9$ are each independently selected from H, halo, $C_1$-$C_6$ alkyl, —$C_0$-$C_6$ alkyl-Het, —$C_0$-$C_6$ alkyl-Ar and —$C_0$-$C_6$ alkyl-$C_3$-$C_7$ cycloalkyl;
$R^{10}$ and $R^{11}$ are each independently selected from H, $C_1$-$C_{12}$ alkyl, $C_3$-$C_{12}$ alkenyl, $C_3$-$C_{12}$ alkynyl, —$C_0$-$C_8$ alkyl-Ar, —$C_0$-$C_8$ alkyl-Het, —$C_0$-$C_8$ alkyl-$C_3$-$C_7$ cycloalkyl, —$C_0$-$C_8$ alkyl-O—Ar, —$C_0$-$C_8$ alkyl-O-Het, —$C_0$-$C_8$ alkyl-O—$C_3$-$C_7$ cycloalkyl, —$C_0$-$C_8$ alkyl-$S(O)_x$—$C_0$-$C_8$ alkyl, —$C_0$-$C_8$ alkyl-$S(O)_x$—Ar, —$C_0$-$C_8$ alkyl-$S(O)_x$-Het, —$C_0$-$C_8$ alkyl-$S(O)_x$—$C_3$-$C_7$ cycloalkyl, —$C_0$-$C_8$ alkyl-NH—Ar, —$C_0$-$C_8$ alkyl-NH-Het, —$C_0$-$C_8$ alkyl-NH—$C_3$-$C_7$ cycloalkyl, —$C_0$-$C_8$ alkyl-N($C_1$-$C_4$ alkyl)-Ar, —$C_0$-$C_8$ alkyl-N($C_1$-$C_4$ alkyl)-Het, —$C_0$-$C_8$ alkyl-N($C_1$-$C_4$ alkyl-$C_3$-$C_7$ cycloalkyl, —$C_0$-$C_8$ alkyl-Ar, —$C_0$-$C_8$ alkyl-Het, and —$C_0$-$C_8$ alkyl-$C_3$-$C_7$ cycloalkyl, where x is 0, 1, or 2, or $R^{10}$ and $R^{11}$, together with the nitrogen to which they are attached, form a 4-7 membered heterocyclic ring which optionally contains one or more additional heteroatoms selected from N, O, and S, wherein said $C_1$-$C_{12}$ alkyl, $C_3$-$C_{12}$ alkenyl, or $C_3$-$C_{12}$ alkynyl is optionally substituted by one or more of the substituents independently selected from the group halo, —OH, —SH, —$NH_2$, —NH(unsubstituted $C_1$-$C_6$ alkyl), —N(unsubstituted $C_1$-$C_6$ alkyl)(unsubstituted $C_1$-$C_6$ alkyl), unsubstituted —$OC_1$-$C_6$ alkyl, —$CO_2H$, —$CO_2$(unsubstituted $C_1$-$C_6$ alkyl), —$CONH_2$, —CONH(unsubstituted $C_1$-$C_6$ alkyl), —CON(unsubstituted $C_1$-$C_6$ alkyl)(unsubstituted $C_1$-$C_6$ alkyl), —$SO_3H$, —$SO_2NH_2$, —$SO_2NH$(unsubstituted $C_1$-$C_6$ alkyl) and —$SO_2N$(unsubstituted $C_1$-$C_6$ alkyl)(unsubstituted $C_1$-$C_6$ alkyl);

$R^{12}$ is selected from H, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het and —$C_0$-$C_6$ alkyl-$C_3$-$C_7$ cycloalkyl;
each $R^{13}$ and each $R^{14}$ are independently selected from H, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het, and —$C_0$-$C_6$ alkyl-$C_3$-$C_7$ cycloalkyl, or $R^{13}$ and $R^{14}$ together with the nitrogen to which they are attached form a 4-7 membered heterocyclic ring which optionally contains one or more additional heteroatoms selected from N, O, and S; and
$R^{15}$ is selected from $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het, and —$C_0$-$C_6$ alkyl-$C_3$-$C_7$ cycloalkyl and a lipophilic vehicle, comprising at least one lipophilic excipient, in which the compound of the formula II, or the pharmaceutically acceptable salt thereof, is soluble; wherein a pH of the formulation is from about pH 4 to about pH 8.

In an aspect of the invention, the invention features a pharmaceutically acceptable salt of formula I:

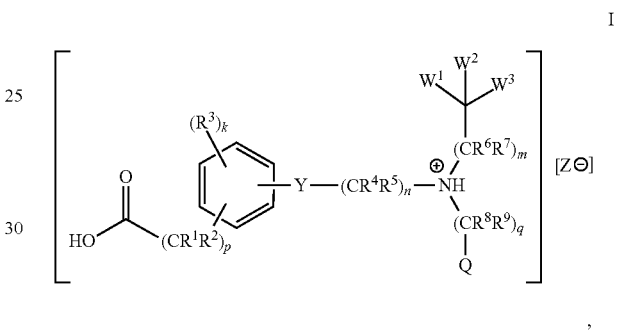

I wherein:
$Z^{\ominus}$ is a fatty acid carboxylate;
Y is selected from —O—, —S—, —$N(R^{12})$—, and —$C(R^4)(R^5)$—;
$W^1$ is selected from $C_1$-$C_6$ alkyl, $C_0$-$C_6$ alkyl, $C_3$-$C_6$ cycloalkyl, aryl and Het, wherein said $C_1$-$C_8$ alkyl, $C_3$-$C_8$ cycloalkyl, Ar and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl-$CO_2R^{12}$, —$C_0$-$C_6$ alkyl-$C(O)SR^{12}$, —$C_0$-$C_6$ alkyl-$CONR^{13}R^{14}$, —$C_0$-$C_6$ alkyl-$COR^{15}$, —$C_0$-$C_6$ alkyl-$NR^{13}R^{14}$, —$C_0$-$C_6$ alkyl-$SR^{12}$, —$C_0$-$C_6$ alkyl-$OR^{12}$, —$C_0$-$C_6$ alkyl-$SO_3H$, —$C_0$-$C_6$ alkyl-$SO_2NR^{13}R^{14}$, —$C_0$-$C_6$ alkyl-$SO_2R^{12}$, —$C_0$-$C_6$ alkyl-$SOR^{15}$, —$C_0$-$C_6$ alkyl$OCOR^{15}$, —$C_0$-$C_6$ alkyl-$OC(O)NR^{13}R^{14}$, —$C_0$-$C_6$ alkyl-$OC(O)OR^{15}$, —$C_0$-$C_6$ alkyl-$NR^{13}C(O)OR^{15}$, —$C_0$-$C_6$ alkyl-$NR^{13}C(O)NR^{13}R^{14}$, and —$C_0$-$C_6$ alkyl-$NR^{13}COR^{15}$, where said $C_1$-$C_6$ alkyl, is optionally unsubstituted or substituted by one or more halo substituents;
$W^2$ is selected from H, halo, $C_1$-$C_6$ alkyl, $C_2$-$C_6$ alkenyl, $C_2$-$C_6$ alkynyl, —$C_0$-$C_6$ alkyl-$NR^{13}R^{14}$, —$C_0$-$C_6$ alkyl-$SR^{12}$, —$C_0$-$C_6$ alkyl-$OR^{12}$, —$C_0$-$C_6$ alkyl$CO_2R^{12}$, —$C_0$-$C_6$ alkyl-$C(O)SR^{12}$, —$C_0$-$C_6$ alkyl$CONR^{13}R^{14}$, —$C_0$-$C_6$ alkyl-$COR^{15}$, —$C_0$-$C_6$ alkyl$OCOR^{15}$, —$C_0$-$C_6$ alkyl-$OCONR^{13}R^{14}$, —$C_0$—$C_6$ alkyl-$NR^{13}CONR^{13}R^{14}$, —$C_0$-$C_6$ alkyl-$NR^{13}COR^{15}$, —$C_0$-$C_6$ alkyl-Het, —$C_0$-$C_6$ alkyl-Ar, and —$C_0$-$C_6$ alkyl-$C_3$-$C_7$ cycloalkyl, wherein said $C_1$-$C_6$ alkyl is optionally unsubstituted or substituted by one or more halo substituents, and wherein the $C_3$-$C_7$ cycloalkyl, Ar and Het moieties of said —$C_0$-$C_6$ alkyl-Het, —$C_0$-$C_6$ alkyl-Ar and —$C_0$-$C_6$ alkyl-$C_3$-$C_7$ cycloalkyl are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl-$CO_2R^{12}$, —$C_0$-$C_6$ alkyl-C(O)$SR^{12}$, —$C_0$-$C_6$ alkyl-$CONR^{13}R^{14}$, —$C_0$-$C_6$ alkyl-$COR^{15}$, —$C_0$-$C_6$ alkyl-$NR^{13}R^{14}$, —$C_0$-$C_6$ alkyl-$SR^{12}$, —$C_0$-$C_6$ alkyl-$OR^{12}$, —$C_0$-$C_6$ alkyl-$SO_3H$, —$C_0$-$C_6$ alkyl-$SO_2NR^{13}R^{14}$, —$C_0$-$C_6$ alkyl-$SO_2R^{12}$, —$C_0$-$C_6$ alkyl-$SOR^{15}$, —$C_0$-$C_6$ alkyl-$OCOR^{15}$, —$C_0$-$C_6$ alkyl-OC(O)$NR^{13}R^{14}$, —$C_0$-$C_6$ alkyl-OC(O)$OR^{15}$, —$C_0$-$C_6$ alkyl-$NR^{13}$C(O)$OR^{15}$, —$C_0$-$C_6$ alkyl-$NR^{13}$C(O)$NR^{13}R^{14}$, and —$C_0$-$C_6$ alkyl-$NR^{13}COR^{15}$, where said $C_1$-$C_6$ alkyl, is optionally unsubstituted or substituted by one or more halo substituents;

$W^3$ is selected from the group consisting of: H, halo, $C_1$-$C_6$ alkyl, —$C_0$-$C_6$ alkyl-$NR^{13}R^{14}$, —$C_0$-$C_6$ alkyl$SR^{12}$, —$C_0$-$C_6$ alkyl-$OR^{12}$, —$C_0$-$C_6$ alkyl-$CO_2R^{12}$, —$C_0$-$C_6$ alkyl-C(O)$SR^{12}$, —$C_0$-$C_6$ alkyl-$CONR^{13}R^{14}$, —$C_0$-$C_6$ alkyl-$COR^{15}$, —$C_0$-$C_6$ alkyl-$OCOR^{15}$, —$C_0$-$C_6$ alkyl-$OCONR^{13}R^{14}$, —$C_0$-$C_6$ alkyl$NR^{13}CONR^{13}R^{14}$, —$C_0$-$C_6$ alkyl-$NR^{13}COR^{15}$, —$C_0$-$C_6$ alkyl-Het, —$C_1$-$C_6$ alkyl-Ar and —$C_1$-$C_6$ alkyl-$C_3$-$C_7$ cycloalkyl, wherein said $C_1$-$C_6$ alkyl is optionally unsubstituted or substituted by one or more halo substituents;

Q is selected from $C_3$-$C_8$ cycloalkyl, Ar, and Het; wherein said $C_3$-$C_8$ cycloalkyl, Ar, and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl$CO_2R^{12}$, —$C_0$-$C_6$ alkyl-C(O)$SR^{12}$, —$C_0$-$C_6$ alkyl$CONR^{13}R^{14}$, —$C_0$-$C_6$ alkyl-$COR^{15}$, —$C_0$-$C_6$ alkyl$NR^{13}R^{14}$, —$C_0$-$C_6$ alkyl-$SR^{12}$, —$C_0$-$C_6$ alkyl-$OR^{12}$, —$C_0$-$C_6$ alkyl-$SO_3H$, —$C_0$-$C_6$ alkyl-$SO_2NR^{13}R^{14}$, —$C_0$-$C_6$ alkyl-$SO_2R^{12}$, —$C_0$-$C_6$ alkyl-$SOR^{15}$, —$C_0$-$C_6$ alkyl-$OCOR^{15}$, —$C_0$-$C_6$ alkyl-OC(O)$NR^{13}R^{14}$, —$C_0$-$C_6$ alkyl-OC(O)$OR^{15}$, —$C_0$-$C_6$ alkyl$NR^{13}$C(O)$OR^{15}$, —$C_0$-$C_6$ alkyl-$NR^{13}$C(O)$NR^{13}R^{14}$, and —$C_0$-$C_6$ alkyl-$NR^{13}COR^{15}$, where said $C_1$-$C_6$ alkyl is optionally unsubstituted or substituted by one or more halo substituents;

p is 0-8;

n is 2-8;

m is 0 or 1;

q is 0 or 1;

each $R^1$ and $R^2$ are independently selected from H, halo, $C_1$-$C_6$ alkyl, $C_3$-$C_6$ alkenyl, $C_3$-$C_6$ alkynyl, —$C_0$-$C_6$ alkyl-$NR^{13}R^{14}$, —$C_0$-$C_6$ alkyl-$OR^{12}$, —$C_0$-$C_6$ alkyl-$SR^{12}$, —$C_1$-$C_6$ alkyl-Het, —$C_1$-$C_6$ alkyl-Ar, and —$C_1$-$C_6$ alkyl-$C_3$-$C_7$ cycloalkyl, or $R^1$ and $R^2$ together with the carbon to which they are attached form a 3-5 membered carbocyclic or heterocyclic ring, wherein said heterocyclic ring contains one, or more heteroatoms selected from N, O, and S, where any of said $C_1$-$C_6$ alkyl is optionally unsubstituted or substituted by one or more halo substituents;

each $R^3$ is the same or different and is independently selected from halo, cyano, nitro, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het, —$C_0$-$C_6$ alkyl-$C_3$-$C_7$ cycloalkyl, —$C_0$-$C_6$ alkyl-$CO_2R^{12}$, —$C_0$-$C_6$ alkyl-C(O)$SR^{12}$, —$C_0$-$C_6$ alkyl-$CONR^{13}R^{14}$, —$C_0$-$C_6$ alkyl-$COR^{15}$, —$C_0$-$C_6$ alkyl-$NR^{13}R^{14}$, —$C_0$-$C_6$ alkyl-$SR^{12}$, —$C_0$-$C_6$ alkyl-$OR^{12}$, —$C_0$-$C_6$ alkyl-$SO_3H$, —$C_0$-$C_6$ alkyl$SO_2NR^{13}R^{14}$, —$C_0$-$C_6$ alkyl-$SO_2R^{12}$, —$C_0$-$C_6$ alkyl-$SOR^{15}$, —$C_0$-$C_6$ alkyl-$OCOR^{15}$, —$C_0$-$C_6$ alkyl-OC(O)$NR^{13}R^{14}$, —$C_0$-$C_6$ alkyl-OC(O)$OR^{15}$, —$C_0$-$C_6$ alkyl-$NR^{13}$C(O)$OR^{15}$, —$C_0$-$C_6$ alkyl-$NR^{13}$C(O)$NR^{13}R^{14}$, and —$C_0$-$C_6$ alkyl-$NR^{13}COR^{15}$, wherein said $C_1$-$C_6$ alkyl is optionally unsubstituted or substituted by one or more halo substituents;

each $R^4$ and $R^5$ is independently selected from H, halo, $C_1$-$C_6$ alkyl, —$C_0$-$C_6$ alkyl-Het, —$C_0$-$C_6$ alkyl-Ar, and —$C_0$-$C_6$ alkyl-$C_3$-$C_7$ cycloalkyl;

$R^6$ and $R^7$ are each independently selected from H, halo, $C_1$-$C_6$ alkyl, —$C_0$-$C_6$ alkyl-Het, —$C_0$-$C_6$ alkyl-Ar and —$C_0$-$C_6$ alkyl-$C_3$-$C_7$ cycloalkyl;

$R^8$ and $R^9$ are each independently selected from H, halo, $C_1$-$C_6$ alkyl, —$C_0$-$C_6$ alkyl-Het, —$C_0$-$C_6$ alkyl-Ar and —$C_0$-$C_6$ alkyl-$C_3$-$C_7$ cycloalkyl;

$R^{10}$ and $R^{11}$ are each independently selected from H, $C_1$-$C_{12}$ alkyl, $C_3$-$C_{12}$ alkenyl, $C_3$-$C_{12}$ alkynyl, —$C_0$-$C_8$ alkyl-Ar, —$C_0$-$C_8$ alkyl-Het, —$C_0$-$C_8$ alkyl-$C_3$-$C_7$ cycloalkyl, —$C_0$-$C_8$ alkyl-O—Ar, —$C_0$-$C_8$ alkyl-O-Het, —$C_0$-$C_8$ alkyl-O—$C_3$-$C_7$ cycloalkyl, —$C_0$-$C_8$ alkyl-S(O)$_x$—$C_0$-$C_8$ alkyl, —$C_0$-$C_8$ alkyl-S(O)$_x$—Ar, —$C_0$-$C_8$ alkyl-S(O)$_x$-Het, —$C_0$-$C_8$ alkyl-S(O)$_x$—$C_3$-$C_7$ cycloalkyl, —$C_0$-$C_8$ alkyl-NH—Ar, —$C_0$-$C_8$ alkyl-NH-Het, —$C_0$-$C_8$ alkyl-NH—$C_3$-$C_7$ cycloalkyl, —$C_0$-$C_8$ alkyl-N($C_1$-$C_4$ alkyl)-Ar, —$C_0$-$C_8$ alkyl-N($C_1$-$C_4$ alkyl)-Het, —$C_0$-$C_8$ alkyl-N($C_1$-$C_4$ alkyl-$C_3$-$C_7$ cycloalkyl, —$C_0$-$C_8$ alkyl-Ar, —$C_0$-$C_8$ alkyl-Het, and —$C_0$-$C_8$ alkyl-$C_3$-$C_7$ cycloalkyl, where x is 0, 1, or 2, or $R^{10}$ and $R^{11}$, together with the nitrogen to which they are attached, form a 4-7 membered heterocyclic ring which optionally contains one or more additional heteroatoms selected from N, O, and S, wherein said $C_1$-$C_{12}$ alkyl, $C_3$-$C_{12}$ alkenyl, or $C_3$-$C_{12}$ alkynyl is optionally substituted by one or more of the substituents independently selected from the group halo, —OH, —SH, —$NH_2$, —NH(unsubstituted $C_1$-$C_6$ alkyl), —N(unsubstituted $C_1$-$C_6$ alkyl)(unsubstituted $C_1$-$C_6$ alkyl), unsubstituted —O$C_1$-$C_6$ alkyl, —$CO_2H$, —$CO_2$(unsubstituted $C_1$-$C_6$ alkyl), —$CONH_2$, —CONH(unsubstituted $C_1$-$C_6$ alkyl), —CON(unsubstituted $C_1$-$C_6$ alkyl)(unsubstituted $C_1$-$C_6$ alkyl), —$SO_3H$, —$SO_2NH_2$, —$SO_2NH$(unsubstituted $C_1$-$C_6$ alkyl) and —$SO_2N$(unsubstituted $C_1$-$C_6$ alkyl)(unsubstituted $C_1$-$C_6$ alkyl);

$R^{12}$ is selected from H, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het and —$C_0$-$C_6$ alkyl-$C_3$-$C_7$ cycloalkyl;

each $R^{13}$ and each $R^{14}$ are independently selected from H, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het, and —$C_0$-$C_6$ alkyl-$C_3$-$C_7$ cycloalkyl, or $R^{13}$ and $R^{14}$ together with the nitrogen to which they are attached form a 4-7 membered heterocyclic ring which optionally contains one or more additional heteroatoms selected from N, O, and S; and $R^{15}$ is selected from $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het, and —$C_0$-$C_6$ alkyl-$C_3$-$C_7$ cycloalkyl.

In some embodiments, the pharmaceutically acceptable salt of formula I has the structure:

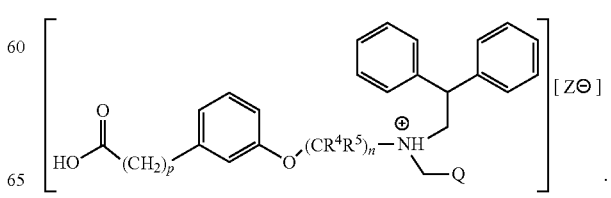

In some embodiments the pharmaceutically acceptable salt of formula I has the structure:

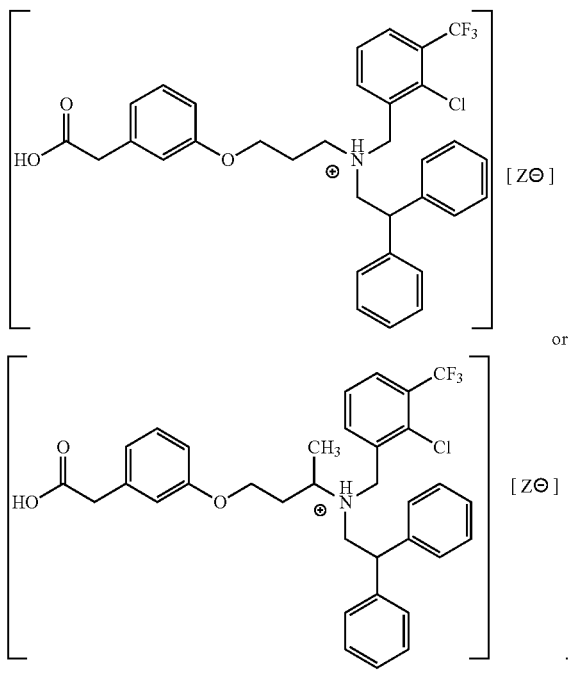

In some embodiments, the pharmaceutically acceptable salt of formula I has the structure:

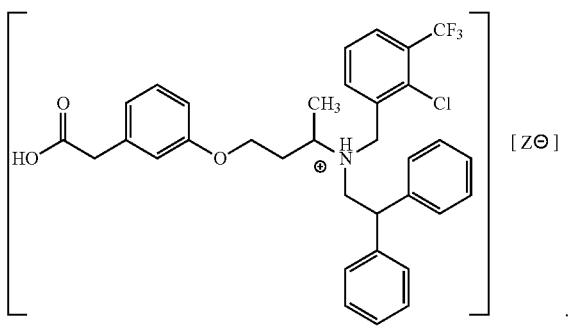

In some embodiments, the fatty acid carboxylate is a short chain fatty acid carboxylate, a medium chain fatty acid carboxylate, a long chain fatty acid carboxylate or a very long chain fatty acid carboxylate. In some embodiments, the fatty acid carboxylate is a medium chain or long chain fatty acid carboxylate. In some embodiments, the fatty acid carboxylate is a long chain fatty acid carboxylate. In some embodiments, the fatty acid carboxylate is a saturated fatty acid carboxylate selected from palmitate, caprylate, caprate, laurate, and/or stearate or an unsaturated fatty acid carboxylate selected from myristoleate, linoleate, linolenate, arachidonate, eicosenoate, palmitoleate, sapienate, oleate, elaidate, and/or vaccenate. In some embodiments, the fatty acid carboxylate is oleate.

In an aspect, the invention features a formulation comprising: any of the foregoing pharmaceutically acceptable salt; a buffering agent (e.g., a lipid soluble carboxylic acid such as sodium oleate); and a lipophilic vehicle, wherein the lipophilic vehicle comprises: a lipid excipient (e.g., a lipid excipient comprising a monoglyceride, a diglyceride, and/or a triglyceride such as glycerol linoleate); and/or a surfactant (e.g., a surfactant comprising at least one polyglycolized glyceride such as lauroyl macrogol-32 glyceride).

In some embodiments, the formulation further includes a stabilizing agent, e.g., a stabilizing agent including EDTA (ethylenediaminetetraacetic acid), sodium citrate, BHA (butylated hydroxyanisole), and/or BHT (butylated hydroxytoluene).

In some embodiments, the formulation is a semi-solid suspension. In some embodiments, the formulation is self-emulsifying. In some embodiments, the formulation is formulated for oral administration.

In some embodiments, the formulation, the lipid excipient content of the lipophilic vehicle is about 40% by weight to about 80% by weight; the surfactant content of the lipophilic vehicle is about 20% by weight to about 60% by weight; about 0.2% by weight to about 5% by weight of the formulation is lipid-soluble carboxylic acid salt; and an amount of the pharmaceutically acceptable salt is about 2% by weight to about 10% by weight of the formulation. In some embodiments, the formulation further includes about 0.2% to 2% by weight of the stabilizing agent.

In some embodiments, the pH of the formulation is from about 4 and to about 8, e.g., from about 5 and to about 7.

In some embodiments, the formulation has increased bioavailability upon oral administration compared with a formulation comprising a structure of formula I wherein $Z^{\ominus}$ is an inorganic salt, e.g., a chloride salt. For example, in some embodiments, the formulation has increased bioavailability upon oral administration compared with a formulation comprising a structure of formula I wherein $Z^{\ominus}$ is the hydrochloride salt and the hydrochloride salt is formulated as described in Collins et al. J. Med. Chem., 2002, 45:1963-1966, the formulation methods of which are herein incorporated by reference. In some embodiments, the formulation has increased bioavailability upon oral administration compared with a formulation comprising a structure of formula I that does not comprise the lipophilic vehicle.

In some embodiments, an amount of the pharmaceutically acceptable in the formulation decreases by less than about 2% after storage for 1 week, 3 weeks, 3 months, or 6 months at a temperature of 40° C. and a relative humidity of 75%.

In an aspect, the invention features, a capsule including any of the foregoing formulations. In some embodiments, the capsule is a gelatin capsule, e.g., a hard gelatin capsule or a soft gelatin capsule, such as an HPMC (hydroxypropyl methylcellulose) capsule or a non-gelatin soft shell capsule.

In an aspect, the invention features a method of treating cancer, e.g., ovarian cancer, breast cancer, lung cancer, glioblastoma, melanoma, bladder cancer, head and neck cancer, renal cell cancer, colorectal cancer, lymphoma, leukemia, multiple myeloma, hepatocellular carcinoma, a high grade neuroendocrine tumor and/or a small cell carcinoma such as a lung cancer. This method includes administering an effective amount of any of the foregoing pharmaceutically acceptable salt, formulations, or capsules to a subject in need thereof.

In an aspect, the invention features a method of producing a formulation. This method includes mixing a lipophilic vehicle, comprising a lipid excipient and/or a surfactant, and a compound of formula II:

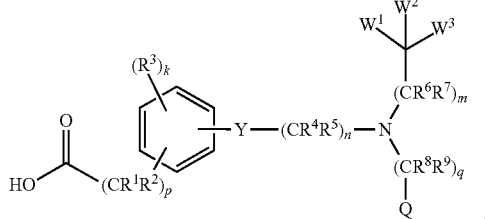

II or a pharmaceutically acceptable salt thereof,
wherein:

Y is selected from —O—, —S—, —N($R^{12}$)—, and —C($R^4$)($R^5$)—;

$W^1$ is selected from $C_1$-$C_6$ alkyl, $C_0$-$C_6$ alkyl, $C_3$-$C_6$ cycloalkyl, aryl and Het, wherein said $C_1$-$C_8$ alkyl, $C_3$-$C_8$ cycloalkyl, Ar and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl-$CO_2R^{12}$, —$C_0$-$C_6$ alkyl-C(O)$SR^{12}$, —$C_0$-$C_6$ alkyl-CONR$^{13}R^{14}$, —$C_0$-$C_6$ alkyl-COR$^{15}$, —$C_0$-$C_6$ alkyl-NR$^{13}R^{14}$, —$C_0$-$C_6$ alkyl-SR$^{12}$, —$C_0$-$C_6$ alkyl-OR$^{12}$, —$C_0$-$C_6$ alkyl-SO$_3$H, —$C_0$-$C_6$ alkyl-SO$_2$NR$^{13}R^{14}$, —$C_0$-$C_6$ alkyl-SO$_2R^{12}$, —$C_0$-$C_6$ alkyl-SOR$^{15}$, —$C_0$-$C_6$ alkylOCOR$^{15}$, —$C_0$-$C_6$ alkyl-OC(O)NR$^{13}R^{14}$, —$C_0$-$C_6$ alkyl-OC(O)OR$^{15}$, —$C_0$-$C_6$ alkyl-NR$^{13}$C(O)OR$^{15}$, —$C_0$-$C_6$ alkyl-NR$^{13}$C(O)NR$^{13}R^{14}$, and —$C_0$-$C_6$ alkyl-NR$^{13}$COR$^{15}$, where said $C_1$-$C_6$ alkyl, is optionally unsubstituted or substituted by one or more halo substituents;

$W^2$ is selected from H, halo, $C_1$-$C_6$ alkyl, $C_2$-$C_6$ alkenyl, $C_2$-$C_6$ alkynyl, —$C_0$-$C_6$ alkyl-NR$^{13}R^{14}$, —$C_0$-$C_6$ alkyl-SR$^{12}$, —$C_0$-$C_6$ alkyl-OR$^{12}$, —$C_0$-$C_6$ alkylCO$_2R^{12}$, —$C_0$-$C_6$ alkyl-C(O)SR$^{12}$, —$C_0$-$C_6$ alkylCONR$^{13}R^{14}$, —$C_0$-$C_6$ alkyl-COR$^{15}$, —$C_0$-$C_6$ alkylOCOR$^{15}$, —$C_0$-$C_6$ alkyl-OCONR$^{13}R^{14}$, —$C_0$-$C_6$ alkyl-NR$^{13}$CONR$^{13}R^{14}$, —$C_0$-$C_6$ alkyl-NR$^{13}$COR$^{15}$, —$C_0$-$C_6$ alkyl-Het, —$C_0$-$C_6$ alkyl-Ar, and —$C_0$-$C_6$ alkyl-$C_3$-$C_7$ cycloalkyl, wherein said $C_1$-$C_6$ alkyl is optionally unsubstituted or substituted by one or more halo substituents, and wherein the $C_3$-$C_7$ cycloalkyl, Ar and Het moieties of said —$C_0$-$C_6$ alkyl-Het, —$C_0$-$C_6$ alkyl-Ar and —$C_0$-$C_6$ alkyl-$C_3$-$C_7$ cycloalkyl are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl-CO$_2R^{12}$, —$C_0$-$C_6$ alkyl-C(O)SR$^{12}$, —$C_0$-$C_6$ alkyl-CONR$^{13}R^{14}$, —$C_0$-$C_6$ alkyl-COR$^{15}$, —$C_0$-$C_6$ alkyl-NR$^{13}R^{14}$, —$C_0$-$C_6$ alkyl-SR$^{12}$, —$C_0$-$C_6$ alkyl-OR$^{12}$, —$C_0$-$C_6$ alkyl-SO$_3$H, —$C_0$-$C_6$ alkyl-SO$_2$NR$^{13}R^{14}$, —$C_0$-$C_6$ alkyl-SO$_2R^{12}$, —$C_0$-$C_6$ alkyl-SOR$^{15}$, —$C_0$-$C_6$ alkyl-OCOR$^{15}$, —$C_0$-$C_6$ alkyl-OC(O)NR$^{13}R^{14}$, —$C_0$-$C_6$ alkyl-OC(O)OR$^{15}$, —$C_0$-$C_6$ alkyl-NR$^{13}$C(O)OR$^{15}$, —$C_0$-$C_6$ alkyl-NR$^{13}$C(O)NR$^{13}R^{14}$, and —$C_0$-$C_6$ alkyl-NR$^{13}$COR$^{15}$, where said $C_1$-$C_6$ alkyl, is optionally unsubstituted or substituted by one or more halo substituents;

$W^3$ is selected from the group consisting of: H, halo, $C_1$-$C_6$ alkyl, —$C_0$-$C_6$ alkyl-NR$^{13}R^{14}$, —$C_0$-$C_6$ alkylSR$^{12}$, —$C_0$-$C_6$ alkyl-OR$^{12}$, —$C_0$-$C_6$ alkyl-CO$_2R^{12}$, —$C_0$-$C_6$ alkyl-C(O)SR$^{12}$, —$C_0$-$C_6$ alkyl-CONR$^{13}R^{14}$, —$C_0$-$C_6$ alkyl-COR$^{15}$, —$C_0$-$C_6$ alkyl-OCOR$^{15}$, —$C_0$-$C_6$ alkyl-OCONR$^{13}R^{14}$, —$C_0$-$C_6$ alkylNR$^{13}$CONR$^{13}R^{14}$, —$C_0$-$C_6$ alkyl-NR$^{13}$COR$^{15}$, —$C_0$-$C_6$ alkyl-Het, —$C_1$-$C_6$ alkyl-Ar and —$C_1$-$C_6$ alkyl-$C_3$-$C_7$ cycloalkyl, wherein said $C_1$-$C_6$ alkyl is optionally unsubstituted or substituted by one or more halo substituents;

Q is selected from $C_3$-$C_8$ cycloalkyl, Ar, and Het; wherein said $C_3$-$C_8$ cycloalkyl, Ar, and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkylCO$_2R^{12}$, —$C_0$-$C_6$ alkyl-C(O)SR$^{12}$, —$C_0$-$C_6$ alkylCONR$^{13}R^{14}$, —$C_0$-$C_6$ alkyl-COR$^{15}$, —$C_0$-$C_6$ alkylNR$^{13}R^{14}$, —$C_0$-$C_6$ alkyl-SR$^{12}$, —$C_0$-$C_6$ alkyl-OR$^{12}$, —$C_0$-$C_6$ alkyl-SO$_3$H, —$C_0$-$C_6$ alkyl-SO$_2$NR$^{13}R^{14}$, —$C_0$-$C_6$ alkyl-SO$_2R^{12}$, —$C_0$-$C_6$ alkyl-SOR$^{15}$, —$C_0$-$C_6$ alkyl-OCOR$^{15}$, —$C_0$-$C_6$ alkyl-OC(O)NR$^{13}R^{14}$, —$C_0$-$C_6$ alkyl-OC(O)OR$^{15}$, —$C_0$-$C_6$ alkylNR$^{13}$C(O)OR$^{15}$, —$C_0$-$C_6$ alkyl-NR$^{13}$C(O)NR$^{13}R^{14}$, and —$C_0$-$C_6$ alkyl-NR$^{13}$COR$^{15}$, where said $C_1$-$C_6$ alkyl is optionally unsubstituted or substituted by one or more halo substituents;

p is 0-8;
n is 2-8;
m is 0 or 1;
q is 0 or 1;

each $R^1$ and $R^2$ are independently selected from H, halo, $C_1$-$C_6$ alkyl, $C_3$-$C_6$ alkenyl, $C_3$-$C_6$ alkynyl, —$C_0$-$C_6$ alkyl-NR$^{13}R^{14}$, —$C_0$-$C_6$ alkyl-OR$^{12}$, —$C_0$-$C_6$ alkyl-SR$^{12}$, —$C_1$-$C_6$ alkyl-Het, —$C_1$-$C_6$ alkyl-Ar, and —$C_1$-$C_6$ alkyl-$C_3$-$C_7$ cycloalkyl, or $R^1$ and $R^2$ together with the carbon to which they are attached form a 3-5 membered carbocyclic or heterocyclic ring, wherein said heterocyclic ring contains one, or more heteroatoms selected from N, O, and S, where any of said $C_1$-$C_6$ alkyl is optionally unsubstituted or substituted by one or more halo substituents;

each $R^3$ is the same or different and is independently selected from halo, cyano, nitro, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het, —$C_0$-$C_6$ alkyl-$C_3$-$C_7$ cycloalkyl, —$C_0$-$C_6$ alkyl-CO$_2R^{12}$, —$C_0$-$C_6$ alkyl-C(O)SR$^{12}$, —$C_0$-$C_6$ alkyl-CONR$^{13}R^{14}$, —$C_0$-$C_6$ alkyl-COR$^{15}$, —$C_0$-$C_6$ alkyl-NR$^{13}R^{14}$, —$C_0$-$C_6$ alkyl-SR$^{12}$, —$C_0$-$C_6$ alkyl-OR$^{12}$, —$C_0$-$C_6$ alkyl-SO$_3$H, —$C_0$-$C_6$ alkylSO$_2$NR$^{13}R^{14}$, —$C_0$-$C_6$ alkyl-SO$_2R^{12}$, —$C_0$-$C_6$ alkyl-SOR$^{15}$, —$C_0$-$C_6$ alkyl-OCOR$^{15}$, —$C_0$-$C_6$ alkyl-OC(O)NR$^{13}R^{14}$, —$C_0$-$C_6$ alkyl-OC(O)OR$^{15}$, —$C_0$-$C_6$ alkyl-NR$^{13}$C(O)OR$^{15}$, —$C_0$-$C_6$ alkyl-NR$^{13}$C(O)NR$^{13}R^{14}$, and —$C_0$-$C_6$ alkyl-NR$^{13}$COR$^{15}$, wherein said $C_1$-$C_6$ alkyl is optionally unsubstituted or substituted by one or more halo substituents;

each $R^4$ and $R^5$ is independently selected from H, halo, $C_1$-$C_6$ alkyl, —$C_0$-$C_6$ alkyl-Het, —$C_0$-$C_6$ alkyl-Ar, and —$C_0$-$C_6$ alkyl-$C_3$-$C_7$ cycloalkyl;

$R^6$ and $R^7$ are each independently selected from H, halo, $C_1$-$C_6$ alkyl, —$C_0$-$C_6$ alkyl-Het, —$C_0$-$C_6$ alkyl-Ar and —$C_0$-$C_6$ alkyl-$C_3$-$C_7$ cycloalkyl;

$R^8$ and $R^9$ are each independently selected from H, halo, $C_1$-$C_6$ alkyl, —$C_0$-$C_6$ alkyl-Het, —$C_0$-$C_6$ alkyl-Ar and —$C_0$-$C_6$ alkyl-$C_3$-$C_7$ cycloalkyl;

$R^{10}$ and $R^{11}$ are each independently selected from H, $C_1$-$C_{12}$ alkyl, $C_3$-$C_{12}$ alkenyl, $C_3$-$C_{12}$ alkynyl, —$C_0$-$C_8$ alkyl-Ar, —$C_0$-$C_8$ alkyl-Het, —$C_0$-$C_8$ alkyl-$C_3$-$C_7$ cycloalkyl, —$C_0$-$C_8$ alkyl-O—Ar, —$C_0$-$C_8$ alkyl-O-Het, —$C_0$-$C_8$ alkyl-O—$C_3$-$C_7$ cycloalkyl, —$C_0$-$C_8$ alkyl-S(O)$_x$—$C_0$-$C_8$ alkyl, —$C_0$-$C_8$ alkyl-S(O)$_x$—Ar, —$C_0$-$C_8$ alkyl-S(O)$_x$-Het, —$C_0$-$C_8$ alkyl-S(O)$_x$—$C_3$-$C_7$ cycloalkyl, —$C_0$-$C_8$ alkyl-NH—Ar, —$C_0$-$C_8$ alkyl-NH-Het, —$C_0$-$C_8$ alkyl-NH—$C_3$-$C_7$ cycloalkyl, —$C_0$-$C_8$ alkyl-N($C_1$-$C_4$ alkyl)-Ar, —$C_0$-$C_8$ alkyl-N($C_1$-$C_4$ alkyl)-Het, —$C_0$-$C_8$ alkyl-N($C_1$-$C_4$ alkyl-$C_3$-$C_7$ cycloalkyl, —$C_0$-$C_8$ alkyl-Ar, —$C_0$-$C_8$ alkyl-Het, and —$C_0$-$C_8$ alkyl-$C_3$-$C_7$ cycloalkyl, where x is 0, 1, or 2, or $R^{10}$ and $R^{11}$, together with the nitrogen to which they are attached, form a 4-7 membered heterocyclic ring which optionally contains one or more additional heteroatoms selected from N, O, and S, wherein said $C_1$-$C_{12}$ alkyl, $C_3$-$C_{12}$ alkenyl, or $C_3$-$C_{12}$ alkynyl is optionally substituted by one or more of the substituents independently selected from the group halo, —OH, —SH, —NH$_2$, —NH(unsubstituted $C_1$-$C_6$ alkyl), —N(unsubstituted $C_1$-$C_6$ alkyl)(unsubstituted $C_1$-$C_6$ alkyl), unsubstituted —O$C_1$-$C_6$ alkyl, —CO$_2$H, —CO$_2$(unsubstituted $C_1$-$C_6$ alkyl), —CONH$_2$, —CONH(unsubstituted $C_1$-$C_6$ alkyl), —CON(unsubstituted $C_1$-$C_6$ alkyl)(unsubstituted $C_1$-$C_6$ alkyl), —SO$_3$H, —SO$_2$NH$_2$, —SO$_2$NH(unsubstituted $C_1$-$C_6$ alkyl) and —SO$_2$N(unsubstituted $C_1$-$C_6$ alkyl)(unsubstituted $C_1$-$C_6$ alkyl);

$R^{12}$ is selected from H, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het and —$C_0$-$C_6$ alkyl-$C_3$-$C_7$ cycloalkyl;

each $R^{13}$ and each $R^{14}$ are independently selected from H, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het, and —$C_0$-$C_6$ alkyl-$C_3$-$C_7$ cycloalkyl, or $R^{13}$ and $R^{14}$ together with the nitrogen to which they are attached form a 4-7 membered heterocyclic ring which optionally contains one or more additional heteroatoms selected from N, O, and S; and $R^{15}$ is selected from $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het, and —$C_0$-$C_6$ alkyl-$C_3$-$C_7$ cycloalkyl.

In some embodiments, the method includes dissolving the compound of formula II, or a pharmaceutically acceptable salt thereof, in the lipophilic vehicle. In some embodiments, the method further includes adding a sodium salt of a fatty acid. In some embodiments, the sodium salt of a fatty acid is added to the lipophilic vehicle before the compound of formula II, or the pharmaceutically acceptable salt thereof. In some embodiments, sodium chloride precipitates upon addition of the sodium salt of a fatty acid. In some embodiments, the method further includes adding a stabilizing agent.

In some embodiments, the compound is:

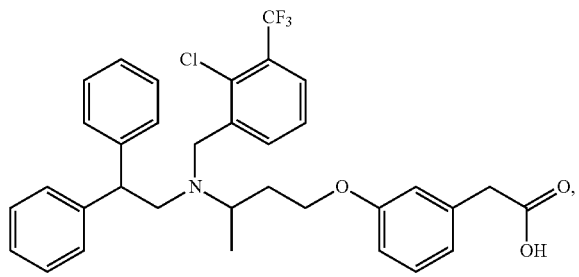 [SMILES: CC(CCOc1cccc(CC(=O)O)c1)N(Cc1cccc(C(F)(F)F)c1Cl)CC(c1ccccc1)c1ccccc1]

or a pharmaceutically acceptable salt thereof.

In some embodiments, the compound is a hydrochloride salt of:

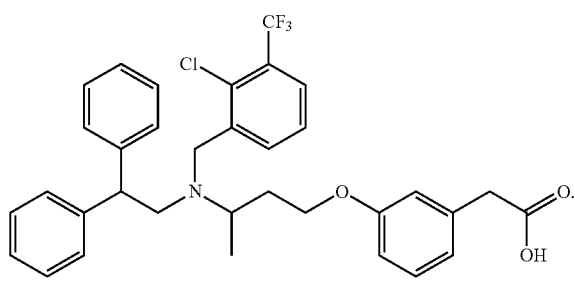 [SMILES: CC(CCOc1cccc(CC(=O)O)c1)N(Cc1cccc(C(F)(F)F)c1Cl)CC(c1ccccc1)c1ccccc1]

In some embodiments, the lipophilic vehicle comprises at least one glycerol fatty acid ester, e.g., glycerol linoleate. In some embodiments, the lipophilic vehicle comprises at least one polyglycolized glyceride, e.g., lauroyl macrogol-32 glyceride. In some embodiments, the stabilizing agent comprises EDTA and/or sodium citrate.

In an aspect, the invention features a formulation including:

a compound of formula II:

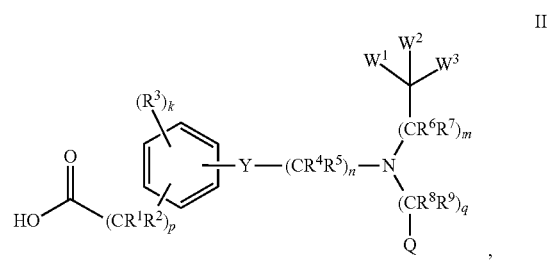

II or a pharmaceutically acceptable salt thereof, wherein:

Y is selected from —O—, —S—, —N($R^{12}$)—, and —C($R^4$)($R^5$)—;

$W^1$ is selected from $C_1$-$C_6$ alkyl, $C_0$-$C_6$ alkyl, $C_3$-$C_6$ cycloalkyl, aryl and Het, wherein said $C_1$-$C_8$ alkyl, $C_3$-$C_8$ cycloalkyl, Ar and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl-CO$_2$R$^{12}$, —$C_0$-$C_6$ alkyl-C(O)SR$^{12}$, —$C_0$-$C_6$ alkyl-CONR$^{13}$R$^{14}$, —$C_0$-$C_6$ alkyl-COR$^{15}$, —$C_0$-$C_6$ alkyl-NR$^{13}$R$^{14}$, —$C_0$-$C_6$ alkyl-SR$^{12}$, —$C_0$-$C_6$ alkyl-OR$^{12}$, —$C_0$-$C_6$ alkyl-SO$_3$H, —$C_0$-$C_6$ alkyl-SO$_2$NR$^{13}$R$^{14}$, —$C_0$-$C_6$ alkyl-SO$_2$R$^{12}$, —$C_0$-$C_6$ alkyl-SOR$^{15}$, —$C_0$-$C_6$ alkylOCOR$^{15}$, —$C_0$-$C_6$ alkyl-OC(O)NR$^{13}$R$^{14}$, —$C_0$-$C_6$ alkyl-OC(O)OR$^{15}$, —$C_0$-$C_6$ alkyl-NR$^{13}$C(O)OR$^{15}$, —$C_0$-$C_6$ alkyl-NR$^{13}$C(O)NR$^{13}$R$^{14}$, and —$C_0$-$C_6$ alkyl-NR$^{13}$COR$^{15}$, where said $C_1$-$C_6$ alkyl, is optionally unsubstituted or substituted by one or more halo substituents;

$W^2$ is selected from H, halo, $C_1$-$C_6$ alkyl, $C_2$-$C_6$ alkenyl, $C_2$-$C_6$ alkynyl, —$C_0$-$C_6$ alkyl-NR$^{13}$R$^{14}$, —$C_0$-$C_6$ alkyl-SR$^{12}$, —$C_0$-$C_6$ alkyl-OR$^{12}$, —$C_0$-$C_6$ alkylCO$_2$R$^{12}$, —$C_0$-$C_6$ alkyl-C(O)SR$^{12}$, —$C_0$-$C_6$ alkylCONR$^{13}$R$^{14}$, —$C_0$-$C_6$ alkyl-COR$^{15}$, —$C_0$-$C_6$ alkylOCOR$^{15}$, —$C_0$-$C_6$ alkyl-OCONR$^{13}$R$^{14}$, —$C_0$-$C_6$ alkyl-NR$^{13}$CONR$^{13}$R$^{14}$, —$C_0$-$C_6$ alkyl-NR$^{13}$COR$^{15}$, —$C_0$-$C_6$ alkyl-Het, —$C_0$-$C_6$ alkyl-Ar, and —$C_0$-$C_6$ alkyl-$C_3$-$C_7$ cycloalkyl, wherein said $C_1$-$C_6$ alkyl is optionally unsubstituted or substituted by one or more halo substituents, and wherein the $C_3$-$C_7$ cycloalkyl, Ar and Het moieties of said —$C_0$-$C_6$ alkyl-Het, —$C_0$-$C_6$ alkyl-Ar and —$C_0$-$C_6$ alkyl-$C_3$-$C_7$ cycloalkyl are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl-CO$_2$R$^{12}$, —$C_0$-$C_6$ alkyl-C(O)SR$^{12}$, —$C_0$-$C_6$ alkyl-CONR$^{13}$R$^{14}$, —$C_0$-$C_6$ alkyl-COR$^{15}$, —$C_0$-$C_6$ alkyl-NR$^{13}$R$^{14}$, —$C_0$-$C_6$ alkyl-SR$^{12}$, —$C_0$-$C_6$ alkyl-OR$^{12}$, —$C_0$-$C_6$ alkyl-SO$_3$H, —$C_0$-$C_6$ alkyl-SO$_2$NR$^{13}$R$^{14}$, —$C_0$-$C_6$ alkyl-SO$_2$R$^{12}$, —$C_0$-$C_6$ alkyl-SOR$^{15}$, —$C_0$-$C_6$ alkyl-OCOR$^{15}$, —$C_0$-$C_6$ alkyl-OC(O)NR$^{13}$R$^{14}$, —$C_0$-$C_6$ alkyl-OC(O)OR$^{15}$, —$C_0$-$C_6$ alkyl-NR$^{13}$C(O)OR$^{15}$, —$C_0$-$C_6$ alkyl-NR$^{13}$C(O)NR$^{13}$R$^{14}$, and —$C_0$-$C_6$ alkyl-NR$^{13}$COR$^{15}$, where said $C_1$-$C_6$ alkyl, is optionally unsubstituted or substituted by one or more halo substituents;

W³ is selected from the group consisting of: H, halo, C₁-C₆ alkyl, —C₀-C₆ alkyl-NR¹³R¹⁴, —C₀-C₆ alkylSR¹², —C₀-C₆ alkyl-OR¹², —C₀-C₆ alkyl-CO₂R¹², —C₀-C₆ alkyl-C(O)SR¹², —C₀-C₆ alkyl-CONR¹³R¹⁴, —C₀-C₆ alkyl-COR¹⁵, —C₀-C₆ alkyl-OCOR¹⁵, —C₀-C₆ alkyl-OCONR¹³R¹⁴, —C₀-C₆ alkylNR¹³CONR¹³R¹⁴, —C₀-C₆ alkyl-NR¹³COR¹⁵, —C₀-C₆ alkyl-Het, —C₁-C₆ alkyl-Ar and —C₁-C₆ alkyl-C₃-C₇ cycloalkyl, wherein said C₁-C₆ alkyl is optionally unsubstituted or substituted by one or more halo substituents;

Q is selected from C₃-C₈ cycloalkyl, Ar, and Het; wherein said C₃-C₈ cycloalkyl, Ar, and Het are optionally unsubstituted or substituted with one or more groups independently selected from halo, cyano, nitro, C₁-C₆ alkyl, C₃-C₆ alkenyl, C₃-C₆ alkynyl, —C₀-C₆ alkylCO₂R¹², —C₀-C₆ alkyl-C(O)SR¹², —C₀-C₆ alkylCONR¹³R¹⁴, —C₀-C₆ alkyl-COR¹⁵, —C₀-C₆ alkylNR¹³R¹⁴, —C₀-C₆ alkyl-SR¹², —C₀-C₆ alkyl-OR¹², —C₀-C₆ alkyl-SO₃H, —C₀-C₆ alkyl-SO₂NR¹³R¹⁴, —C₀-C₆ alkyl-SO₂R¹², —C₀-C₆ alkyl-SOR¹⁵, —C₀-C₆ alkyl-OCOR¹⁵, —C₀-C₆ alkyl-OC(O)NR¹³R¹⁴, —C₀-C₆ alkyl-OC(O)OR¹⁵, —C₀-C₆ alkylNR¹³C(O)OR¹⁵, —C₀-C₆ alkyl-NR¹³C(O)NR¹³R¹⁴, and —C₀-C₆ alkyl-NR¹³COR¹⁵, where said C₁-C₆ alkyl is optionally unsubstituted or substituted by one or more halo substituents;

p is 0-8;

n is 2-8;

m is 0 or 1;

q is 0 or 1;

each R¹ and R² are independently selected from H, halo, C₁-C₆ alkyl, C₃-C₆ alkenyl, C₃-C₆ alkynyl, —C₀-C₆ alkyl-NR¹³R¹⁴, —C₀-C₆ alkyl-OR¹², —C₀-C₆ alkyl-SR¹², —C₁-C₆ alkyl-Het, —C₁-C₆ alkyl-Ar, and —C₁-C₆ alkyl-C₃-C₇ cycloalkyl, or R¹ and R² together with the carbon to which they are attached form a 3-5 membered carbocyclic or heterocyclic ring, wherein said heterocyclic ring contains one, or more heteroatoms selected from N, O, and S, where any of said C₁-C₆ alkyl is optionally unsubstituted or substituted by one or more halo substituents;

each R³ is the same or different and is independently selected from halo, cyano, nitro, C₁-C₆ alkyl, C₃-C₆ alkenyl, C₃-C₆ alkynyl, —C₀-C₆ alkyl-Ar, —C₀-C₆ alkyl-Het, —C₀-C₆ alkyl-C₃-C₇ cycloalkyl, —C₀-C₆ alkyl-CO₂R¹², —C₀-C₆ alkyl-C(O)SR¹², —C₀-C₆ alkyl-CONR¹³R¹⁴, —C₀-C₆ alkyl-COR¹⁵, —C₀-C₆ alkyl-NR¹³R¹⁴, —C₀-C₆ alkyl-SR¹², —C₀-C₆ alkyl-OR¹², —C₀-C₆ alkyl-SO₃H, —C₀-C₆ alkylSO₂NR¹³R¹⁴, —C₀-C₆ alkyl-SO₂R¹², —C₀-C₆ alkyl-SOR¹⁵, —C₀-C₆ alkyl-OCOR¹⁵, —C₀-C₆ alkyl-OC(O)NR¹³R¹⁴, —C₀-C₆ alkyl-OC(O)OR¹⁵, —C₀-C₆ alkyl-NR¹³C(O)OR¹⁵, —C₀-C₆ alkyl-NR¹³C(O)NR¹³R¹⁴, and —C₀-C₆ alkyl-NR¹³COR¹⁵, wherein said C₁-C₆ alkyl is optionally unsubstituted or substituted by one or more halo substituents;

each R⁴ and R⁵ is independently selected from H, halo, C₁-C₆ alkyl, —C₀-C₆ alkyl-Het, —C₀-C₆ alkyl-Ar, and —C₀-C₆ alkyl-C₃-C₇ cycloalkyl;

R⁶ and R⁷ are each independently selected from H, halo, C₁-C₆ alkyl, —C₀-C₆ alkyl-Het, —C₀-C₆ alkyl-Ar and —C₀-C₆ alkyl-C₃-C₇ cycloalkyl;

R⁸ and R⁹ are each independently selected from H, halo, C₁-C₆ alkyl, —C₀-C₆ alkyl-Het, —C₀-C₆ alkyl-Ar and —C₀-C₆ alkyl-C₃-C₇ cycloalkyl;

R¹⁰ and R¹¹ are each independently selected from H, C₁-C₁₂ alkyl, C₃-C₁₂ alkenyl, C₃-C₁₂ alkynyl, —C₀-C₈ alkyl-Ar, —C₀-C₈ alkyl-Het, —C₀-C₈ alkyl-C₃-C₇ cycloalkyl, —C₀-C₈ alkyl-O—Ar, —C₀-C₈ alkyl-O-Het, —C₀-C₈ alkyl-O—C₃-C₇ cycloalkyl, —C₀-C₈ alkyl-S(O)ₓ—C₀-C₈ alkyl, —C₀-C₈ alkyl-S(O)ₓ—Ar, —C₀-C₈ alkyl-S(O)ₓ-Het, —C₀-C₈ alkyl-S(O)ₓ—C₃-C₇ cycloalkyl, —C₀-C₈ alkyl-NH—Ar, —C₀-C₈ alkyl-NH-Het, —C₀-C₈ alkyl-NH—C₃-C₇ cycloalkyl, —C₀-C₈ alkyl-N(C₁-C₄ alkyl)-Ar, —C₀-C₈ alkyl-N(C₁-C₄ alkyl)-Het, —C₀-C₈ alkyl-N(C₁-C₄ alkyl-C₃-C₇ cycloalkyl, —C₀-C₈ alkyl-Ar, —C₀-C₈ alkyl-Het, and —C₀-C₈ alkyl-C₃-C₇ cycloalkyl, where x is 0, 1, or 2, or R¹⁰ and R¹¹, together with the nitrogen to which they are attached, form a 4-7 membered heterocyclic ring which optionally contains one or more additional heteroatoms selected from N, O, and S, wherein said C₁-C₁₂ alkyl, C₃-C₁₂ alkenyl, or C₃-C₁₂ alkynyl is optionally substituted by one or more of the substituents independently selected from the group halo, —OH, —SH, —NH₂, —NH(unsubstituted C₁-C₆ alkyl), —N(unsubstituted C₁-C₆ alkyl)(unsubstituted C₁-C₆ alkyl), unsubstituted —OC₁-C₆ alkyl, —CO₂H, —CO₂(unsubstituted C₁-C₆ alkyl), —CONH₂, —CONH(unsubstituted C₁-C₆ alkyl), —CON(unsubstituted C₁-C₆ alkyl)(unsubstituted C₁-C₆ alkyl), —SO₃H, —SO₂NH₂, —SO₂NH(unsubstituted C₁-C₆ alkyl) and —SO₂N(unsubstituted C₁-C₆ alkyl)(unsubstituted C₁-C₆ alkyl);

R¹² is selected from H, C₁-C₆ alkyl, C₃-C₆ alkenyl, C₃-C₆ alkynyl, —C₀-C₆ alkyl-Ar, —C₀-C₆ alkyl-Het and —C₀-C₆ alkyl-C₃-C₇ cycloalkyl;

each R¹³ and each R¹⁴ are independently selected from H, C₁-C₆ alkyl, C₃-C₆ alkenyl, C₃-C₆ alkynyl, —C₀-C₆ alkyl-Ar, —C₀-C₆ alkyl-Het, and —C₀-C₆ alkyl-C₃-C₇ cycloalkyl, or R¹³ and R¹⁴ together with the nitrogen to which they are attached form a 4-7 membered heterocyclic ring which optionally contains one or more additional heteroatoms selected from N, O, and S; and R¹⁵ is selected from C₁-C₆ alkyl, C₃-C₆ alkenyl, C₃-C₆ alkynyl, —C₀-C₆ alkyl-Ar, —C₀-C₆ alkyl-Het, and —C₀-C₆ alkyl-C₃-C₇ cycloalkyl; and a lipophilic vehicle, comprising at least one lipophilic excipient, in which the compound of the formula II, or the pharmaceutically acceptable salt thereof, is soluble, wherein a pH of the formulation is from about pH 4 to about pH 8.

In an aspect, the invention features a formulation comprising:

a compound of formula II:

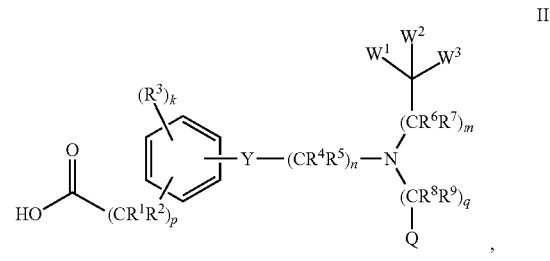

or a pharmaceutically acceptable salt thereof, wherein:

Y is selected from —O—, —S—, —N(R¹²)—, and —C(R⁴)(R⁵)—;

W¹ is selected from C₁-C₆ alkyl, C₀-C₆ alkyl, C₃-C₆ cycloalkyl, aryl and Het, wherein said C₁-C₈ alkyl, C₃-C₈ cycloalkyl, Ar and Het are optionally unsubstituted or substituted with one or more groups independently selected from halo, cyano, nitro, C₁-C₆ alkyl, C₃-C₆ alkenyl, C₃-C₆ alkynyl, —C₀-C₆ alkyl-CO₂R¹², —C₀-C₆ alkyl-C(O)SR¹², —C₀-C₆ alkyl-CONR¹³R¹⁴, —C₀-C₆ alkyl-COR¹⁵, —C₀-

$C_6$ alkyl-$NR^{13}R^{14}$, —$C_0$-$C_6$ alkyl-$SR^{12}$, —$C_0$-$C_6$ alkyl-$OR^{12}$, —$C_0$-$C_6$ alkyl-$SO_3H$, —$C_0$-$C_6$ alkyl-$SO_2NR^{13}R^{14}$, —$C_0$-$C_6$ alkyl-$SO_2R^{12}$, —$C_0$-$C_6$ alkyl-$SOR^{15}$, —$C_0$-$C_6$ alkylOCOR$^{15}$, —$C_0$-$C_6$ alkyl-OC(O)$NR^{13}R^{14}$, —$C_0$-$C_6$ alkyl-OC(O)$OR^{15}$, —$C_0$-$C_6$ alkyl-$NR^{13}C(O)OR^{15}$, —$C_0$-$C_6$ alkyl-$NR^{13}C(O)NR^{13}R^{14}$, and —$C_0$-$C_6$ alkyl-$NR^{13}COR^{15}$, where said $C_1$-$C_6$ alkyl, is optionally unsubstituted or substituted by one or more halo substituents;

$W^2$ is selected from H, halo, $C_1$-$C_6$ alkyl, $C_2$-$C_6$ alkenyl, $C_2$-$C_6$ alkynyl, —$C_0$-$C_6$ alkyl-$NR^{13}R^{14}$, —$C_0$-$C_6$ alkyl-$SR^{12}$, —$C_0$-$C_6$ alkyl-$OR^{12}$, —$C_0$-$C_6$ alkyl$CO_2R^{12}$, —$C_0$-$C_6$ alkyl-C(O)$SR^{12}$, —$C_0$-$C_6$ alkylCONR$^{13}R^{14}$, —$C_0$-$C_6$ alkyl-COR$^{15}$, —$C_0$-$C_6$ alkylOCOR$^{15}$, —$C_0$-$C_6$ alkyl-OCONR$^{13}R^{14}$, —$C_0$-$C_6$ alkyl-$NR^{13}CONR^{13}R^{14}$, —$C_0$-$C_6$ alkyl-$NR^{13}COR^{15}$, —$C_0$-$C_6$ alkyl-Het, —$C_0$-$C_6$ alkyl-Ar, and —$C_0$-$C_6$ alkyl-$C_3$-$C_7$ cycloalkyl, wherein said $C_1$-$C_6$ alkyl is optionally unsubstituted or substituted by one or more halo substituents, and wherein the $C_3$-$C_7$ cycloalkyl, Ar and Het moieties of said —$C_0$-$C_6$ alkyl-Het, —$C_0$-$C_6$ alkyl-Ar and —$C_0$-$C_6$ alkyl-$C_3$-$C_7$ cycloalkyl are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl-$CO_2R^{12}$, —$C_0$-$C_6$ alkyl-C(O)$SR^{12}$, —$C_0$-$C_6$ alkyl-CONR$^{13}R^{14}$, —$C_0$-$C_6$ alkyl-COR$^{15}$, —$C_0$-$C_6$ alkyl-$NR^{13}R^{14}$, —$C_0$-$C_6$ alkyl-$SR^{12}$, —$C_0$-$C_6$ alkyl-$OR^{12}$, —$C_0$-$C_6$ alkyl-$SO_3H$, —$C_0$-$C_6$ alkyl-$SO_2NR^{13}R^{14}$, —$C_0$-$C_6$ alkyl-$SO_2R^{12}$, —$C_0$-$C_6$ alkyl-$SOR^{15}$, —$C_0$-$C_6$ alkyl-$OCOR^{15}$, —$C_0$-$C_6$ alkyl-OC(O)$NR^{13}R^{14}$, —$C_0$-$C_6$ alkyl-OC(O)$OR^{15}$, —$C_0$-$C_6$ alkyl-$NR^{13}C(O)OR^{15}$, —$C_0$-$C_6$ alkyl-$NR^{13}C(O)NR^{13}R^{14}$, and —$C_0$-$C_6$ alkyl-$NR^{13}COR^{15}$, where said $C_1$-$C_6$ alkyl, is optionally unsubstituted or substituted by one or more halo substituents;

$W^3$ is selected from the group consisting of: H, halo, $C_1$-$C_6$ alkyl, —$C_0$-$C_6$ alkyl-$NR^{13}R^{14}$, —$C_0$-$C_6$ alkylSR$^{12}$, —$C_0$-$C_6$ alkyl-$OR^{12}$, —$C_0$-$C_6$ alkyl-$CO_2R^{12}$, —$C_0$-$C_6$ alkyl-C(O)$SR^{12}$, —$C_0$-$C_6$ alkyl-CONR$^{13}R^{14}$, —$C_0$-$C_6$ alkyl-COR$^{15}$, —$C_0$-$C_6$ alkyl-OCOR$^{15}$, —$C_0$-$C_6$ alkyl-OCONR$^{13}R^{14}$, —$C_0$-$C_6$ alkylNR$^{13}CONR^{13}R^{14}$, —$C_0$-$C_6$ alkyl-$NR^{13}COR^{15}$, —$C_0$-$C_6$ alkyl-Het, —$C_1$-$C_6$ alkyl-Ar and —$C_1$-$C_6$ alkyl-$C_3$-$C_7$ cycloalkyl, wherein said $C_1$-$C_6$ alkyl is optionally unsubstituted or substituted by one or more halo substituents;

Q is selected from $C_3$-$C_8$ cycloalkyl, Ar, and Het; wherein said $C_3$-$C_8$ cycloalkyl, Ar, and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl$CO_2R^{12}$, —$C_0$-$C_6$ alkyl-C(O)$SR^{12}$, —$C_0$-$C_6$ alkylCONR$^{13}R^{14}$, —$C_0$-$C_6$ alkyl-COR$^{15}$, —$C_0$-$C_6$ alkylNR$^{13}R^{14}$, —$C_0$-$C_6$ alkyl-$SR^{12}$, —$C_0$-$C_6$ alkyl-$OR^{12}$, —$C_0$-$C_6$ alkyl-$SO_3H$, —$C_0$-$C_6$ alkyl-$SO_2NR^{13}R^{14}$, —$C_0$-$C_6$ alkyl-$SO_2R^{12}$, —$C_0$-$C_6$ alkyl-$SOR^{15}$, —$C_0$-$C_6$ alkyl-OCOR$^{15}$, —$C_0$-$C_6$ alkyl-OC(O)$NR^{13}R^{14}$, —$C_0$-$C_6$ alkyl-OC(O)$OR^{15}$, —$C_0$-$C_6$ alkylNR$^{13}C(O)OR^{15}$, —$C_0$-$C_6$ alkyl-$NR^{13}C(O)NR^{13}R^{14}$, and —$C_0$-$C_6$ alkyl-$NR^{13}COR^{15}$, where said $C_1$-$C_6$ alkyl is optionally unsubstituted or substituted by one or more halo substituents;

p is 0-8;
n is 2-8;
m is 0 or 1;
q is 0 or 1;

each $R^1$ and $R^2$ are independently selected from H, halo, $C_1$-$C_6$ alkyl, $C_3$-$C_6$ alkenyl, $C_3$-$C_6$ alkynyl, —$C_0$-$C_6$ alkyl-$NR^{13}R^{14}$, —$C_0$-$C_6$ alkyl-$OR^{12}$, —$C_0$-$C_6$ alkyl-$SR^{12}$, —$C_1$-$C_6$ alkyl-Het, —$C_1$-$C_6$ alkyl-Ar, and —$C_1$-$C_6$ alkyl-$C_3$-$C_7$ cycloalkyl, or $R^1$ and $R^2$ together with the carbon to which they are attached form a 3-5 membered carbocyclic or heterocyclic ring, wherein said heterocyclic ring contains one, or more heteroatoms selected from N, O, and S, where any of said $C_1$-$C_6$ alkyl is optionally unsubstituted or substituted by one or more halo substituents;

each $R^3$ is the same or different and is independently selected from halo, cyano, nitro, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het, —$C_0$-$C_6$ alkyl-$C_3$-$C_7$ cycloalkyl, —$C_0$-$C_6$ alkyl-$CO_2R^{12}$, —$C_0$-$C_6$ alkyl-C(O)$SR^{12}$, —$C_0$-$C_6$ alkyl-CONR$^{13}R^{14}$, —$C_0$-$C_6$ alkyl-COR$^{15}$, —$C_0$-$C_6$ alkyl-$NR^{13}R^{14}$, —$C_0$-$C_6$ alkyl-$SR^{12}$, —$C_0$-$C_6$ alkyl-$OR^{12}$, —$C_0$-$C_6$ alkyl-$SO_3H$, —$C_0$-$C_6$ alkylSO$_2NR^{13}R^{14}$, —$C_0$-$C_6$ alkyl-$SO_2R^{12}$, —$C_0$-$C_6$ alkyl-$SOR^{15}$, —$C_0$-$C_6$ alkyl-OCOR$^{15}$, —$C_0$-$C_6$ alkyl-OC(O)$NR^{13}R^{14}$, —$C_0$-$C_6$ alkyl-OC(O)$OR^{15}$, —$C_0$-$C_6$ alkyl-$NR^{13}C(O)OR^{15}$, —$C_0$-$C_6$ alkyl-$NR^{13}C(O)NR^{13}R^{14}$, and —$C_0$-$C_6$ alkyl-$NR^{13}COR^{15}$, wherein said $C_1$-$C_6$ alkyl is optionally unsubstituted or substituted by one or more halo substituents;

each $R^4$ and $R^5$ is independently selected from H, halo, $C_1$-$C_6$ alkyl, —$C_0$-$C_6$ alkyl-Het, —$C_0$-$C_6$ alkyl-Ar, and —$C_0$-$C_6$ alkyl-$C_3$-$C_7$ cycloalkyl;

$R^6$ and $R^7$ are each independently selected from H, halo, $C_1$-$C_6$ alkyl, —$C_0$-$C_6$ alkyl-Het, —$C_0$-$C_6$ alkyl-Ar and —$C_0$-$C_6$ alkyl-$C_3$-$C_7$ cycloalkyl;

$R^8$ and $R^9$ are each independently selected from H, halo, $C_1$-$C_6$ alkyl, —$C_0$-$C_6$ alkyl-Het, —$C_0$-$C_6$ alkyl-Ar and —$C_0$-$C_6$ alkyl-$C_3$-$C_7$ cycloalkyl;

$R^{10}$ and $R^{11}$ are each independently selected from H, $C_1$-$C_{12}$ alkyl, $C_1$-$C_{12}$ alkenyl, $C_3$-$C_{12}$ alkynyl, —$C_0$-$C_8$ alkyl-Ar, —$C_0$-$C_8$ alkyl-Het, —$C_0$-$C_8$ alkyl-$C_3$-$C_7$ cycloalkyl, —$C_0$-$C_8$ alkyl-O—Ar, —$C_0$-$C_8$ alkyl-O-Het, —$C_0$-$C_8$ alkyl-O—$C_3$-$C_7$ cycloalkyl, —$C_0$-$C_8$ alkyl-S(O)$_x$—$C_0$-$C_8$ alkyl, —$C_0$-$C_8$ alkyl-S(O)$_x$—Ar, —$C_0$-$C_8$ alkyl-S(O)$_x$—Het, —$C_0$-$C_8$ alkyl-S(O)$_x$—$C_3$-$C_7$ cycloalkyl, —$C_0$-$C_8$ alkyl-NH—Ar, —$C_0$-$C_8$ alkyl-NH-Het, —$C_0$-$C_8$ alkyl-NH—$C_3$-$C_7$ cycloalkyl, —$C_0$-$C_8$ alkyl-N($C_1$-$C_4$ alkyl)-Ar, —$C_0$-$C_8$ alkyl-N($C_1$-$C_4$ alkyl)-Het, —$C_0$-$C_8$ alkyl-N($C_1$-$C_4$ alkyl)-$C_3$-$C_7$ cycloalkyl, —$C_0$-$C_8$ alkyl-Ar, —$C_0$-$C_8$ alkyl-Het, and —$C_0$-$C_8$ alkyl-$C_3$-$C_7$ cycloalkyl, where x is 0, 1, or 2, or $R^{10}$ and $R^{11}$, together with the nitrogen to which they are attached, form a 4-7 membered heterocyclic ring which optionally contains one or more additional heteroatoms selected from N, O, and S, wherein said $C_1$-$C_{12}$ alkyl, $C_3$-$C_{12}$ alkenyl, or $C_3$-$C_{12}$ alkynyl is optionally substituted by one or more of the substituents independently selected from the group halo, —OH, —SH, —$NH_2$, —NH(unsubstituted $C_1$-$C_6$ alkyl), —N(unsubstituted $C_1$-$C_6$ alkyl)(unsubstituted $C_1$-$C_6$ alkyl), unsubstituted —O$C_1$-$C_6$ alkyl, —$CO_2H$, —$CO_2$(unsubstituted $C_1$-$C_6$ alkyl), —$CONH_2$, —CONH(unsubstituted $C_1$-$C_6$ alkyl), —CON(unsubstituted $C_1$-$C_6$ alkyl)(unsubstituted $C_1$-$C_6$ alkyl), —$SO_3H$, —$SO_2NH_2$, —$SO_2NH$(unsubstituted $C_1$-$C_6$ alkyl) and —$SO_2N$(unsubstituted $C_1$-$C_6$ alkyl)(unsubstituted $C_1$-$C_6$ alkyl);

$R^{12}$ is selected from H, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het and —$C_0$-$C_6$ alkyl-$C_3$-$C_7$ cycloalkyl;

each $R^{13}$ and each $R^{14}$ are independently selected from H, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het, and —$C_0$-$C_6$ alkyl-$C_3$-$C_7$ cycloalkyl, or $R^{13}$ and $R^{14}$ together with the nitrogen to which they are attached form a 4-7 membered heterocyclic ring which optionally contains one or more additional heteroatoms selected from N, O, and S; and $R^{15}$ is selected from $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het, and —$C_0$-$C_6$ alkyl-$C_3$-$C_7$ cycloalkyl; and a lipophilic vehicle, comprising at least one lipophilic excipient in which the compound of formula II, or the pharmaceutically acceptable salt thereof, is soluble, wherein an amount of the compound of formula II, or a pharmaceutically acceptable salt thereof, in the formulation decreases by less than about 2% after storage for 1 week, 3 weeks, 3 months, or 6 months at a temperature of 40° C. and a relative humidity of 75%.

In an aspect, the invention features a formulation comprising:

a compound of formula II:

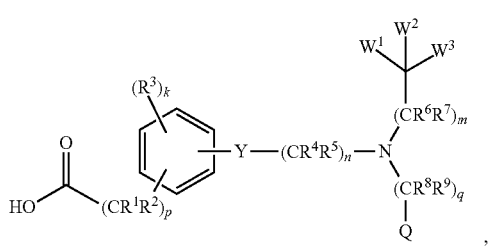

II or a pharmaceutically acceptable salt thereof,
wherein:

Y is selected from —O—, —S—, —N($R^{12}$)—, and —C($R^4$)($R^5$)—;

$W^1$ is selected from $C_1$-$C_6$ alkyl, $C_0$-$C_6$ alkyl, $C_3$-$C_6$ cycloalkyl, aryl and Het, wherein said $C_1$-$C_8$ alkyl, $C_3$-$C_8$ cycloalkyl, Ar and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl-$CO_2R^{12}$, —$C_0$-$C_6$ alkyl-C(O)$SR^{12}$, —$C_0$-$C_6$ alkyl-$CONR^{13}R^{14}$, —$C_0$-$C_6$ alkyl-$COR^{15}$, —$C_0$-$C_6$ alkyl-$NR^{13}R^{14}$, —$C_0$-$C_6$ alkyl-$SR^{12}$, —$C_0$-$C_6$ alkyl-$OR^{12}$, —$C_0$-$C_6$ alkyl-$SO_3H$, —$C_0$-$C_6$ alkyl-$SO_2NR^{13}R^{14}$, —$C_0$-$C_6$ alkyl-$SO_2R^{12}$, —$C_0$-$C_6$ alkyl-$SOR^{15}$, —$C_0$-$C_6$ alkyl$OCOR^{15}$, —$C_0$-$C_6$ alkyl-OC(O)$NR^{13}R^{14}$, —$C_0$-$C_6$ alkyl-OC(O)$OR^{15}$, —$C_0$-$C_6$ alkyl-$NR^{13}$C(O)$OR^{15}$, —$C_0$-$C_6$ alkyl-$NR^{13}$C(O)$NR^{13}R^{14}$, and —$C_0$-$C_6$ alkyl-$NR^{13}COR^{15}$, where said $C_1$-$C_6$ alkyl, is optionally unsubstituted or substituted by one or more halo substituents;

$W^2$ is selected from H, halo, $C_1$-$C_6$ alkyl, $C_2$-$C_6$ alkenyl, $C_2$-$C_6$ alkynyl, —$C_0$-$C_6$ alkyl-$NR^{13}R^{14}$, —$C_0$-$C_6$ alkyl-$SR^{12}$, —$C_0$-$C_6$ alkyl-$OR^{12}$, —$C_0$-$C_6$ alkyl$CO_2R^{12}$, —$C_0$-$C_6$ alkyl-C(O)$SR^{12}$, —$C_0$-$C_6$ alkyl$CONR^{13}R^{14}$, —$C_0$-$C_6$ alkyl-$COR^{15}$, —$C_0$-$C_6$ alkyl$OCOR^{15}$, —$C_0$-$C_6$ alkyl-$OCONR^{13}R^{14}$, —$C_0$-$C_6$ alkyl-$NR^{13}CONR^{13}R^{14}$, —$C_0$-$C_6$ alkyl-$NR^{13}COR^{15}$, —$C_0$-$C_6$ alkyl-Het, —$C_0$-$C_6$ alkyl-Ar, and —$C_0$-$C_6$ alkyl-$C_3$-$C_7$ cycloalkyl, wherein said $C_1$-$C_6$ alkyl is optionally unsubstituted or substituted by one or more halo substituents, and wherein the $C_3$-$C_7$ cycloalkyl, Ar and Het moieties of said —$C_0$-$C_6$ alkyl-Het, —$C_0$-$C_6$ alkyl-Ar and —$C_0$-$C_6$ alkyl-$C_3$-$C_7$ cycloalkyl are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl-$CO_2R^{12}$, —$C_0$-$C_6$ alkyl-C(O)$SR^{12}$, —$C_0$-$C_6$ alkyl-$CONR^{13}R^{14}$, —$C_0$-$C_6$ alkyl-$COR^{15}$, —$C_0$-$C_6$ alkyl-$NR^{13}R^{14}$, —$C_0$-$C_6$ alkyl-$SR^{12}$, —$C_0$-$C_6$ alkyl-$OR^{12}$, —$C_0$-$C_6$ alkyl-$SO_3H$, —$C_0$-$C_6$ alkyl-$SO_2NR^{13}R^{14}$, —$C_0$-$C_6$ alkyl-$SO_2R^{12}$, —$C_0$-$C_6$ alkyl-$SOR^{15}$, —$C_0$-$C_6$ alkyl-$OCOR^{15}$, —$C_0$-$C_6$ alkyl-OC(O)$NR^{13}R^{14}$, —$C_0$-$C_6$ alkyl-OC(O)$OR^{15}$, —$C_0$-$C_6$ alkyl-$NR^{13}C(O)OR^{15}$, —$C_0$-$C_6$ alkyl-$NR^{13}C(O)NR^{13}R^{14}$, and —$C_0$-$C_6$ alkyl-$NR^{13}COR^{15}$, where said $C_1$-$C_6$ alkyl, is optionally unsubstituted or substituted by one or more halo substituents;

$W^3$ is selected from the group consisting of: H, halo, $C_1$-$C_6$ alkyl, —$C_0$-$C_6$ alkyl-$NR^{13}R^{14}$, —$C_0$-$C_6$ alkyl$SR^{12}$, —$C_0$-$C_6$ alkyl-$OR^{12}$, —$C_0$-$C_6$ alkyl-$CO_2R^{12}$, —$C_0$-$C_6$ alkyl-C(O)$SR^{12}$, —$C_0$-$C_6$ alkyl-$CONR^{13}R^{14}$, —$C_0$-$C_6$ alkyl-$COR^{15}$, —$C_0$-$C_6$ alkyl-$OCOR^{15}$, —$C_0$-$C_6$ alkyl-$OCONR^{13}R^{14}$, —$C_0$-$C_6$ alkyl$NR^{13}CONR^{13}R^{14}$, —$C_0$-$C_6$ alkyl-$NR^{13}COR^{15}$, —$C_0$-$C_6$ alkyl-Het, —$C_1$-$C_6$ alkyl-Ar and —$C_1$-$C_6$ alkyl-$C_3$-$C_7$ cycloalkyl, wherein said $C_1$-$C_6$ alkyl is optionally unsubstituted or substituted by one or more halo substituents;

Q is selected from $C_3$-$C_8$ cycloalkyl, Ar, and Het; wherein said $C_3$-$C_8$ cycloalkyl, Ar, and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl$CO_2R^{12}$, —$C_0$-$C_6$ alkyl-C(O)$SR^{12}$, —$C_0$-$C_6$ alkyl$CONR^{13}R^{14}$, —$C_0$-$C_6$ alkyl-$COR^{15}$, —$C_0$-$C_6$ alkyl$NR^{13}R^{14}$, —$C_0$-$C_6$ alkyl-$SR^{12}$, —$C_0$-$C_6$ alkyl-$OR^{12}$, —$C_0$-$C_6$ alkyl-$SO_3H$, —$C_0$-$C_6$ alkyl-$SO_2NR^{13}R^{14}$, —$C_0$-$C_6$ alkyl-$SO_2R^{12}$, —$C_0$-$C_6$ alkyl-$SOR^{15}$, —$C_0$-$C_6$ alkyl-$OCOR^{15}$, —$C_0$-$C_6$ alkyl-OC(O)$NR^{13}R^{14}$, —$C_0$-$C_6$ alkyl-OC(O)$OR^{15}$, —$C_0$-$C_6$ alkyl$NR^{13}C(O)OR^{15}$, —$C_0$-$C_6$ alkyl-$NR^{13}C(O)NR^{13}R^{14}$, and —$C_0$-$C_6$ alkyl-$NR^{13}COR^{15}$, where said $C_1$-$C_6$ alkyl is optionally unsubstituted or substituted by one or more halo substituents;

p is 0-8;
n is 2-8;
m is 0 or 1;
q is 0 or 1;

each $R^1$ and $R^2$ are independently selected from H, halo, $C_1$-$C_6$ alkyl, $C_3$-$C_6$ alkenyl, $C_3$-$C_6$ alkynyl, —$C_0$-$C_6$ alkyl-$NR^{13}R^{14}$, —$C_0$-$C_6$ alkyl-$OR^{12}$, —$C_0$-$C_6$ alkyl-$SR^{12}$, —$C_1$-$C_6$ alkyl-Het, —$C_1$-$C_6$ alkyl-Ar, and —$C_1$-$C_6$ alkyl-$C_3$-$C_7$ cycloalkyl, or $R^1$ and $R^2$ together with the carbon to which they are attached form a 3-5 membered carbocyclic or heterocyclic ring, wherein said heterocyclic ring contains one, or more heteroatoms selected from N, O, and S, where any of said $C_1$-$C_6$ alkyl is optionally unsubstituted or substituted by one or more halo substituents;

each $R^3$ is the same or different and is independently selected from halo, cyano, nitro, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het, —$C_0$-$C_6$ alkyl-$C_3$-$C_7$ cycloalkyl, —$C_0$-$C_6$ alkyl-$CO_2R^{12}$, —$C_0$-$C_6$ alkyl-C(O)$SR^{12}$, —$C_0$-$C_6$ alkyl-$CONR^{13}R^{14}$, —$C_0$-$C_6$ alkyl-$COR^{15}$, —$C_0$-$C_6$ alkyl-$NR^{13}R^{14}$, —$C_0$-$C_6$ alkyl-$SR^{12}$, —$C_0$-$C_6$ alkyl-$OR^{12}$, —$C_0$-$C_6$ alkyl-$SO_3H$, —$C_0$-$C_6$ alkyl$SO_2NR^{13}R^{14}$, —$C_0$-$C_6$ alkyl-$SO_2R^{12}$, —$C_0$-$C_6$ alkyl-$SOR^{15}$, —$C_0$-$C_6$ alkyl-$OCOR^{15}$, —$C_0$-$C_6$ alkyl-OC(O)$NR^{13}R^{14}$, —$C_0$-$C_6$ alkyl-OC(O)$OR^{15}$, —$C_0$-$C_6$ alkyl-$NR^{13}C(O)OR^{15}$, —$C_0$-$C_6$ alkyl-$NR^{13}C(O)NR^{13}R^{14}$, and —$C_0$-$C_6$ alkyl-$NR^{13}COR^{15}$, wherein said $C_1$-$C_6$ alkyl is optionally unsubstituted or substituted by one or more halo substituents;

each $R^4$ and $R^5$ is independently selected from H, halo, $C_1$-$C_6$ alkyl, —$C_0$-$C_6$ alkyl-Het, —$C_0$-$C_6$ alkyl-Ar, and —$C_0$-$C_6$ alkyl-$C_3$-$C_7$ cycloalkyl;

$R^6$ and $R^7$ are each independently selected from H, halo, $C_1$-$C_6$ alkyl, —$C_0$-$C_6$ alkyl-Het, —$C_0$-$C_6$ alkyl-Ar and —$C_0$-$C_6$ alkyl-$C_3$-$C_7$ cycloalkyl;

$R^8$ and $R^9$ are each independently selected from H, halo, $C_1$-$C_6$ alkyl, —$C_0$-$C_6$ alkyl-Het, —$C_0$-$C_6$ alkyl-Ar and —$C_0$-$C_6$ alkyl-$C_3$-$C_7$ cycloalkyl;

$R^{10}$ and $R^{11}$ are each independently selected from H, $C_1$-$C_{12}$ alkyl, $C_3$-$C_{12}$ alkenyl, $C_3$-$C_{12}$ alkynyl, —$C_0$-$C_8$ alkyl-Ar, —$C_0$-$C_8$ alkyl-Het, —$C_0$-$C_8$ alkyl-$C_3$-$C_7$ cycloalkyl, —C$_0$-C$_8$ alkyl-O—Ar, —C$_0$-C$_8$ alkyl-O-Het, —C$_0$-C$_8$ alkyl-O—C$_3$-C$_7$ cycloalkyl, —C$_0$-C$_8$ alkyl-S(O)$_x$—C$_0$-C$_8$ alkyl, —C$_0$-C$_8$ alkyl-S(O)$_x$—Ar, —C$_0$-C$_8$ alkyl-S(O)$_x$—Het, —C$_0$-C$_8$ alkyl-S(O)$_x$—C$_3$-C$_7$ cycloalkyl, —C$_0$-C$_8$ alkyl-NH—Ar, —C$_0$-C$_8$ alkyl-NH-Het, —C$_0$-C$_8$ alkyl-NH—C$_3$-C$_7$ cycloalkyl, —C$_0$-C$_8$ alkyl-N(C$_1$-C$_4$ alkyl)-Ar, —C$_0$-C$_8$ alkyl-N(C$_1$-C$_4$ alkyl)-Het, —C$_0$-C$_8$ alkyl-N(C$_1$-C$_4$ alkyl-C$_3$-C$_7$ cycloalkyl, —C$_0$-C$_8$ alkyl-Ar, —C$_0$-C$_8$ alkyl-Het, and —C$_0$-C$_8$ alkyl-C$_3$-C$_7$ cycloalkyl, where x is 0, 1, or 2, or R$^{10}$ and R$^{11}$, together with the nitrogen to which they are attached, form a 4-7 membered heterocyclic ring which optionally contains one or more additional heteroatoms selected from N, O, and S, wherein said C$_1$-C$_{12}$ alkyl, C$_3$-C$_{12}$ alkenyl, or C$_3$-C$_{12}$ alkynyl is optionally substituted by one or more of the substituents independently selected from the group halo, —OH, —SH, —NH$_2$, —NH(unsubstituted C$_1$-C$_6$ alkyl), —N(unsubstituted C$_1$-C$_6$ alkyl)(unsubstituted C$_1$-C$_6$ alkyl), unsubstituted —OC$_1$-C$_6$ alkyl, —CO$_2$H, —CO$_2$(unsubstituted C$_1$-C$_6$ alkyl), —CONH$_2$, —CONH(unsubstituted C$_1$-C$_6$ alkyl), —CON(unsubstituted C$_1$-C$_6$ alkyl)(unsubstituted C$_1$-C$_6$ alkyl), —SO$_3$H, —SO$_2$NH$_2$, —SO$_2$NH(unsubstituted C$_1$-C$_6$ alkyl) and —SO$_2$N(unsubstituted C$_1$-C$_6$ alkyl)(unsubstituted C$_1$-C$_6$ alkyl);

R$^{12}$ is selected from H, C$_1$-C$_6$ alkyl, C$_3$-C$_6$ alkenyl, C$_3$-C$_6$ alkynyl, —C$_0$-C$_6$ alkyl-Ar, —C$_0$-C$_6$ alkyl-Het and —C$_0$-C$_6$ alkyl-C$_3$-C$_7$ cycloalkyl;

each R$^{13}$ and each R$^{14}$ are independently selected from H, C$_1$-C$_6$ alkyl, C$_3$-C$_6$ alkenyl, C$_3$-C$_6$ alkynyl, —C$_0$-C$_6$ alkyl-Ar, —C$_0$-C$_6$ alkyl-Het, and —C$_0$-C$_6$ alkyl-C$_3$-C$_7$ cycloalkyl, or R$^{13}$ and R$^{14}$ together with the nitrogen to which they are attached form a 4-7 membered heterocyclic ring which optionally contains one or more additional heteroatoms selected from N, O, and S; and R$^{15}$ is selected from C$_1$-C$_6$ alkyl, C$_3$-C$_6$ alkenyl, C$_3$-C$_6$ alkynyl, —C$_0$-C$_6$ alkyl-Ar, —C$_0$-C$_6$ alkyl-Het, and —C$_0$-C$_6$ alkyl-C$_3$-C$_7$ cycloalkyl; and a lipophilic vehicle, comprising at least one lipophilic excipient, in which the compound of formula II, or the pharmaceutically acceptable salt thereof, is soluble, wherein the lipophilic vehicle comprises at least one lipid excipient and at least one surfactant.

In some embodiments, the at least one lipophilic excipient comprises a lipid excipient. In some embodiments, the at least one lipophilic excipient comprises a surfactant. In some embodiments, the lipophilic vehicle comprises at least one lipid excipient and at least one surfactant. In some embodiments, the lipophilic vehicle content is at least 60% by weight, at least about 70% by weight, or at least about 80% by weight, of a total weight of the formulation.

In some embodiments, the formulation further includes a buffering agent, e.g., a weak base such as a lipid-soluble carboxylic acid salt. In some embodiments, the lipid-soluble carboxylic acid salt is at least one selected from the group consisting of a sodium, potassium, magnesium, and/or calcium salt of caprylic acid, capric acid, lauric acid, stearic acid, myristoleic acid, linoleic acid, linolenic acid, arachidonic acid, eicosenoic acid, palmitoleic acid, sapienic acid, oleic acid, elaidic acid, and/or vaccenic acid. In some embodiments, the formulation includes sodium oleate. In some embodiments, the lipid-soluble carboxylic acid salt (e.g., sodium oleate) content is about 1.1 molar equivalents to about 3 molar equivalents with respect to the compound of formula II or the pharmaceutically acceptable salt thereof.

In some embodiments, the pH of the formulation is from about pH 5 to about pH 7.

In some embodiments, the lipid excipient content of the lipophilic vehicle is about 40% by weight to about 80% by weight. In some embodiments, the lipid excipient comprises a monoglyceride, a diglyceride, and/or a triglyceride (e.g., at least one glycerol linoleate).

In some embodiments, the surfactant content of the lipophilic vehicle is about 20% by weight to about 60% by weight. In some embodiments, the surfactant content of the lipophilic vehicle is about 80% by weight to about 100% by weight. In some embodiments, the surfactant includes at least one polyglycolized glyceride, e.g., lauroyl macrogol-32 glyceride.

In some embodiments, the formulation further includes a stabilizing agent, e.g., an antioxidant such as at least one of sodium citrate, BHT (butylated hydroxytoluene), and BHA (butylated hydroxyanisole), or at least one of a TPGS compound (e.g., D-α-tocopheryl polyethylene glycol 1000 succinate) and EDTA (ethylenediaminetetraacetic acid).

In some embodiments, the compound of formula II is a hydrochloride salt.

In some embodiments, the compound of formula II is a fatty acid carboxylate salt (e.g., the oleate salt).

In some embodiments, the compound of formula II comprises Compound (I):

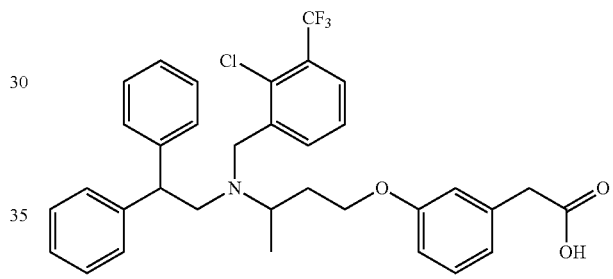

or a pharmaceutically acceptable salt thereof (e.g., the hydrochloride or oleate salt).

In some embodiments, the compound of formula II comprises Compound (II):

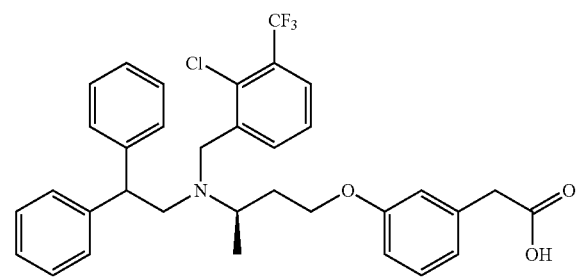 [SMILES: C[C@H](CCOc1cccc(CC(=O)O)c1)N(Cc1cccc(C(F)(F)F)c1Cl)CC(c1ccccc1)c1ccccc1]

or a pharmaceutically acceptable salt thereof (e.g., the hydrochloride or oleate salt).

In some embodiments, the formulation includes about 10 mg to about 200 mg, about 10 mg to about 100 mg, or about 10 mg to about 40 mg of the Compound (II), or the pharmaceutically acceptable salt thereof.

In some embodiments, the lipid excipient content of the lipophilic vehicle is about 40% by weight to about 80% by weight; the surfactant content of the lipophilic vehicle is about 20% by weight to about 60% by weight; and about 2% by weight of the formulation to about 10% by weight of the formulation is lipid-soluble carboxylic acid salt. In some embodiments, the formulation includes about 10 mg to about 40 mg of the Compound (II), or the pharmaceutically acceptable salt thereof. In some embodiments, the formulation further includes about 0.1% by weight to about 1% by weight EDTA; and/or about 0.1% by weight to about 1% by weight sodium citrate.

In some embodiments, the lipid excipient includes at least one glycerol fatty acid ester, e.g., glycerol linoleate. In some embodiments, the surfactant comprises at least one polyglycolized glyceride, e.g., lauroyl macrogol-32 glyceride. In some embodiments, the lipid-soluble carboxylic acid salt is sodium oleate.

In some embodiments, the compound of formula II, or the pharmaceutically acceptable salt thereof, is dissolved in the lipophilic vehicle.

In some embodiments, the formulation is self-emulsifying. In some embodiments, the formulation is a semi-solid suspension.

In an aspect, the invention features, a formulation produced by a method comprising:

mixing a lipophilic vehicle, comprising at least one lipophilic excipient, and a compound of formula II:

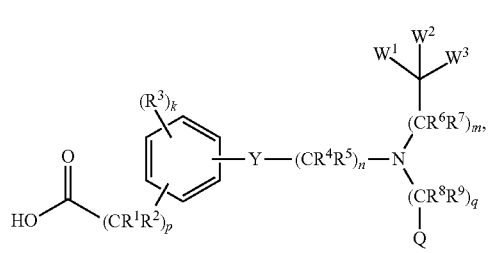

II or a pharmaceutically acceptable salt thereof,
wherein:
Y is selected from —O—, —S—, —N($R^{12}$)—, and —C($R^4$)($R^5$)—;
$W^1$ is selected from $C_1$-$C_6$ alkyl, $C_0$-$C_6$ alkyl, $C_3$-$C_6$ cycloalkyl, aryl and Het, wherein said $C_1$-$C_8$ alkyl, $C_3$-$C_8$ cycloalkyl, Ar and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl-$CO_2R^{12}$, —$C_0$-$C_6$ alkyl-C(O)$SR^{12}$, —$C_0$-$C_6$ alkyl-CON$R^{13}R^{14}$, —$C_0$-$C_6$ alkyl-$COR^{15}$, —$C_0$-$C_6$ alkyl-N$R^{13}R^{14}$, —$C_0$-$C_6$ alkyl-$SR^{12}$, —$C_0$-$C_6$ alkyl-$OR^{12}$, —$C_0$-$C_6$ alkyl-$SO_3H$, —$C_0$-$C_6$ alkyl-$SO_2NR^{13}R^{14}$, —$C_0$-$C_6$ alkyl-$SO_2R^{12}$, —$C_0$-$C_6$ alkyl-$SOR^{15}$, —$C_0$-$C_6$ alkylO$COR^{15}$, —$C_0$-$C_6$ alkyl-OC(O)$NR^{13}R^{14}$, —$C_0$-$C_6$ alkyl-OC(O)$OR^{15}$, —$C_0$-$C_6$ alkyl-$NR^{13}$C(O)$OR^{15}$, —$C_0$-$C_6$ alkyl-$NR^{13}$C(O)$NR^{13}R^{14}$, and —$C_0$-$C_6$ alkyl-$NR^{13}COR^{15}$, where said $C_1$-$C_6$ alkyl, is optionally unsubstituted or substituted by one or more halo substituents;
$W^2$ is selected from H, halo, $C_1$-$C_6$ alkyl, $C_2$-$C_6$ alkenyl, $C_2$-$C_6$ alkynyl, —$C_0$-$C_6$ alkyl-$NR^{13}R^{14}$, —$C_0$-$C_6$ alkyl-$SR^{12}$, —$C_0$-$C_6$ alkyl-$OR^{12}$, —$C_0$-$C_6$ alkyl$CO_2R^{12}$, —$C_0$-$C_6$ alkyl-C(O)$SR^{12}$, —$C_0$-$C_6$ alkylCON$R^{13}R^{14}$, —$C_0$-$C_6$ alkyl-$COR^{15}$, —$C_0$-$C_6$ alkylO$COR^{15}$, —$C_0$-$C_6$ alkyl-O$CONR^{13}R^{14}$, —$C_0$-$C_6$ alkyl-$NR^{13}CONR^{13}R^{14}$, —$C_0$-$C_6$ alkyl-$NR^{13}COR^{15}$, —$C_0$-$C_6$ alkyl-Het, —$C_0$-$C_6$ alkyl-Ar, and —$C_0$-$C_6$ alkyl-$C_3$-$C_7$ cycloalkyl, wherein said $C_1$-$C_6$ alkyl is optionally unsubstituted or substituted by one or more halo substituents, and wherein the $C_3$-$C_7$ cycloalkyl, Ar and Het moieties of said —$C_0$-$C_6$ alkyl-Het, —$C_0$-$C_6$ alkyl-Ar and —$C_0$-$C_6$ alkyl-$C_3$-$C_7$ cycloalkyl are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl-$CO_2R^{12}$, —$C_0$-$C_6$ alkyl-C(O)$SR^{12}$, —$C_0$-$C_6$ alkyl-$CONR^{13}R^{14}$, —$C_0$-$C_6$ alkyl-$COR^{15}$, —$C_0$-$C_6$ alkyl-$NR^{13}R^{14}$, —$C_0$-$C_6$ alkyl-$SR^{12}$, —$C_0$-$C_6$ alkyl-$OR^{12}$, —$C_0$-$C_6$ alkyl-$SO_3H$, —$C_0$-$C_6$ alkyl-$SO_2NR^{13}R^{14}$, —$C_0$-$C_6$ alkyl-$SO_2R^{12}$, —$C_0$-$C_6$ alkyl-$SOR^{15}$, —$C_0$-$C_6$ alkyl-$OCOR^{15}$, —$C_0$-$C_6$ alkyl-OC(O)$NR^{13}R^{14}$, —$C_0$-$C_6$ alkyl-OC(O)$OR^{15}$, —$C_0$-$C_6$ alkyl-$NR^{13}C(O)OR^{15}$, —$C_0$-$C_6$ alkyl-$NR^{13}C(O)NR^{13}R^{14}$, and —$C_0$-$C_6$ alkyl-$NR^{13}COR^{15}$, where said $C_1$-$C_6$ alkyl, is optionally unsubstituted or substituted by one or more halo substituents;
$W^3$ is selected from the group consisting of: H, halo, $C_1$-$C_6$ alkyl, —$C_0$-$C_6$ alkyl-$NR^{13}R^{14}$, —$C_0$-$C_6$ alkyl$SR^{12}$, —$C_0$-$C_6$ alkyl-$OR^{12}$, —$C_0$-$C_6$ alkyl-$CO_2R^{12}$, —$C_0$-$C_6$ alkyl-C(O)$SR^{12}$, —$C_0$-$C_6$ alkyl-$CONR^{13}R^{14}$, —$C_0$-$C_6$ alkyl-$COR^{15}$, —$C_0$-$C_6$ alkyl-$OCOR^{15}$, —$C_0$-$C_6$ alkyl-$OCONR^{13}R^{14}$, —$C_0$-$C_6$ alkyl$NR^{13}CONR^{13}R^{14}$, —$C_0$-$C_6$ alkyl-$NR^{13}COR^{15}$, —$C_0$-$C_6$ alkyl-Het, —$C_1$-$C_6$ alkyl-Ar and —$C_1$-$C_6$ alkyl-$C_3$-$C_7$ cycloalkyl, wherein said $C_1$-$C_6$ alkyl is optionally unsubstituted or substituted by one or more halo substituents;
Q is selected from $C_3$-$C_8$ cycloalkyl, Ar, and Het; wherein said $C_3$-$C_8$ cycloalkyl, Ar, and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl$CO_2R^{12}$, —$C_0$-$C_6$ alkyl-C(O)$SR^{12}$, —$C_0$-$C_6$ alkyl$CONR^{13}R^{14}$, —$C_0$-$C_6$ alkyl-$COR^{15}$, —$C_0$-$C_6$ alkyl$NR^{13}R^{14}$, —$C_0$-$C_6$ alkyl-$SR^{12}$, —$C_0$-$C_6$ alkyl-$OR^{12}$, —$C_0$-$C_6$ alkyl-$SO_3H$, —$C_0$-$C_6$ alkyl-$SO_2NR^{13}R^{14}$, —$C_0$-$C_6$ alkyl-$SO_2R^{12}$, —$C_0$-$C_6$ alkyl-$SOR^{15}$, —$C_0$-$C_6$ alkyl-$OCOR^{15}$, —$C_0$-$C_6$ alkyl-OC(O)$NR^{13}R^{14}$, —$C_0$-$C_6$ alkyl-OC(O)$OR^{15}$, —$C_0$-$C_6$ alkyl$NR^{13}C(O)OR^{15}$, —$C_0$-$C_6$ alkyl-$NR^{13}C(O)NR^{13}R^{14}$, and —$C_0$-$C_6$ alkyl-$NR^{13}COR^{15}$, where said $C_1$-$C_6$ alkyl is optionally unsubstituted or substituted by one or more halo substituents;
p is 0-8;
n is 2-8;
m is 0 or 1;
q is 0 or 1;
each $R^1$ and $R^2$ are independently selected from H, halo, $C_1$-$C_6$ alkyl, $C_3$-$C_6$ alkenyl, $C_3$-$C_6$ alkynyl, —$C_0$-$C_6$ alkyl-$NR^{13}R^{14}$, —$C_0$-$C_6$ alkyl-$OR^{12}$, —$C_0$-$C_6$ alkyl-$SR^{12}$, —$C_1$-$C_6$ alkyl-Het, —$C_1$-$C_6$ alkyl-Ar, and —$C_1$-$C_6$ alkyl-$C_3$-$C_7$ cycloalkyl, or $R^1$ and $R^2$ together with the carbon to which they are attached form a 3-5 membered carbocyclic or heterocyclic ring, wherein said heterocyclic ring contains one, or more heteroatoms selected from N, O, and S, where any of said $C_1$-$C_6$ alkyl is optionally unsubstituted or substituted by one or more halo substituents;
each $R^3$ is the same or different and is independently selected from halo, cyano, nitro, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het, —$C_0$-$C_6$ alkyl-$C_3$-$C_7$ cycloalkyl, —$C_0$-$C_6$ alkyl-$CO_2R^{12}$, —$C_0$-$C_6$ alkyl-C(O)$SR^{12}$, —$C_0$-$C_6$ alkyl-$CONR^{13}R^{14}$, —$C_0$-$C_6$ alkyl-$COR^{15}$, —$C_0$-$C_6$ alkyl-$NR^{13}R^{14}$, —$C_0$-$C_6$ alkyl-$SR^{12}$, —$C_0$-$C_6$ alkyl-$OR^{12}$, —$C_0$-$C_6$ alkyl-$SO_3H$, —$C_0$-$C_6$ alkyl$SO_2NR^{13}R^{14}$, —$C_0$-$C_6$ alkyl-$SO_2R^{12}$, —$C_0$-$C_6$ alkyl-$SOR^{15}$, —$C_0$-$C_6$ alkyl-$OCOR^{15}$, —$C_0$-$C_6$ alkyl-OC(O)$NR^{13}R^{14}$, —$C_0$-$C_6$ alkyl-OC(O)$OR^{15}$, —$C_0$-$C_6$ alkyl-$NR^{13}C(O)OR^{15}$, —$C_0$-$C_6$ alkyl-$NR^{13}C(O)NR^{13}R^{14}$, and —$C_0$-$C_6$ alkyl-$NR^{13}COR^{15}$, wherein said $C_1$-$C_6$ alkyl is optionally unsubstituted or substituted by one or more halo substituents;

each $R^4$ and $R^5$ is independently selected from H, halo, $C_1$-$C_6$ alkyl, —$C_0$-$C_6$ alkyl-Het, —$C_0$-$C_6$ alkyl-Ar, and —$C_0$-$C_6$ alkyl-$C_3$-$C_7$ cycloalkyl;

$R^6$ and $R^7$ are each independently selected from H, halo, $C_1$-$C_6$ alkyl, —$C_0$-$C_6$ alkyl-Het, —$C_0$-$C_6$ alkyl-Ar and —$C_0$-$C_6$ alkyl-$C_3$-$C_7$ cycloalkyl;

$R^8$ and $R^9$ are each independently selected from H, halo, $C_1$-$C_6$ alkyl, —$C_0$-$C_6$ alkyl-Het, —$C_0$-$C_6$ alkyl-Ar and —$C_0$-$C_6$ alkyl-$C_3$-$C_7$ cycloalkyl;

$R^{10}$ and $R^{11}$ are each independently selected from H, $C_1$-$C_{12}$ alkyl, $C_3$-$C_{12}$ alkenyl, $C_3$-$C_{12}$ alkynyl, —$C_0$-$C_8$ alkyl-Ar, —$C_0$-$C_8$ alkyl-Het, —$C_0$-$C_8$ alkyl-$C_3$-$C_7$ cycloalkyl, —$C_0$-$C_8$ alkyl-O—Ar, —$C_0$-$C_8$ alkyl-O-Het, —$C_0$-$C_8$ alkyl-O—$C_3$-$C_7$ cycloalkyl, —$C_0$-$C_8$ alkyl-S(O)$_x$—$C_0$-$C_8$ alkyl, —$C_0$-$C_8$ alkyl-S(O)$_x$—Ar, —$C_0$-$C_8$ alkyl-S(O)$_x$-Het, —$C_0$-$C_8$ alkyl-S(O)$_x$—$C_3$-$C_7$ cycloalkyl, —$C_0$-$C_8$ alkyl-NH—Ar, —$C_0$-$C_8$ alkyl-NH-Het, —$C_0$-$C_8$ alkyl-NH—$C_3$-$C_7$ cycloalkyl, —$C_0$-$C_8$ alkyl-N($C_1$-$C_4$ alkyl)-Ar, —$C_0$-$C_8$ alkyl-N($C_1$-$C_4$ alkyl)-Het, —$C_0$-$C_8$ alkyl-N($C_1$-$C_4$ alkyl)-$C_3$-$C_7$ cycloalkyl, —$C_0$-$C_8$ alkyl-Ar, —$C_0$-$C_8$ alkyl-Het, and —$C_0$-$C_8$ alkyl-$C_3$-$C_7$ cycloalkyl, where x is 0, 1, or 2, or $R^{10}$ and $R^{11}$, together with the nitrogen to which they are attached, form a 4-7 membered heterocyclic ring which optionally contains one or more additional heteroatoms selected from N, O, and S, wherein said $C_1$-$C_{12}$ alkyl, $C_3$-$C_{12}$ alkenyl, or $C_3$-$C_{12}$ alkynyl is optionally substituted by one or more of the substituents independently selected from the group halo, —OH, —SH, —$NH_2$, —NH(unsubstituted $C_1$-$C_6$ alkyl), —N(unsubstituted $C_1$-$C_6$ alkyl)(unsubstituted $C_1$-$C_6$ alkyl), unsubstituted —O$C_1$-$C_6$ alkyl, —$CO_2$H, —$CO_2$(unsubstituted $C_1$-$C_6$ alkyl), —$CONH_2$, —CONH(unsubstituted $C_1$-$C_6$ alkyl), —CON(unsubstituted $C_1$-$C_6$ alkyl)(unsubstituted $C_1$-$C_6$ alkyl), —$SO_3$H, —$SO_2NH_2$, —$SO_2$NH(unsubstituted $C_1$-$C_6$ alkyl) and —$SO_2$N(unsubstituted $C_1$-$C_6$ alkyl)(unsubstituted $C_1$-$C_6$ alkyl);

$R^{12}$ is selected from H, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het and —$C_0$-$C_6$ alkyl-$C_3$-$C_7$ cycloalkyl;

each $R^{13}$ and each $R^{14}$ are independently selected from H, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het, and —$C_0$-$C_6$ alkyl-$C_3$-$C_7$ cycloalkyl, or $R^{13}$ and $R^{14}$ together with the nitrogen to which they are attached form a 4-7 membered heterocyclic ring which optionally contains one or more additional heteroatoms selected from N, O, and S; and $R^{15}$ is selected from $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het, and —$C_0$-$C_6$ alkyl-$C_3$-$C_7$ cycloalkyl.

In some embodiments, the method comprises dissolving the compound of formula II, or the pharmaceutically acceptable salt thereof, in the lipophilic vehicle. In some embodiments, the method further includes adding a sodium salt of a fatty acid. In some embodiments, the sodium salt of the fatty acid is added to the lipophilic vehicle before the compound of formula II, or the pharmaceutically acceptable salt thereof. In some embodiments, the sodium chloride precipitates upon addition of the sodium salt of the fatty acid. In some embodiments, the method further comprises adding a stabilizing agent. In some embodiments, the compound is:

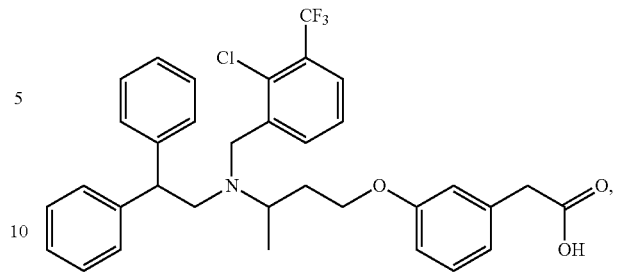

or a pharmaceutically acceptable salt thereof (e.g., the hydrochloride salt).

In some embodiments, the lipophilic vehicle includes at least one glycerol fatty acid ester, e.g., glycerol linoleate. In some embodiments, the lipophilic vehicle comprises at least one polyglycolized glyceride, e.g., lauroyl macrogol-32 glyceride. In some embodiments, the stabilizing agent comprises EDTA and/or sodium citrate.

In an aspect, the invention features capsule that contains any of the foregoing formulations. In some embodiments, the capsule is a gelatin capsule (e.g., a hard gelatin capsule or a soft gelatin capsule), an HPMC (hydroxypropyl methylcellulose) capsule, or a non-gelatin soft shell capsule.

In an aspect, the invention features a method of treatment including administering any of the foregoing formulations or capsules.

In an aspect, the invention features a method of treating a cancer, e.g., ovarian cancer, breast cancer, lung cancer, glioblastoma, melanoma, bladder cancer, head and neck cancer, renal cell cancer, colorectal cancer, lymphoma, leukemia, multiple myeloma, hepatocellular carcinoma, a high grade neuroendocrine tumor and/or a small cell carcinoma such as a lung cancer. This method includes administering to a subject in need thereof any of the foregoing formulations or capsules, which comprises a therapeutically effective amount of the Compound (II), or the pharmaceutically acceptable salt thereof. In some embodiments, any of the foregoing pharmaceutically acceptable salts, formulations, or capsules have improved properties compared with other salts or formulations of compounds of formula II. For example, in some embodiments, any of the foregoing pharmaceutically acceptable salts, formulations, or capsules have increased stability (e.g., a reduction in the loss of the compound of formula II to degradation in the formulation after storage for about 3 months, 6 months, or 2 years at 40° C. and 75% relative humidity in comparison to formulations of the compound without a self-emulsifying lipid vehicle or without a fatty acid salt form) and/or increased oral bioavailability (e.g., bioavailability (e.g., $F_{abs}$ or $F_{rel}$) in comparison to formulations of the compound without a self-emulsifying lipid vehicle or without a fatty acid salt form. In some embodiments, any of the foregoing pharmaceutically acceptable salts, formulations, or capsules have improved bioavailability (e.g., $F_{abs}$ or $F_{rel}$) compared to the hydrochloride salt of a compound of formula II formulated as described in Collins et al. "Identification of a nonsteroidal liver X receptor agonist through parallel array synthesis of tertiary amines" J. Med. Chem., 2002, 45:1963-1966, the formulation methods of which are incorporated herein by reference. In some embodiments, the formulation has increased bioavailability upon oral administration compared with a formulation comprising a structure of formula I that does not comprise the lipophilic vehicle.

Further features of the present invention will be even more apparent from the following description and the appended claims.

DETAILED DESCRIPTION

It has now been found that compounds such as those of formula II, which can be LXR modulators, present particular formulation challenges. These challenges pertain to the stability of the formulation and systemic bioavailability upon administration, and oral administration in particular. For instance, these compounds, or their pharmaceutically acceptable salts, can be considerably acidic (e.g., forming solutions of about pH 1). This can lead to degradation reactions occurring between the active compound and excipient(s) and other components of the formulation, which can lead to instability, degradation, and/or reduced systemic bioavailability and, as a result, negatively impact efficacy. The present invention provides formulations of compounds of formula II (and pharmaceutically acceptable salts thereof) with improved stability that help to mitigate these problems. In some embodiments, the pharmaceutically acceptable salts and formulations of the invention have improved properties compared with other salts or formulations of compounds of formula II. For example, in some embodiments, the pharmaceutically acceptable salts or formulations of the invention have increased stability and/or increased bioavailability.

In one aspect, the present invention provides a formulation comprising a compound of formula II:

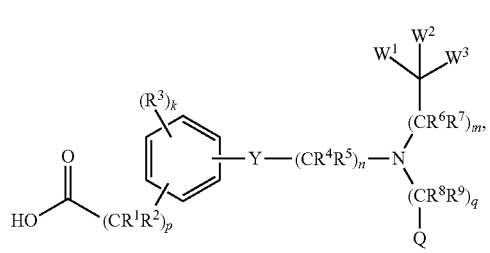

II or a pharmaceutically acceptable salt thereof,
wherein:
Y is selected from —O—, —S—, —N($R^{12}$)—, and —C($R^4$)($R^5$)—;

$W^1$ is selected from $C_1$-$C_6$ alkyl, $C_0$-$C_6$ alkyl, $C_3$-$C_6$ cycloalkyl, aryl and Het, wherein said $C_1$-$C_8$ alkyl, $C_3$-$C_8$ cycloalkyl, Ar and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl-$CO_2R^{12}$, —$C_0$-$C_6$ alkyl-C(O)$SR^{12}$, —$C_0$-$C_6$ alkyl-$CONR^{13}R^{14}$, —$C_0$-$C_6$ alkyl-$COR^{15}$, —$C_0$-$C_6$ alkyl-$NR^{13}R^{14}$, —$C_0$-$C_6$ alkyl-$SR^{12}$, —$C_0$-$C_6$ alkyl-$OR^{12}$, —$C_0$-$C_6$ alkyl-$SO_3H$, —$C_0$-$C_6$ alkyl-$SO_2NR^{13}R^{14}$, —$C_0$-$C_6$ alkyl-$SO_2R^{12}$, —$C_0$-$C_6$ alkyl-$SOR^{15}$, —$C_0$-$C_6$ alkylO$COR^{15}$, —$C_0$-$C_6$ alkyl-OC(O)$NR^{13}R^{14}$, —$C_0$-$C_6$ alkyl-OC(O)$OR^{15}$, —$C_0$-$C_6$ alkyl-$NR^{13}$C(O)$OR^{15}$, —$C_0$-$C_6$ alkyl-$NR^{13}$C(O)$NR^{13}R^{14}$, and —$C_0$-$C_6$ alkyl-$NR^{13}COR^{15}$, where said $C_1$-$C_6$ alkyl, is optionally unsubstituted or substituted by one or more halo substituents;

$W^2$ is selected from H, halo, $C_1$-$C_6$ alkyl, $C_2$-$C_6$ alkenyl, $C_2$-$C_6$ alkynyl, —$C_0$-$C_6$ alkyl-$NR^{13}R^{14}$, —$C_0$-$C_6$ alkyl-$SR^{12}$, —$C_0$-$C_6$ alkyl-$OR^{12}$, —$C_0$-$C_6$ alkyl$CO_2R^{12}$, —$C_0$-$C_6$ alkyl-C(O)$SR^{12}$, —$C_0$-$C_6$ alkyl$CONR^{13}R^{14}$, —$C_0$-$C_6$ alkyl-$COR^{15}$, —$C_0$-$C_6$ alkylO$COR^{15}$, —$C_0$-$C_6$ alkyl-O$CONR^{13}R^{14}$, —$C_0$-$C_6$ alkyl-$NR^{13}CONR^{13}R^{14}$, —$C_0$-$C_6$ alkyl-$NR^{13}COR^{15}$, —$C_0$-$C_6$ alkyl-Het, —$C_0$-$C_6$ alkyl-Ar, and —$C_0$-$C_6$ alkyl-$C_3$-$C_7$ cycloalkyl, wherein said $C_1$-$C_6$ alkyl is optionally unsubstituted or substituted by one or more halo substituents, and wherein the $C_3$-$C_7$ cycloalkyl, Ar and Het moieties of said —$C_0$-$C_6$ alkyl-Het, —$C_0$-$C_6$ alkyl-Ar and —$C_0$-$C_6$ alkyl-$C_3$-$C_7$ cycloalkyl are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl-$CO_2R^{12}$, —$C_0$-$C_6$ alkyl-C(O)$SR^{12}$, —$C_0$-$C_6$ alkyl-$CONR^{13}R^{14}$, —$C_0$-$C_6$ alkyl-$COR^{15}$, —$C_0$-$C_6$ alkyl-$NR^{13}R^{14}$, —$C_0$-$C_6$ alkyl-$SR^{12}$, —$C_0$-$C_6$ alkyl-$OR^{12}$, —$C_0$-$C_6$ alkyl-$SO_3H$, —$C_0$-$C_6$ alkyl-$SO_2NR^{13}R^{14}$, —$C_0$-$C_6$ alkyl-$SO_2R^{12}$, —$C_0$-$C_6$ alkyl-$SOR^{15}$, —$C_0$-$C_6$ alkyl-O$COR^{15}$, —$C_0$-$C_6$ alkyl-OC(O)$NR^{13}R^{14}$, —$C_0$-$C_6$ alkyl-OC(O)$OR^{15}$, —$C_0$-$C_6$ alkyl-$NR^{13}C(O)OR^{15}$, —$C_0$-$C_6$ alkyl-$NR^{13}C(O)NR^{13}R^{14}$, and —$C_0$-$C_6$ alkyl-$NR^{13}COR^{15}$, where said $C_1$-$C_6$ alkyl, is optionally unsubstituted or substituted by one or more halo substituents;

$W^3$ is selected from the group consisting of: H, halo, $C_1$-$C_6$ alkyl, —$C_0$-$C_6$ alkyl-$NR^{13}R^{14}$, —$C_0$-$C_6$ alkyl$SR^{12}$, —$C_0$-$C_6$ alkyl-$OR^{12}$, —$C_0$-$C_6$ alkyl-$CO_2R^{12}$, —$C_0$-$C_6$ alkyl-C(O)$SR^{12}$, —$C_0$-$C_6$ alkyl-$CONR^{13}R^{14}$, —$C_0$-$C_6$ alkyl-$COR^{15}$, —$C_0$-$C_6$ alkyl-O$COR^{15}$, —$C_0$-$C_6$ alkyl-O$CONR^{13}R^{14}$, —$C_0$-$C_6$ alkyl$NR^{13}CONR^{13}R^{14}$, —$C_0$-$C_6$ alkyl-$NR^{13}COR^{15}$, —$C_0$-$C_6$ alkyl-Het, —$C_1$-$C_6$ alkyl-Ar and —$C_1$-$C_6$ alkyl-$C_3$-$C_7$ cycloalkyl, wherein said $C_1$-$C_6$ alkyl is optionally unsubstituted or substituted by one or more halo substituents;

Q is selected from $C_3$-$C_8$ cycloalkyl, Ar, and Het; wherein said $C_3$-$C_8$ cycloalkyl, Ar, and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl$CO_2R^{12}$, —$C_0$-$C_6$ alkyl-C(O)$SR^{12}$, —$C_0$-$C_6$ alkyl$CONR^{13}R^{14}$, —$C_0$-$C_6$ alkyl-$COR^{15}$, —$C_0$-$C_6$ alkyl$NR^{13}R^{14}$, —$C_0$-$C_6$ alkyl-$SR^{12}$, —$C_0$-$C_6$ alkyl-$OR^{12}$, —$C_0$-$C_6$ alkyl-$SO_3H$, —$C_0$-$C_6$ alkyl-$SO_2NR^{13}R^{14}$, —$C_0$-$C_6$ alkyl-$SO_2R^{12}$, —$C_0$-$C_6$ alkyl-$SOR^{15}$, —$C_0$-$C_6$ alkyl-O$COR^{15}$, —$C_0$-$C_6$ alkyl-OC(O)$NR^{13}R^{14}$, —$C_0$-$C_6$ alkyl-OC(O)$OR^{15}$, —$C_0$-$C_6$ alkyl$NR^{13}C(O)OR^{15}$, —$C_0$-$C_6$ alkyl-$NR^{13}C(O)NR^{13}R^{14}$, and —$C_0$-$C_6$ alkyl-$NR^{13}COR^{15}$, where said $C_1$-$C_6$ alkyl is optionally unsubstituted or substituted by one or more halo substituents;

p is 0-8;
n is 2-8;
m is 0 or 1;
q is 0 or 1;
each $R^1$ and $R^2$ are independently selected from H, halo, $C_1$-$C_6$ alkyl, $C_3$-$C_6$ alkenyl, $C_3$-$C_6$ alkynyl, —$C_0$-$C_6$ alkyl-$NR^{13}R^{14}$, —$C_0$-$C_6$ alkyl-$OR^{12}$, —$C_0$-$C_6$ alkyl-$SR^{12}$, —$C_1$-$C_6$ alkyl-Het, —$C_1$-$C_6$ alkyl-Ar, and —$C_1$-$C_6$ alkyl-$C_3$-$C_7$ cycloalkyl, or $R^1$ and $R^2$ together with the carbon to which they are attached form a 3-5 membered carbocyclic or heterocyclic ring, wherein said heterocyclic ring contains one, or more heteroatoms selected from N, O, and S, where any of said $C_1$-$C_6$ alkyl is optionally unsubstituted or substituted by one or more halo substituents; each $R^3$ is the same or different and is independently selected from halo, cyano, nitro, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het, —$C_0$-$C_6$ alkyl-$C_3$-$C_7$ cycloalkyl, —$C_0$-$C_6$ alkyl-$CO_2R^{12}$, —$C_0$-$C_6$ alkyl-C(O)$SR^{12}$, —$C_0$-$C_6$ alkyl-$CONR^{13}R^{14}$, —$C_0$-$C_6$ alkyl-$COR^{15}$, —$C_0$-$C_6$ alkyl-$NR^{13}R^{14}$, —$C_0$-$C_6$ alkyl-$SR^{12}$, —$C_0$-$C_6$ alkyl-$OR^{12}$, —$C_0$-$C_6$ alkyl-$SO_3H$, —$C_0$-$C_6$ alkylSO$_2NR^{13}R^{14}$, —$C_0$-$C_6$ alkyl-$SO_2R^{12}$, —$C_0$-$C_6$ alkylSO$R^{15}$, —$C_0$-$C_6$ alkyl-O$COR^{15}$, —$C_0$-$C_6$ alkyl-OC(O)$NR^{13}R^{14}$, —$C_0$-$C_6$ alkyl-OC(O)$OR^{15}$, —$C_0$-$C_6$ alkyl-$NR^{13}C(O)OR^{15}$, —$C_0$-$C_6$ alkyl-NR$^{13}$C(O)NR$^{13}$R$^{14}$, and —C$_0$-C$_6$ alkyl-NR$^{13}$COR$^{15}$, wherein said C$_1$-C$_6$ alkyl is optionally unsubstituted or substituted by one or more halo substituents;

each R$^4$ and R$^5$ is independently selected from H, halo, C$_1$-C$_6$ alkyl, —C$_0$-C$_6$ alkyl-Het, —C$_0$-C$_6$ alkyl-Ar, and —C$_0$-C$_6$ alkyl-C$_3$-C$_7$ cycloalkyl; R$^6$ and R$^7$ are each independently selected from H, halo, C$_1$-C$_6$ alkyl, —C$_0$-C$_6$ alkyl-Het, —C$_0$-C$_6$ alkyl-Ar and —C$_0$-C$_6$ alkyl-C$_3$-C$_7$ cycloalkyl; R$^8$ and R$^9$ are each independently selected from H, halo, C$_1$-C$_6$ alkyl, —C$_0$-C$_6$ alkyl-Het, —C$_0$-C$_6$ alkyl-Ar and —C$_0$-C$_6$ alkyl-C$_3$-C$_7$ cycloalkyl;

R$^{10}$ and R$^{11}$ are each independently selected from H, C$_1$-C$_{12}$ alkyl, C$_3$-C$_{12}$ alkenyl, C$_3$-C$_{12}$ alkynyl, —C$_0$-C$_8$ alkyl-Ar, —C$_0$-C$_8$ alkyl-Het, —C$_0$-C$_8$ alkyl-C$_3$-C$_7$ cycloalkyl, —C$_0$-C$_8$ alkyl-O—Ar, —C$_0$-C$_8$ alkyl-O-Het, —C$_0$-C$_8$ alkyl-O—C$_3$-C$_7$ cycloalkyl, —C$_0$-C$_8$ alkyl-S(O)$_x$—C$_0$-C$_8$ alkyl, —C$_0$-C$_8$ alkyl-S(O)$_x$—Ar, —C$_0$-C$_8$ alkyl-S(O)$_x$-Het, —C$_0$-C$_8$ alkyl-S(O)$_x$—C$_3$-C$_7$ cycloalkyl, —C$_0$-C$_8$ alkyl-NH—Ar, —C$_0$-C$_8$ alkyl-NH-Het, —C$_0$-C$_8$ alkyl-NH—C$_3$-C$_7$ cycloalkyl, —C$_0$-C$_8$ alkyl-N(C$_1$-C$_4$ alkyl)-Ar, —C$_0$-C$_8$ alkyl-N(C$_1$-C$_4$ alkyl)-Het, —C$_0$-C$_8$ alkyl-N(C$_1$-C$_4$ alkyl-C$_3$-C$_7$ cycloalkyl, —C$_0$-C$_8$ alkyl-Ar, —C$_0$-C$_8$ alkyl-Het, and —C$_0$-C$_8$ alkyl-C$_3$-C$_7$ cycloalkyl, where x is 0, 1, or 2, or R$^{10}$ and R$^{11}$, together with the nitrogen to which they are attached, form a 4-7 membered heterocyclic ring which optionally contains one or more additional heteroatoms selected from N, O, and S, wherein said C$_1$-C$_{12}$ alkyl, C$_3$-C$_{12}$ alkenyl, or C$_3$-C$_{12}$ alkynyl is optionally substituted by one or more of the substituents independently selected from the group halo, —OH, —SH, —NH$_2$, —NH(unsubstituted C$_1$-C$_6$ alkyl), —N(unsubstituted C$_1$-C$_6$ alkyl)(unsubstituted C$_1$-C$_6$ alkyl), unsubstituted —OC$_1$-C$_6$ alkyl, —CO$_2$H, —CO$_2$(unsubstituted C$_1$-C$_6$ alkyl), —CONH$_2$, —CONH(unsubstituted C$_1$-C$_6$ alkyl), —CON(unsubstituted C$_1$-C$_6$ alkyl)(unsubstituted C$_1$-C$_6$ alkyl), —SO$_3$H, —SO$_2$NH$_2$, —SO$_2$NH(unsubstituted C$_1$-C$_6$ alkyl) and —SO$_2$N(unsubstituted C$_1$-C$_6$ alkyl)(unsubstituted C$_1$-C$_6$ alkyl);

R$^{12}$ is selected from H, C$_1$-C$_6$ alkyl, C$_3$-C$_6$ alkenyl, C$_3$-C$_6$ alkynyl, —C$_0$-C$_6$ alkyl-Ar, —C$_0$-C$_6$ alkyl-Het and —C$_0$-C$_6$ alkyl-C$_3$-C$_7$ cycloalkyl;

each R$^{13}$ and each R$^{14}$ are independently selected from H, C$_1$-C$_6$ alkyl, C$_3$-C$_6$ alkenyl, C$_3$-C$_6$ alkynyl, —C$_0$-C$_6$ alkyl-Ar, —C$_0$-C$_6$ alkyl-Het, and —C$_0$-C$_6$ alkyl-C$_3$-C$_7$ cycloalkyl, or R$^{13}$ and R$^{14}$ together with the nitrogen to which they are attached form a 4-7 membered heterocyclic ring which optionally contains one or more additional heteroatoms selected from N, O, and S; and R$^{15}$ is selected from C$_1$-C$_6$ alkyl, C$_3$-C$_6$ alkenyl, C$_3$-C$_6$ alkynyl, —C$_0$-C$_6$ alkyl-Ar, —C$_0$-C$_6$ alkyl-Het, and —C$_0$-C$_6$ alkyl-C$_3$-C$_7$ cycloalkyl.

Compounds of formula II can be synthesized by methods known in the art, e.g., as described in U.S. Pat. Nos. 7,365,085 and 7,560,586 incorporated herein by reference.

The compound of formula II may be in any suitable form. For instance, it can be crystalline, amorphous, or a combination of both crystalline and amorphous forms. Also, the compound of formula II may be in a free base form or in a derivative form, such as in a pharmaceutically acceptable salt form. A hydrate, solvate, and/or co-crystal forms, as well as other derivatives, are also encompassed in this disclosure by reference to the compound of formula II (or a pharmaceutically acceptable salt thereof), unless specified otherwise. More than one compound of formula II, or its pharmaceutically acceptable salt, may be present in a formulation.

The compound of formula II may be either a single enantiomer (i.e., the R enantiomer or the S enantiomer) or may be a mixture of enantiomers, e.g., a racemate. If multiple diastereomers are present, the compound of formula II may be either a single diastereomer or a mixture of diastereomers. Unless specified otherwise, a reference to the compound is intended to encompass any one of these forms.

For example, the compound of formula II may be 2-{3-[3-({[2-chloro-3-(trifluoromethyl)phenyl]methyl}(2,2-diphenylethyl)amino)butoxy]phenyl}acetic acid (Compound (I)) (CAS No. 610318-54-2), the structure of which is:

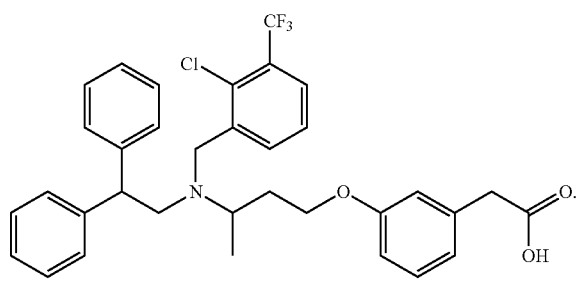 [SMILES: CC(CCOc1cccc(CC(=O)O)c1)N(Cc1cccc(C(F)(F)F)c1Cl)CC(c1ccccc1)c1ccccc1]

Compound (I) may be either a single enantiomer (i.e., the R enantiomer or the S enantiomer) or may be a mixture of enantiomers, e.g., a racemate. For example, the R enantiomer of compound (I) is 2-{3-[(3R)-3-({[2-chloro-3-(trifluoromethyl)phenyl]methyl}(2,2-diphenylethyl)amino)butoxy]phenyl}acetic acid (Compound (II)) (CAS No. 610318-03-1), the structure of which is:

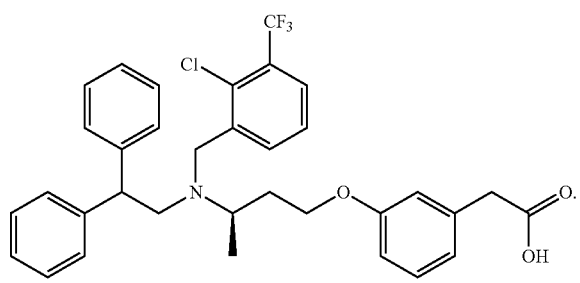

Compound (II), for instance, may be in a form of a free base and/or in a salt form; such as a hydrochloride (HCl) salt form or a fatty acid carboxylate salt form. By "fatty acid carboxylate" is meant the deprotonated form of a fatty acid, i.e., a carboxylic acid with a long aliphatic chain either saturated or unsaturated. Non-limiting examples of fatty acids include myristoleic acid, palmitoleic acid, sapienic acid, oleic acid, elaidic acid, vaccenic acid, linoleic acid, linoelaidic acid, arachidonic acid, eicosapentaenoic acid, erucic acid, docsahexaenoic acid, caprylic acid, capric acid, lauric acid, myristic acid, palmitic acid, stearic acid, arachidic acid, behenic acid, lignoceric acid, and cerotic acid.

Other LXR modulators that can be used with the compositions, formulations and methods described herein are disclosed, for example, in U.S. Pat. Nos. 7,247,748, 7,323,494, 7,365,085, and 7,560,586, the disclosure of each of which is incorporated herein by reference.

The formulation may be suitable for administration via at least one of the routes known in the art, for example, parenterally, topically, sublingually, or orally. Preferably, the formulation is suitable at least for oral administration.

The term "pharmaceutically acceptable salt" as used herein refers to any adduct between two or more chemical species that are capable of undergoing proton transfer. As such, the term "pharmaceutically acceptable salt" encompasses adducts in which complete proton transfer has occurred, adducts in which partial proton transfer has occurred (e.g., in which an equilibrium mixture of charged and uncharged species is formed), and/or adducts in which proton transfer has not occurred but the chemical species are associated e.g., by hydrogen bonding. It is understood that the term "pharmaceutically acceptable salt" also encompasses adducts in which close ion pairs are present. It will also be understood that the term "pharmaceutically acceptable salt" encompasses a continuum of adducts between those adducts in which complete proton transfer has occurred to form discrete ions and/or adducts in which two species are associated but proton transfer has not occurred, or has only partially occurred. See, e.g., Aitipamula et al. *Mol. Pharmaceutics,* 2007, 4 (3), pp 323-338. A given pharmaceutically acceptable salt can contain one or multiple adducts on this continuum. For example, the representation of the pharmaceutically acceptable salt of formula I, the structure of which is:

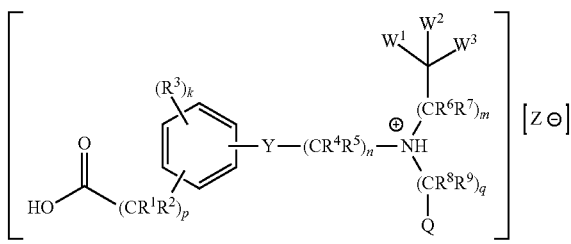

encompasses one or more species on the continuum between discrete ions and adducts in which proton transfer has not occurred from the Z group.

The formulation includes a vehicle that is capable of carrying the compound of formula II (or a pharmaceutically acceptable salt thereof).

The vehicle can be a lipophilic vehicle that includes at least one lipophilic excipient, and the compound of formula II, or its pharmaceutically acceptable salt, preferably is soluble therein. In particular, the lipophilic vehicle can include at least one lipid excipient in which the compound of formula II is soluble. In one aspect, the lipophilic vehicle comprises at least one lipid excipient and/or at least one surfactant.

The term "soluble", as used herein, refers to a solubility of at least about 25 mg/mL, e.g., 50 mg/mL, 72 mg/mL, 100 mg/mL, 150 mg/mL, 200 mg/mL in a given medium, either with or without the presence of other substances such as surfactants or solubilizing agents. Preferably, the compound of formula II (or a pharmaceutically acceptable salt thereof) has a solubility of at least 100 mg/mL in at least one lipophilic excipient.

The term "lipophilic" as used herein refers to substances having a tendency to dissolve in substances such as fats, oils, and lipids.

Preferably, to achieve better stability, the pH of the formulation is at least about 4. For instance, the pH can be about 4 to about 8, about 4 to about 7, about 4 to about 6, about 5 to about 8, about 5 to about 7, about 5 to about 6.

It has been found that achieving such pH values can lead to reduced degradation of the compound of formula II during storage of the formulation. Preferably, the pH of the formulation is about 5 to about 7. The term "pH" as used herein refers to the apparent pH that is the pH measured using pH paper (e.g. MColorpHast™ pH 0-6.0 or Universal Indicator 0-14) by the following procedure: the pH paper is wetted with water, a drop (approximately 20 µL) of the formulation is applied to pH paper, and the color change is compared to the pH color chart of the pH paper manufacturer.

Preferably, the formulation is such that the amount of the compound of formula II, or its pharmaceutically acceptable salt, decreases by less than about 2% (e.g., less than about 1.5%, less than about 1%, less than about 0.5%) after storage for at least 1 week (e.g., at least 2 weeks, at least 3 weeks, at least 6 weeks, at least 3 months, or at least 6 months) at a temperature of 40° C. (as used in this disclosure, the temperature variance can be +/−2° C.) and a relative humidity of 75% (as used in this disclosure, the relative humidity variance can be +/−5%). All storage conditions herein refer to storage at atmospheric pressure (at or about 1 atm).

In one aspect, the lipophilic excipient comprises a lipid excipient. In another aspect, the lipophilic excipient comprises a surfactant. The lipophilic vehicle can also comprise at least one lipid excipient and at least one surfactant. The lipophilic vehicle can be at least 50%, at least 60%, at least 70%, or at least 80% of the total weight of the formulation.

The lipid excipient can comprise a lipid or mixture of lipids. For example, the lipid excipient may comprise a monoglyceride, a diglyceride, and/or a triglyceride. Preferably, the lipids dissolve the compound of formula II, or its pharmaceutically acceptable salt, and may also facilitate its absorption into the lymphatic system. Non-limiting examples of suitable lipids that can be useful in the formulations of the invention include glycerol fatty acid esters such as glycerol linoleates, glycerol stearates, glycerol oleates, glycerol ethylhexanoates, glycerol caprylates, glycerol behenates, and glycerol laurates. Glycerol Esters of Fatty Acids, as known in the art, are esters of fatty acids and glycerol or polyglycerol and their derivatives. Glycerol Esters of Fatty Acids include glycerol fatty acid ester, glycerol acetic acid fatty acid ester, glycerol lactic acid fatty acid ester, glycerol citric acid fatty acid ester, glycerol succinic acid fatty acid ester, glycerol diacetyl tartaric acid fatty acid ester, glycerol acetic acid ester, polyglycerol fatty acid ester, and polyglycerol condensed ricinoleic acid ester. Commercial sources of glycerol linoleates-containing vehicles include, but are not limited to, Maisine 35-1 from Gattefosse and Cithrol GMO HP from Croda. Lipid chain length and/or degree of unsaturation may play a role in providing more favorable formulations from the standpoint of flavor or smell, or have toxicological effects. In one embodiment, the lipid excipient is about 40% by weight to about 80% by weight of the lipophilic vehicle, or about 50% by weight to about 80% by weight of the lipophilic vehicle, or about 60% by weight to about 80% by weight of the lipophilic vehicle, or about 60% by weight to about 70% by weight of the lipophilic vehicle, or about 50% by weight to about 70% by weight of the lipophilic vehicle. In one embodiment the formulation comprises about 20% by weight to about 32% by weight glyceryl monolinoleate, about 25% by weight to about 34% by weight glyceryl dilinoleate and about 3% by weight to about 12% by weight glyceryl trilinoleate.

Suitable surfactants include lipophilic and/or non-ionic surfactants and mixtures thereof. Such surfactants may have a hydrophilic-lipophilic balance (HLB) value of about 14 or less; or about 12 or less; or about 10 or less; or about 8 or less. In some embodiments the surfactant is a polyglycolized glyceride. By "polyglycolized glyceride" is meant a polyethylene glycol glyceride monoester, a polyethylene glycol glyceride diester, a polyethylene glycol glyceride triester, or a mixture thereof containing a variable amount of free polyethylene glycol, such as a polyethylene glycol-oil transesterification product. The polyglycolized glyceride can include either monodisperse (i.e., single molecular weight) or polydisperse polyethylene glycol moieties of a predetermined size or size range (e.g., PEG2 to PEG 40). Polyethylene glycol glycerides include, for example: PEG glyceryl caprate, PEG glyceryl caprylate, PEG-20 glyceryl laurate (Tagat® L, Goldschmidt), PEG-30 glyceryl laurate (Tagat® L2, Goldschmidt), PEG-15 glyceryl laurate (Glycerox L series, Croda), PEG-40 glyceryl laurate (Glycerox L series, Croda), PEG-20 glyceryl stearate (Capmul® EMG, ABITEC), and Aldo® MS-20 KFG, Lonza), PEG-20 glyceryl oleate (Tagat®, Goldschmidt), and PEG-30 glyceryl oleate (Tagat® O2, Goldschmidt). Caprylocapryl PEG glycerides include, for example, caprylic/capric PEG-8 glyceride (Labrasol®, Gattefosse), caprylic/capric PEG-4 glyceride (Labrafac® Hydro, Gattefosse), and caprylic/capric PEG-6 glyceride (SOFTIGEN®767, Huls). Oleoyl PEG glyceride include, for example oleoyl PEG-6 glyceride, (Labrafil M1944 CS, Gattefosee). Lauroyl PEG glycerides includes, for example, lauroyl PEG-32 glyceride (Gelucire® ELUCIRE 44/14, Gattefosse). Stearoyl PEG glycerides include, for example stearoyl PEG-32 glyceride (Gelucrire 50/13, Gelucire 53/10, Gattefosse). PEG castor oils include PEG-3 castor oil (Nikkol CO-3, Nikko), PEG-5, 9, and 16 castor oil (ACCONON CA series, ABITEC), PEG-20 castor oil, (Emalex C-20, Nihon Emulsion), PEG-23 castor oil (Emulgante EL23), PEG-30 castor oil (Incrocas 30, Croda), PEG-35 castor oil (Incrocas-35, Croda), PEG-38 castor oil (Emulgante EL 65, Condea), PEG-40 castor oil (Emalex C-40, Nihon Emulsion), PEG-50 castor oil (Emalex C-50, Nihon Emulsion), PEG-56 castor oil (Eumulgin® PRT 56, Pulcra SA), PEG-60 castor oil (Nikkol CO-60TX, Nikko), PEG-100 castor oil, PEG-200 castor oil (Eumulgin® PRT 200, Pulcra SA), PEG-5 hydrogenated castor oil (Nikkol HCO-5, Nikko), PEG-7 hydrogenated castor oil (Cremophor WO7, BASF), PEG-10 hydrogenated castor oil (Nikkol HCO-10, Nikko), PEG-20 hydrogenated castor oil (Nikkol HCO-20, Nikko), PEG-25 hydrogenated castor oil (Simulsol® 1292, Seppic), PEG-30 hydrogenated castor oil (Nikkol HCO-30, Nikko), PEG-40 hydrogenated castor oil (Cremophor RH 40, BASF), PEG-45 hydrogenated castor oil (Cerex ELS 450, Auschem Spa), PEG-50 hydrogenated castor oil (Emalex HC-50, Nihon Emulsion), PEG-60 hydrogenated castor oil (Nikkol HCO-60, Nikko), PEG-80 hydrogenated castor oil (Nikkol HCO-80, Nikko), and PEG-100 hydrogenated castor oil (Nikkol HCO-100, Nikko). Additional polyethylene glycol-oil transesterification products include, for example, stearoyl PEG glyceride (Gelucire® 50/13, Gattefosse). The polyglycolized glycerides useful in the formulations of the invention can include polyethylene glycol glyceride monoesters, diesters, and/or triesters of acetic, propionic, butyric, valeric, hexanoic, heptanoic, caprylic, nonanoic, capric, lauric, myristic, palmitic, heptadecanoic, stearic, arachidic, behenic, lignoceric, α-linolenic, stearidonic, eicosapentaenoic, docosahexaenoic, linoleic, γ-linolenic, dihomo-γ-linolenic, arachidonic, oleic, elaidic, eicosenoic, erucic, or nervonic acid, or mixtures thereof. The polyglycol moiety in a polyglycolized glyceride can be polydisperse; that is, they can have a variety of molecular weights. Examples of suitable surfactants include fatty acid macrogol-32 glycerides, such as lauroyl macrogol-32 glycerides (lauroyl polyoxylglycerides). Commercial sources of lauroyl macrogol-32 glycerides include Gelucire 44/14 from Gattefosse. Suitable surfactants include fatty acid macrogol-6 glycerides and fatty acid esters of propylene glycol. The surfactant (or mixture of surfactants) may be capable of promoting formation of an emulsion upon contact of the formulation with gastrointestinal fluids. In one embodiment, the surfactant is about 20% by weight to about 60% by weight of the lipophilic vehicle, or other aqueous systems. In other embodiments, the surfactant may be about 80% by weight to about 100% by weight of the lipophilic vehicle. In some embodiments, a surfactant can serve a dual role by both dissolving the compound of formula II, or its pharmaceutically acceptable salt, and acting as a surfactant.

The formulations may also comprise an agent that is capable of raising the pH of the formulation. This agent may be a weak base and/or a buffering agent. A weak base is a base that does not fully ionize in aqueous solution. In some embodiments the weak base may act as a buffering agent and form a buffer system in the formulation. It will be understood that when the weak base acts as a buffer in the formulation it is present in the formulation as an equilibrium mixture of its protonated and unprotonated forms i.e., as a mixture of the weak acid and its conjugate base. The protonated and unprotonated forms of the compound of formula II may also participate in the buffer system. Suitable weak bases include lipid-soluble carboxylic acid salts with a suitable counter-ion such as sodium, potassium, magnesium, and/or calcium. Soluble salts of short carboxylic acids are suitable. A short carboxylic acid may have between 2 and 7 carbons. For example, salts of acetic acid, propionic acid, butyric acid, isobutyric acid, valeric acid, pivalic acid, benzoic acid, and/or substituted benzoic acids. Salts of short chain fatty acids, medium chain fatty acids, long chain fatty acids, or very long chain fatty acids are also suitable. In some embodiments, the weak base is the salt of a long chain fatty acid. As is known in the art, a long chain fatty acid is a fatty acid that has between 13 carbon atoms and 21 carbon atoms. For example, salts of saturated fatty acids such as caprylic acid, capric acid, palmitic acid, lauric acid, and/or stearic acid are suitable. Salts of unsaturated fatty acids such as myristoleic acid, linoleic acid, linolenic acid, arachidonic acid, eicosenoic acid, palmitoleic acid, sapienic acid, oleic acid, elaidic acid, and/or vaccenic acid are also suitable. Very long chain fatty acids having 22 carbon atoms or more may also be suitable. Preferably, the weak base comprises sodium oleate.

Without wishing to be bound by a particular theory, it is believed that if the pH of the formulation is too low (e.g., due to an acidic compound of formula II), reactions of the compound of formula II with alcoholic groups in the excipients, such as esterification of a carboxylic acid group with glycerol, can occur. By adding a weak base, the pH of the formulation can be raised, e.g., to about pH 5 to about pH 7, to minimize such degradation reactions.

A content of a weak base, such as a lipid-soluble carboxylic acid salt, may be about 2% by weight to about 10% by weight of the formulation, or about 2% by weight to about 5% by weight of the formulation, or about 5% by weight to about 10% by weight of the formulation, or about 0.2% by weight to about 5% by weight of the formulation, or about 0.2% by weight to about 10% by weight of the formulation. For example, about 5% by weight of the formulation to about 7% by weight of the formulation. Without wishing to be bound by a particular theory, it is believed that the salt of a weak base, such as the sodium salt of a fatty acid may react with a compound of formula II (or a pharmaceutically acceptable salt thereof) to form a fatty acid salt of the compound of formula II. It is believed that such fatty acid salts improve the systemic bioavailability and stability of compounds of formula II.

In some embodiments, for example, when the lipid-soluble carboxylic acid salt is the salt of a fatty acid (such as sodium oleate), the lipid-soluble carboxylic acid salt can act as a surfactant as well as a buffer. If the buffer is not the salt of a fatty acid, it may be beneficial to include additional surfactants in the formulation.

If the form of the compound of formula II used in the formulation is a salt (e.g., a protonated form such as the hydrochloride salt), at least 1.1 molar equivalents of lipid-soluble carboxylic acid salt with respect to the compound of formula II may be included in the formulation. For instance, about 1.1 molar equivalents to about 3 molar equivalents, about 1.1 molar equivalents to about 2 molar equivalents, about 1.1 molar equivalents to about 1.5 molar equivalents, about 1.5 molar equivalents to about 3 molar equivalents, or about 1.5 molar equivalents to about 2 molar equivalents. Without wishing to be bound by a particular theory, it is thought that the first equivalent of lipid-soluble carboxylic acid salt effects an ion exchange with the protonated compound of formula II (e.g., the chloride of the hydrochloride salt exchanges with the carboxylate of the lipid-soluble carboxylic acid salt such as the oleate ion in sodium oleate) and the other amount equilibrates with the carboxylic acid group of the compound of formula II to form a buffer system. For instance, this results in the formation of a pharmaceutically acceptable salt of formula I:

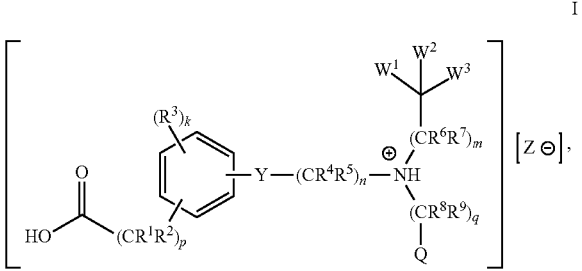

I wherein:
$Z^\ominus$ is a fatty acid carboxylate;
Y is selected from —O—, —S—, —N($R^{12}$)—, and —C($R^4$)($R^5$)—;
$W^1$ is selected from $C_1$-$C_6$ alkyl, $C_0$-$C_6$ alkyl, $C_3$-$C_6$ cycloalkyl, aryl and Het, wherein said $C_1$-$C_8$ alkyl, $C_3$-$C_8$ cycloalkyl, Ar and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl-$CO_2R^{12}$, —$C_0$-$C_6$ alkyl-C(O)$SR^{12}$, —$C_0$-$C_6$ alkyl-CONR$^{13}R^{14}$, —$C_0$-$C_6$ alkyl-COR$^{15}$, —$C_0$-$C_6$ alkyl-NR$^{13}R^{14}$, —$C_0$-$C_6$ alkyl-SR$^{12}$, —$C_0$-$C_6$ alkyl-OR$^{12}$, —$C_0$-$C_6$ alkyl-SO$_3$H, —$C_0$-$C_6$ alkyl-SO$_2$NR$^{13}R^{14}$, —$C_0$-$C_6$ alkyl-SO$_2R^{12}$, —$C_0$-$C_6$ alkyl-SOR$^{15}$, —$C_0$-$C_6$ alkylOCOR$^{15}$, —$C_0$-$C_6$ alkyl-OC(O)NR$^{13}R^{14}$, —$C_0$-$C_6$ alkyl-OC(O)OR$^{15}$, —$C_0$-$C_6$ alkyl-NR$^{13}$C(O)OR$^{15}$, —$C_0$-$C_6$ alkyl-NR$^{13}$C(O)NR$^{13}R^{14}$, and —$C_0$-$C_6$ alkyl-NR$^{13}$COR$^{15}$, where said $C_1$-$C_6$ alkyl, is optionally unsubstituted or substituted by one or more halo substituents;
$W^2$ is selected from H, halo, $C_1$-$C_6$ alkyl, $C_2$-$C_6$ alkenyl, $C_2$-$C_6$ alkynyl, —$C_0$-$C_6$ alkyl-NR$^{13}R^{14}$, —$C_0$-$C_6$ alkyl-SR$^{15}$, —$C_0$-$C_6$ alkyl-OR$^{12}$, —$C_0$-$C_6$ alkylCO$_2R^{12}$, —$C_0$-$C_6$ alkyl-C(O)SR$^{12}$, —$C_0$-$C_6$ alkylCONR$^{13}R^{14}$, —$C_0$-$C_6$ alkyl-COR$^{15}$, —$C_0$-$C_6$ alkylOCOR$^{15}$, —$C_0$-$C_6$ alkyl-OCONR$^{13}R^{14}$, —$C_0$-$C_6$ alkyl-NR$^{13}$CONR$^{13}R^{14}$, —$C_0$-$C_6$ alkyl-NR$^{13}$COR$^{15}$, —$C_0$-$C_6$ alkyl-Het, —$C_0$-$C_6$ alkyl-Ar, and —$C_0$-$C_6$ alkyl-$C_3$-$C_7$ cycloalkyl, wherein said $C_1$-$C_6$ alkyl is optionally unsubstituted or substituted by one or more halo substituents, and wherein the $C_3$-$C_7$ cycloalkyl, Ar and Het moieties of said —$C_0$-$C_6$ alkyl-Het, —$C_0$-$C_6$ alkyl-Ar and —$C_0$-$C_6$ alkyl-$C_3$-$C_7$ cycloalkyl are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl-$CO_2R^{12}$, —$C_0$-$C_6$ alkyl-C(O)SR$^{12}$, —$C_0$-$C_6$ alkyl-CONR$^{13}R^{14}$, —$C_0$-$C_6$ alkyl-COR$^{15}$, —$C_0$-$C_6$ alkyl-NR$^{13}R^{14}$, —$C_0$-$C_6$ alkyl-SR$^{12}$, —$C_0$-$C_6$ alkyl-OR$^{12}$, —$C_0$-$C_6$ alkyl-SO$_3$H, —$C_0$-$C_6$ alkyl-SO$_2$NR$^{13}R^{14}$, —$C_0$-$C_6$ alkyl-SO$_2R^{12}$, —$C_0$-$C_6$ alkyl-SOR$^{15}$, —$C_0$-$C_6$ alkyl-OCOR$^{15}$, —$C_0$-$C_6$ alkyl-OC(O)NR$^{13}R^{14}$, —$C_0$-$C_6$ alkyl-OC(O)OR$^{15}$, —$C_0$-$C_6$ alkyl-NR$^{13}$C(O)OR$^{15}$, —$C_0$-$C_6$ alkyl-NR$^{13}$C(O)NR$^{13}R^{14}$, and —$C_0$-$C_6$ alkyl-NR$^{13}$COR$^{15}$, where said $C_1$-$C_6$ alkyl, is optionally unsubstituted or substituted by one or more halo substituents;
$W^3$ is selected from the group consisting of: H, halo, $C_1$-$C_6$ alkyl, —$C_0$-$C_6$ alkyl-NR$^{13}R^{14}$, —$C_0$-$C_6$ alkylSR$^{12}$, —$C_0$-$C_6$ alkyl-OR$^{12}$, —$C_0$-$C_6$ alkyl-$CO_2R^{12}$, —$C_0$-$C_6$ alkyl-C(O)SR$^{12}$, —$C_0$-$C_6$ alkyl-CONR$^{13}R^{14}$, —$C_0$-$C_6$ alkyl-COR$^{15}$, —$C_0$-$C_6$ alkyl-OCOR$^{15}$, —$C_0$-$C_6$ alkyl-OCONR$^{13}R^{14}$, —$C_0$-$C_6$ alkylNR$^{13}$CONR$^{13}R^{14}$, —$C_0$-$C_6$ alkyl-NR$^{13}$COR$^{15}$, —$C_0$-$C_6$ alkyl-Het, —$C_1$-$C_6$ alkyl-Ar and —$C_1$-$C_6$ alkyl-$C_3$-$C_7$ cycloalkyl, wherein said $C_1$-$C_6$ alkyl is optionally unsubstituted or substituted by one or more halo substituents;
Q is selected from $C_3$-$C_8$ cycloalkyl, Ar, and Het; wherein said $C_3$-$C_8$ cycloalkyl, Ar, and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkylCO$_2R^{12}$, —$C_0$-$C_6$ alkyl-C(O)SR$^{12}$, —$C_0$-$C_6$ alkylCONR$^{13}R^{14}$, —$C_0$-$C_6$ alkyl-COR$^{15}$, —$C_0$-$C_6$ alkylNR$^{13}R^{14}$, —$C_0$-$C_6$ alkyl-SR$^{12}$, —$C_0$-$C_6$ alkyl-OR$^{12}$, —$C_0$-$C_6$ alkyl-SO$_3$H, —$C_0$-$C_6$ alkyl-SO$_2$NR$^{13}R^{14}$, —$C_0$-$C_6$ alkyl-SO$_2R^{12}$, —$C_0$-$C_6$ alkyl-SOR$^{15}$, —$C_0$-$C_6$ alkyl-OCOR$^{15}$, —$C_0$-$C_6$ alkyl-OC(O)NR$^{13}R^{14}$, —$C_0$-$C_6$ alkyl-OC(O)OR$^{15}$, —$C_0$-$C_6$ alkylNR$^{13}$C(O)OR$^{15}$, —$C_0$-$C_6$ alkyl-NR$^{13}$C(O)NR$^{13}R^{14}$, and —$C_0$-$C_6$ alkyl-NR$^{13}$COR$^{15}$, where said $C_1$-$C_6$ alkyl is optionally unsubstituted or substituted by one or more halo substituents;
p is 0-8;
n is 2-8;
m is 0 or 1;
q is 0 or 1;
each $R^1$ and $R^2$ are independently selected from H, halo, $C_1$-$C_6$ alkyl, $C_3$-$C_6$ alkenyl, $C_3$-$C_6$ alkynyl, —$C_0$-$C_6$ alkyl-NR$^{13}R^{14}$, —$C_0$-$C_6$ alkyl-OR$^{12}$, —$C_0$-$C_6$ alkyl-SR$^{12}$, —$C_1$-$C_6$ alkyl-Het, —$C_1$-$C_6$ alkyl-Ar, and —$C_1$-$C_6$ alkyl-$C_3$-$C_7$ cycloalkyl, or $R^1$ and $R^2$ together with the carbon to which they are attached form a 3-5 membered carbocyclic or heterocyclic ring, wherein said heterocyclic ring contains one, or more heteroatoms selected from N, O, and S, where any of said $C_1$-$C_6$ alkyl is optionally unsubstituted or substituted by one or more halo substituents;
each $R^3$ is the same or different and is independently selected from halo, cyano, nitro, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het, —$C_0$-$C_6$ alkyl-$C_3$-$C_7$ cycloalkyl, —$C_0$-$C_6$ alkyl-$CO_2R^{12}$, —$C_0$-$C_6$ alkyl-C(O)SR$^{12}$, —$C_0$-$C_6$ alkyl-CONR$^{13}R^{14}$, —$C_0$-$C_6$ alkyl-COR$^{15}$, —$C_0$-$C_6$ alkyl-NR$^{13}R^{14}$, —$C_0$-$C_6$ alkyl-SR$^{12}$, —$C_0$-$C_6$ alkyl-OR$^{12}$, —$C_0$-$C_6$ alkyl-SO$_3$H, —$C_0$-$C_6$ alkylSO$_2$NR$^{13}$R$^{14}$, —C$_0$-C$_6$ alkyl-SO$_2$R$^{12}$, —C$_0$-C$_6$ alkyl-SOR$^{15}$, —C$_0$-C$_6$ alkyl-OCOR$^{15}$, —C$_0$-C$_6$ alkyl-OC(O)NR$^{13}$R$^{14}$, —C$_0$-C$_6$ alkyl-OC(O)OR$^{15}$, —C$_0$-C$_6$ alkyl-NR$^{13}$C(O)OR$^{15}$, —C$_0$-C$_6$ alkyl-NR$^{13}$C(O)NR$^{13}$R$^{14}$, and —C$_0$-C$_6$ alkyl-NR$^{13}$COR$^{15}$, wherein said C$_1$-C$_6$ alkyl is optionally unsubstituted or substituted by one or more halo substituents;

each R$^4$ and R$^5$ is independently selected from H, halo, C$_1$-C$_6$ alkyl, —C$_0$-C$_6$ alkyl-Het, —C$_0$-C$_6$ alkyl-Ar, and —C$_0$-C$_6$ alkyl-C$_3$-C$_7$ cycloalkyl; R$^6$ and R$^7$ are each independently selected from H, halo, C$_1$-C$_6$ alkyl, —C$_0$-C$_6$ alkyl-Het, —C$_0$-C$_6$ alkyl-Ar and —C$_0$-C$_6$ alkyl-C$_3$-C$_7$ cycloalkyl;

R$^8$ and R$^9$ are each independently selected from H, halo, C$_1$-C$_6$ alkyl, —C$_0$-C$_6$ alkyl-Het, —C$_0$-C$_6$ alkyl-Ar and —C$_0$-C$_6$ alkyl-C$_3$-C$_7$ cycloalkyl;

R$^{10}$ and R$^{11}$ are each independently selected from H, C$_1$-C$_{12}$ alkyl, C$_3$-C$_{12}$ alkenyl, C$_3$-C$_{12}$ alkynyl, —C$_0$-C$_8$ alkyl-Ar, —C$_0$-C$_8$ alkyl-Het, —C$_0$-C$_8$ alkyl-C$_3$-C$_7$ cycloalkyl, —C$_0$-C$_8$ alkyl-O—Ar, —C$_0$-C$_8$ alkyl-O-Het, —C$_0$-C$_8$ alkyl-O—C$_3$-C$_7$ cycloalkyl, —C$_0$-C$_8$ alkyl-S(O)$_x$—C$_0$-C$_8$ alkyl, —C$_0$-C$_8$ alkyl-S(O)$_x$—Ar, —C$_0$-C$_8$ alkyl-S(O)$_x$—Het, —C$_0$-C$_8$ alkyl-S(O)$_x$—C$_3$-C$_7$ cycloalkyl, —C$_0$-C$_8$ alkyl-NH—Ar, —C$_0$-C$_8$ alkyl-NH-Het, —C$_0$-C$_8$ alkyl-NH—C$_3$-C$_7$ cycloalkyl, —C$_0$-C$_8$ alkyl-N(C$_1$-C$_4$ alkyl)-Ar, —C$_0$-C$_8$ alkyl-N(C$_1$-C$_4$ alkyl)-Het, —C$_0$-C$_8$ alkyl-N(C$_1$-C$_4$ alkyl)-C$_3$-C$_7$ cycloalkyl, —C$_0$-C$_8$ alkyl-Ar, —C$_0$-C$_8$ alkyl-Het, and —C$_0$-C$_8$ alkyl-C$_3$-C$_7$ cycloalkyl, where x is 0, 1, or 2, or R$^{10}$ and R$^{11}$, together with the nitrogen to which they are attached, form a 4-7 membered heterocyclic ring which optionally contains one or more additional heteroatoms selected from N, O, and S, wherein said C$_1$-C$_{12}$ alkyl, C$_3$-C$_{12}$ alkenyl, or C$_3$-C$_{12}$ alkynyl is optionally substituted by one or more of the substituents independently selected from the group halo, —OH, —SH, —NH$_2$, —NH(unsubstituted C$_1$-C$_6$ alkyl), —N(unsubstituted C$_1$-C$_6$ alkyl)(unsubstituted C$_1$-C$_6$ alkyl), unsubstituted —OC$_1$-C$_6$ alkyl, —CO$_2$H, —CO$_2$(unsubstituted C$_1$-C$_6$ alkyl), —CONH$_2$, —CONH(unsubstituted C$_1$-C$_6$ alkyl), —CON(unsubstituted C$_1$-C$_6$ alkyl)(unsubstituted C$_1$-C$_6$ alkyl), —SO$_3$H, —SO$_2$NH$_2$, —SO$_2$NH(unsubstituted C$_1$-C$_6$ alkyl) and —SO$_2$N(unsubstituted C$_1$-C$_6$ alkyl)(unsubstituted C$_1$-C$_6$ alkyl);

R$^{12}$ is selected from H, C$_1$-C$_6$ alkyl, C$_3$-C$_6$ alkenyl, C$_3$-C$_6$ alkynyl, —C$_0$-C$_6$ alkyl-Ar, —C$_0$-C$_6$ alkyl-Het and —C$_0$-C$_6$ alkyl-C$_3$-C$_7$ cycloalkyl;

each R$^{13}$ and each R$^{14}$ are independently selected from H, C$_1$-C$_6$ alkyl, C$_3$-C$_6$ alkenyl, C$_3$-C$_6$ alkynyl, —C$_0$-C$_6$ alkyl-Ar, —C$_0$-C$_6$ alkyl-Het, and —C$_0$-C$_6$ alkyl-C$_3$-C$_7$ cycloalkyl, or R$^{13}$ and R$^{14}$ together with the nitrogen to which they are attached form a 4-7 membered heterocyclic ring which optionally contains one or more additional heteroatoms selected from N, O, and S; and R$^{15}$ is selected from C$_1$-C$_6$ alkyl, C$_3$-C$_6$ alkenyl, C$_3$-C$_6$ alkynyl, —C$_0$-C$_6$ alkyl-Ar, —C$_0$-C$_6$ alkyl-Het, and —C$_0$-C$_6$ alkyl-C$_3$-C$_7$ cycloalkyl.

In other embodiments, where greater than 1.1 molar equivalents of lipid-soluble carboxylic acid salt with respect to the compound of formula II are included in the formulation, it may beneficially further raise the pH of the formulation. During manufacturing, the lipid-soluble carboxylic acid salt is preferably added to the formulation before the compound of formula II in order to minimize formation of glycerol esters of the compound of formula II that can take place at low pH. The formation of glycerol esters can also be minimized by reducing the temperature of the mixture e.g., to 40-45° C.

One or more stabilizing agents may also be present in the formulation, such as antioxidants and metal chelating agents. Suitable antioxidants include sodium citrate, BHT and BHA. An antioxidant may be included in the formulation at a content of at least about 50 ppm by weight of the formulation to about 2% by weight of the formulation, or about 50 ppm by weight of the formulation to about 1% by weight of the formulation, or about 100 ppm by weight of the formulation to about 2% by weight of the formulation, or about 200 ppm by weight of the formulation to about 2% by weight of the formulation, or about 0.1% by weight of the formulation to about 2% by weight of the formulation, or about 0.1% by weight of the formulation to about 1% by weight of the formulation, or about 200 ppm by weight of the formulation to about 1% by weight of the formulation. Other stabilizing agents include, for example, sodium citrate, TPGS compounds and EDTA. EDTA may be used as its sodium salt, disodium-EDTA. These stabilizing agents can help to reduce degradation of the compound of formula II during storage due to processes such as oxidation. Chelating agents such as EDTA are also thought to slow degradation by chelating metal ions that can catalyze the oxidation of the compound of formula II. A TPGS compound may be included at about 5% by weight to about 25% by weight of the formulation. EDTA may be included at about 0.1% by weight to about 2% by weight of the formulation, or about 0.1% by weight of the formulation to about 1% by weight of the formulation. By "TPGS compound" is meant a compound or mixture of compounds containing one or more vitamin E moieties (e.g., a tocopherol, tocomonoenol, tocodienol, or tocotrienol) bonded to (e.g., by an ester, amide, or thioester bond) to one or more polyethylene glycol (PEG) moieties via a linker (e.g., a dicarboxylic or tricarboxylic acid). The vitamin E moiety can be any naturally occurring or synthetic form of vitamin E, including α-, β-, γ-, and δ-isoforms and all stereoisomers of tocopherol, tocomonoenol, tocodienol, and tocotrienol. Linkers include, for example, dicarboxylic acids (e.g., succinic acid, sebacic acid, dodecanedioic acid, suberic acid, or azelaic acid, citraconic acid, methylcitraconic acid, itaconic acid, maleic acid, glutaric acid, glutaconic acid, fumaric acids and phthalic acids). Exemplary tocopherol polyethylene glycol diesters are TPGS, tocopherol sebacate polyethylene glycol, tocopherol dodecanodioate polyethylene glycol, tocopherol suberate polyethylene glycol, tocopherol azelaate polyethylene glycol, tocopherol citraconate polyethylene glycol, tocopherol methylcitraconate polyethylene glycol, tocopherol itaconate polyethylene glycol, tocopherol maleate polyethylene glycol, tocopherol glutarate polyethylene glycol, tocopherol glutaconate polyethylene glycol, and tocopherol phthalate polyethylene glycol. Each of the PEG moieties of the TPGS compound can be any polyethylene glycol or any PEG derivative, and can have a molecular weight of 200-6000 kDa (e.g., 400-4000 kDa, 500-2000 kDa, 750-1500 kDa, 800-1200 kDa, 900-1100 kDa, or about 1000 kDa). The PEG moieties can be polydisperse; that is, they can have a variety of molecular weights. PEG derivatives include, for example, methylated PEG, propylene glycol, PEG-NHS, PEG-aldehyde, PEG-SH, PEG-NH$_2$, PEG-CO$_2$H, PEG-OMe and other ethers, branched PEGs, and PEG copolymers (e.g., PEG-b-PPG-b-PEG-1100, PEG-PPG-PEG-1900, PPG-PEG-MBE-1700, and PPG-PEG-PPG-2000). Any known source of TPGS compound can be used in the present invention. An exemplary TPGS compound is tocopheryl PEG-1000 succinate (TPGS-1000), which has a PEG moiety having a molecular weight of 1000 kDa. A food grade TPGS-1000 is available, for example, under the trade name Eastman Vitamin E TPGS® (Eastman Chemical Company, Kingsport, Tenn.). This TPGS is water-soluble form of natural-source vitamin E, which is prepared by esterification of crystalline D-α-tocopheryl acid succinate with polyethylene glycol 1000 (PEG 1000), and contains between 260 and 300 mg/g total tocopherol. Another exemplary TPGS compound is Water Soluble Natural Vitamin E (ZMC-USA, The Woodlands, Tex.). Methods of preparing TPGS are described in U.S. Pat. Nos. 2,680,749 and 3,102,078 and in U.S. Publication Nos. 2007/0184117 and 2007/0141203, which are herein incorporated by reference. TPGS compounds also include TPGS analogs that differ in chemical composition from TPGS by the substitution, addition, or removal of one or more atoms, methylene $(CH_2)_n$ units, or functional groups. TPGS analogs also include chromanol derivatives (e.g., 6-chromanol PEG-1000 succinate and 6-chromanol PEG-400 succinate), steroid derivatives (e.g., cholesteryl PEG-1000 succinate, cholic acid PEG-1000, dihydrocholic acid PEG-1000, lithocholic acid PEG-1000, ursodeoxycholic acid PEG-1000, chenodeoxycholic acid PEG-1000), and others (e.g., indomethacin PEG-1000, chromone-2-carboxylic acid PEG-1000, chromone-2-carboxylic acid PEG-1100-OMe, chromone-2-carboxylic acid PEG-1500, chromone-2-carboxylic acid PEG-2000, naproxen PEG-1000, probenecid PEG-1000, 7-carboxymethoxy-4-methyl-coumarin PEG-1000, 5-(4-chlorophenyl)-2-furoic acid PEG-1000, probenecid tocopheryl PEG-1000 succinate, lithocholic acid PEG-1000, and chromone-3-carboxylic acid PEG-1000, 7-hydroxy-coumarinyl-4-acetic acid PEG-1000).

In one embodiment, the compound of formula II is present at 10-200 mg per unit dose, or 10-100 mg per unit dose, or 10-40 mg per unit dose.

In one embodiment of the formulation:
(1) the lipid excipient content of the lipophilic vehicle is about 40% by weight to about 80% (e.g., about 40% to about 60%, about 50% to 70%, about 60% to about 80%) by weight;
(2) the surfactant content of the lipophilic vehicle is about 20% by weight to about 60% (e.g., about 20% to about 40%, about 30% to 50%, about 40% to about 60%) by weight; and the formulation comprises:
(3) about 2% by weight to about 10% (e.g., about 2% to 5%, about 3% to 7%, about 5% to about 10%) by weight of lipid-soluble carboxylic acid salt;
(4) 10-200 mg (e.g., about 10-50 mg, about 30-70 mg, about 50-100 mg, about 70-125 mg, about 100-150 mg, about 100-200 mg) of Compound (II) (or equivalent effective amount if a salt of Compound (II) is used).

In another embodiment of the formulation:
(1) the glyceryl linoleates content of the lipophilic vehicle is about 40% by weight to about 80% (e.g., about 40% to about 60%, about 50% to 70%, about 60% to 80%) by weight;
(2) the lauroyl macrogol-32 glycerides content of the lipophilic vehicle is about 20% by weight to about 60% (e.g., about 20% to about 40%, about 30% to about 50%, about 40% to about 60%) by weight; and the formulation comprises:
(3) about 2% by weight to about 10% (e.g., about 2% to 5%, about 3% to 7%, about 5% to about 10%) by weight of sodium oleate;
(4) 10-100 mg (e.g., about 10-50 mg, about 30-70 mg, about 50-100 mg, about 70-125 mg, about 100-150 mg) of Compound (II) (or equivalent effective amount if a salt of Compound (II) is used). The salt may be an HCl salt.

In another embodiment of the formulation:
(1) the glyceryl linoleates content of the lipophilic vehicle is about 40% by weight to about 80% (e.g., about 40% to about 60%, about 50% to 70%, about 60% to 80%) by weight;
(2) the lauroyl macrogol-32 glycerides content of the lipophilic vehicle is about 20% by weight to about 60% (e.g., about 20% to about 40%, about 30% to about 50%, about 40% to about 60%) by weight; and the formulation comprises:
(3) about 2% by weight to about 10% (e.g., about 2% to 5%, about 3% to 7%, about 5% to about 10%) by weight of sodium oleate;
(4) 10-40 mg (e.g., about 10-20 mg, about 15-25 mg, about 20-30 mg, about 25-35 mg, about 30-40 mg) of Compound (II) (or equivalent effective amount if a salt of Compound (II) is used). The salt may be an HCl salt.

In another embodiment the of formulation:
(1) the glyceryl linoleates content of the lipophilic vehicle is about 40% by weight to about 80% (e.g., about 40% to about 60%, about 50% to about 70%, about 60% to about 80%) by weight;
(2) the lauroyl macrogol-32 glycerides content of the lipophilic vehicle is about 20% by weight to about 60% (e.g., about 20% to about 40%, about 30% to about 50%, about 40% to about 60%) by weight; and the formulation comprises:
(3) about 2% by weight to about 10% (e.g., about 2% to 5%, about 3% to 7%, about 5% to about 10%) by weight of sodium oleate;
(4) 10-40 mg (e.g., about 10-20 mg, about 15-25 mg, about 20-30 mg, about 25-35 mg, about 30-40 mg) of Compound (II) (or equivalent effective amount if a salt of Compound (II) is used). The salt may be an HCl salt; and the formulation optionally comprises,
(5) about 0.1% by weight to about 1% (e.g., about 0.1% to about 0.5%, about 0.3 to about 0.7%, about 0.5% to about 1%) by weight EDTA; and/or
(6) about 0.1% by weight to about 1% (e.g., about 0.1% to about 0.5%, about 0.3 to about 0.7%, about 0.5% to about 1%) by weight sodium citrate.

The formulation can be a semi-solid suspension in which the compound of formula II, or its pharmaceutically acceptable salt, is dissolved. The term "semi-solid" as used herein refers to a material having a viscosity and a rigidity intermediate between that of a solid and a liquid (e.g., such as ointments, creams, gels, jellies, or pastes). It is thought that in some embodiments, the formulation can act as a Self-Emulsifying Drug Delivery system (SEDDS), Self-Microemulsifying Drug Delivery system (SMEDDS) and/or a Self-Nanoemulsying Drug Delivery system (SNEDDS). The term "self-emulsifying" refers to a formulation which, when diluted by water or other aqueous medium and gently mixed, yields a stable oil/water emulsion. When such an emulsion is formed in the gastrointestinal tract after oral administration of a formulation, it may enhance absorption of the compound of formula II into the lymphatic system and thus improve its systemic bioavailability.

The formulation can be loaded into a capsule for oral administration. By "capsule" is meant a capsule that includes a membrane that forms a two-part, capsule-shaped, container capable of carrying a solid, semi-solid, or liquid payload of drug, additive(s), and, optionally, excipients. Suitable capsules include hard and soft shell gelatin capsules; HPMC (hydroxypropyl methylcellulose) capsules; and other non-gelatin soft gel capsules. An example of a suitable non-gelatin soft gel capsule is Optishell™ that is available from Catalent. Further suitable examples are described in U.S. Pat. Nos. 6,582,727, 6,340,473, 6,884,060, 8,231,896, and 8,377,470, the disclosures of which are incorporated by reference herein.

The capsule can comprise about 10 mg to about 200 mg, about 10 mg to about 150 mg, about 10 mg to about 100 mg, or about 10 mg to about 40 mg of Compound (II) (or equivalent effective amount if a salt of Compound (II) is used).

The formulations of Compound (II) (and capsules comprising such formulations) described herein may be used in the treatment of a disease by administration to a patient suffering from such a disease. These diseases include cancers such as ovarian cancer, breast cancer, lung cancer, glioblastoma, melanoma, bladder cancer, head and neck cancer, renal cell cancer, colorectal cancer, lymphoma, leukemia, multiple myeloma hepatocellular carcinoma, a high grade neuroendocrine tumor and/or a small cell carcinoma such as a lung cancer. The formulations of (and capsules comprising such formulations) may also be used in the preparation of a dosage form for the treatment of diseases including cancers such as ovarian cancer, breast cancer, lung cancer, glioblastoma, melanoma, bladder cancer, head and neck cancer, renal cell cancer, colorectal cancer, lymphoma, leukemia, multiple myeloma, hepatocellular carcinoma, a high grade neuroendocrine tumor and/or a small cell carcinoma such as a lung cancer.

EXAMPLES

Example 1—Solubility Study of Compound (II)

A solubility study of Compound (II) was conducted using lipid excipients and surfactants. Compound (II) HCl and Compound (II) free base was weighed into vials and the appropriate amount of excipient was added to achieve the desired concentration. Heating and sonication was used, if necessary, to achieve clear solutions. Limits of solubility of Compound (II) free base and Compound (II) HCl (amorphous form) are noted in Table 1.

TABLE 1

| Excipient | Compound (II) (mg/mL) | Comment | Compound (II) HCl salt (mg/mL) | Comment |
| --- | --- | --- | --- | --- |
| Labrafac Lipo WL 1349 | >200 | RT | Insoluble | <25 mg/mL |
| Labrafac PG | >200 | RT | Insoluble | <25 mg/mL |
| Peceol | >200 | 20 min H&S | 150 | 5 min H&S |
| Maisine 35-1 | >200 | 10 min H&S | 150 | 5 min H&S |
| Labrasol | >200 | clear | 150 | 5 min H&S |
| Capmul MCM | | | 50 | 10 min H&S |
| Gelucire 44/14 | >200 | 5 min H&S | 100 | 10 min H&S |
| Labrafil M 2130 CS | >200 | 5 min H&S | 25 | 10 min H&S |
| Labrafil M 1944 CS | >200 | RT | 25 | 10 min H&S |
| Labrafil M 2125 CS | >200 | RT | 25 | 10 min H&S |
| Gelucire 50/13 | 150 | 10 min H&S | 50 | 10 min H&S |
| Capryol 90 | >200 | RT | 150 | 5 min H&S |
| Capryol PGMC | >200 | RT | 150 | 5 min H&S |
| Lauroglycol 90 | >200 | RT | 150 | 10 min H&S |
| Lauroglycol FCC | >200 | RT | 100 | 5 min H&S |
| Plurol Oleique CC 497 | >200 | 20 min H&S | 50 | 30 min H&S |
| Ethanol | >200 | RT | 200 | RT |
| Propylene Glycol | >200 | 5 min H&S | 200 | 5 min H&S |
| PEG-200 | >200 | RT | 200 | 5 min H&S |
| Transcutol | >200 | RT | 150 | RT |
| PEG-300 | >200 | RT | 200 | 5 min H&S |
| PEG-400 | >200 | 5 min H&S | 200 | 5 min H&S |
| Tween-20 | >200 | 5 min H&S | 200 | 20 min H&S |
| Tween-80 | >200 | 5 min H&S | 200 | 20 min H&S |
| Phosal 50-PG | >200 | 5 min H&S | 200 | 20 min H&S |
| Phosal 53 MCT | >200 | 5 min H&S | 150 | 10 min H&S |
| VitE-TPGS | >200 | 20 min H&S | 150 | 10 min H&S |
| Cremophor EL | >200 | 20 min H&S | 150 | 10 min H&S |
| Cremophor RH-40 | >200 | 20 min H&S | 150 | 10 min H&S |

RT = Vortexing at room temperature;
H&S = Heat and sonication

A further solubility study of Compound (II) was conducted using lipid excipients and surfactants. Maisine 35-1 (glycerol linoleates):Gelucire 44/14 (lauroyl macrogol-32 glycerides):Lauroglycol 90 (propylene glycol monolaurate) mixtures were tested to explore the optimal combination. The following ranges of each substance were tested: (1) 40-80% (w/w) Maisine 35-1; (2) 20-40% (w/w) Gelucire 44/14; and (3) 0-20% (w/w) Lauroglycol 90. In summary: Compound (II) Free Base exhibited high solubility >250 mg/mL; Compound (II) HCl Salt exhibited good solubility 150-200 mg/mL; Gelucire 44/14 reduced the solubility of the HCl salt; and Lauroglycol 90 showed no clear effects on solubility.

Example 2—Emulsification Study of Compound (II)

The highest achievable concentration of Compound (II) in Maisine 35-1, Gelucire 44/14 and Lauroglycol 90 mixtures was tested in emulsification studies. The mixtures were diluted with 1 N HCl (as a surrogate for simulated gastric fluid) and the following dilutions were tested: 1/10, 1/30 & 1/100.

In summary, Gelucire 44/14 clearly created fine emulsions, which became finer as the concentration of this excipient was increased. Lauroglycol 90 showed no clear effects on emulsion formation. All dilution levels formed nice emulsions. However, the emulsions formed by 1/10 dilutions separated more quickly.

Based on the results of the solubility and emulsification studies, formulations of Compound (II) with Maisine 35-1 and Gelucire 44/14 were selected for examination as to their stability properties.

Example 3—Compatibility and Stability Studies of Compound (II) Formulations

The compatibility of Compound (II) with excipients used was established through a binary stressed-stability study (40° C./75% RH) with the following solubilizing/emulsifying excipients: Maisine 35-1; Gelucire 44/14; sodium oleate; sodium stearate; vitamin E TPGS; lysine; and sodium EDTA.

The results indicated that short-term stability of Compound (II) in contact with Maisine 35-1 and Gelucire 44/14 (70:30 w/w) was acceptable at room temperature (i.e., about 20° C.) for 8 days, and then approximately 9% degradation occurred by 15 days. No significant degradation was noted after 15 days of storage at −20° C.

Sodium oleate (5% w/w) was added to the Maisine/Gelucire formulation to improve the miscibility of the formulation components, and buffer the acidic nature of the solution, which was found to improve stability. The amount of sodium oleate used was 1.5 equivalents relative to Compound (II) HCl. This may demonstrate that 1.0 eq. of sodium oleate quenches the HCl, forming Compound (II), oleic acid and NaCl. The remaining 0.5 eq. equilibrates with the carboxylic acid of Compound (II) to form a buffer system that inhibits the formation of glyercol ester degradation products of Compound (II).

Example 4—Stability of Compound (II) Formulations Containing Either Sodium Citrate or EDTA (40° C./75% RH)

In order to further reduce the potential for oxidation of the formulation, butylated hydroxyanisole (BHA) and sodium citrate were evaluated for compatibility with Compound (II), and for their ability to reduce degradation in the formulation. Disodium EDTA was also evaluated as a stabilizing agent in the Maisine 35-1/Gelucire 44/14 formulation due to the possibility of trace metal ions catalyzing the oxidative degradation of Compound (II). A formulation containing Maisine 35-1/Gelucire (44/14)/Vitamin E TPGS/sodium oleate (75/10/10/5 w/w/w/w) was also tested.

The stability of Compound (II) formulations containing either BHA, sodium citrate or EDTA were compared to control formulations that did not contain these additives. The results, summarized in Table 2, indicate that both antioxidants and EDTA improve the stability of the Compound (II) formulations after four days storage at 40° C./75% RH, with sodium citrate (1 mg/g) proving superior to BHA (0.2 mg/g).

TABLE 2

| Formulation | Time (0) Assay (%) | Day 4 Assay (%) | Day 4 Impurity 1 (%) (RT 8.32) | Day 4 Impurity 2 (%) (RT 8.58) |
|---|---|---|---|---|
| Compound (II) (100 mg) + 1 g Maisine 35-1/Gelucire (44/14)/TPGS/sodium oleate (75/10/10/5) (A) | 95.33 | 91.01 | 0.10 | 1.23 |

TABLE 2-continued

| Formulation | Time (0) Assay (%) | Day 4 Assay (%) | Day 4 Impurity 1 (%) (RT 8.32) | Day 4 Impurity 2 (%) (RT 8.58) |
|---|---|---|---|---|
| Compound (II) (100 mg) + 1 g Maisine 35-1/Gelucire (44/14)/sodium oleate (75/20/5) (B) | 95.53 | 91.21 | 0.08 | 1.10 |
| A + 0.2 mg BHA | 95.33 | 92.45 | 0.06 | 0.78 |
| B + 0.2 mg BHA | 95.76 | 92.83 | 0.14 | 0.76 |
| A + 1 mg EDTA | 95.31 | 94.24 | 0.07 | 0.23 |
| B + 1 mg EDTA | 95.44 | 95.09 | 0.20 | 0.40 |
| A + 1 mg sodium citrate | 95.14 | 94.95 | 0.27 | 0.45 |
| B + 1 mg sodium citrate | 94.94 | 93.76 | 0.16 | 0.39 |

Example 5—Stability of Compound (II) Formulations Containing Both Sodium Citrate and EDTA (40° C./75% RH)

In this example, the stability of Compound (II) formulations containing both sodium citrate and EDTA were compared to control formulations that did not contain these additives. The results, summarized in Table 3, indicate that formulations containing the combination of sodium oleate, sodium citrate and EDTA are significantly more stable after three days storage at 40° C./75% RH than those without these excipients. The additional stability conferred by sodium oleate is likely due to the buffering capacity (the pH of the solution is increased from pH 1 to pH 5 by the addition of sodium oleate).

TABLE 3

| Formulation | Time (0) Assay (%) | Day 3 Assay (%) |
|---|---|---|
| Compound (II) (100 mg) + 1 g Maisine 35-1/Gelucire (44/14)/TPGS/sodium oleate (75/10/10/5) (A) | 97.73 | 85.73 |
| Compound (II) (100 mg) + 1 g Maisine 35-1/Gelucire(44/14)/sodium oleate (75/20/5) (B) | 97.70 | 95.20 |
| A + 1 mg EDTA + 1 mg sodium citrate | 98.23 | 90.88 |
| B + 1 mg EDTA + 1 mg sodium citrate | 98.08 | 97.79 |
| A + 1 mg EDTA + 2 mg sodium citrate | 98.18 | 92.82 |
| B + 1 mg EDTA + 2 mg sodium citrate | 97.91 | 97.59 |

Example 6—Stability of Encapsulated Compound (II) Formulations

In this example, a six-week stability study was conducted on formulations containing Compound (II), Maisine 35-1, sodium oleate, EDTA, sodium citrate, and Gelucire 44/14 and/or Vitamin E TPGS (see Tables 4 & 5). In addition to testing the blends (assay only), both gelatin and HPMC capsules were manually filled with each blend to evaluate compatibility and stability after 6 weeks of storage at 25° C./60% RH and 40° C./75% RH.

The results, summarized in the Tables 4 & 5, indicate that each blend remained essentially unchanged after 6 weeks at 25° C./60% RH and 40° C./75% RH. Samples stored at 40° C. in gelatin capsules did not show any significant trend in degradation after 6 weeks, but Formulations B and C stored in HPMC capsules exhibited a 1-2% decrease in assay value at the higher temperature storage conditions.

TABLE 4

Test formulations:

| Component | Vendor | Batch/Catalog | Formulation 1 (A) | | Formulation 2 (B) | | Formulation 3 (C) | |
|---|---|---|---|---|---|---|---|---|
| Compound (II) HCl | Sponsor | ELS-70-106-70 | 7.90% | 4.345 g | 7.90% | 4.345 g | 7.90% | 4.345 g |
| Maisine ™ 35-1 | Gattefossé | N/A | 62.20% | 34.21 g | 62.20% | 34.21 g | 62.20% | 34.21 g |
| Gelucire ® 44/14 | Gattefossé | N/A | 24.20% | 13.31 g | 12.10% | 6.655 g | 0% | 0 g |
| Vit-E-TPGS | Isochem | 318300 | 0% | 0 g | 12.10% | 6.655 g | 24.20% | 13.31 g |
| Sodium Oleate | Pfaltz & Bauer | S06450 | 5.50% | 3.025 g | 5.50% | 3.025 g | 5.50% | 3.025 g |
| Disodium EDTA | Fisher | S311-100 | 0.10% | 0.055 g | 0.10% | 0.055 g | 0.10% | 0.055 g |
| Sodium citrate | Fisher | S279-500 | 0.10% | 0.055 g | 0.10% | 0.055 g | 0.10% | 0.055 g |
| Total | | | 100% | 55 g | 100% | 55 g | 100% | 55 g |

TABLE 5

Stability Results:

| Formulation | Assay (%) Initial | Assay (%) 25° C./60% RH | | | Assay (%) 40° C./75% RH | | |
|---|---|---|---|---|---|---|---|
| | | Week 1 | Week 3 | Week 6 | Week 1 | Week 3 | Week 6 |
| A (blend only) | 97.4 | 97.0 | — | — | 98.0 | 97.7 | 97.5 |
| A (gelatin capsules) | 98.0 | 97.7 | 96.7 | 98.7 | 97.8 | 97.9 | 98.4 |
| A (HPMC capsules) | 97.0 | 97.2 | 97.8 | 98.1 | 97.6 | 97.4 | 97.1 |
| B (blend only) | 97.3 | 96.8 | — | — | 97.7 | 97.5 | 96.4 |
| B (gelatin capsules) | 97.5 | 97.1 | 97.7 | 98.6 | 97.8 | 97.8 | 98.0 |
| B (HPMC capsules) | 97.7 | 97.2 | 97.5 | 98.0 | 97.4 | 96.8 | 95.5 |
| C (blend only) | 97.5 | 97.7 | — | — | 97.2 | 97.4 | 96.6 |
| C (gelatin capsules) | 97.7 | 97.2 | 97.3 | 98.3 | 97.4 | 97.5 | 97.2 |
| C (HPMC capsules) | 97.4 | 97.3 | 97.2 | 97.3 | 96.7 | 96.4 | 95.6 |

Example 7—Exemplary Pharmaceutical Formulations of Compound (II)

TABLE 6

| Components | Amount per 10 mg Capsule (mg) | Weight (%) | Amount per 40 mg Capsule (mg) | Weight (%) | Amount per 80 mg Capsule (mg) | Weight (%) |
|---|---|---|---|---|---|---|
| Compound (II) HCl | 10.99 | 7.90[1] | 43.97 | 7.90[1] | 87.90 | 15.8 |
| Maisine ™ 35-1 (glyceryl linoleates) | 86.52 | 62.20 | 346.21 | 62.20 | 292.5 | 52.5 |
| Gelucire ® 44/14 (lauroyl macrogol-32 glycerides) | 33.66 | 24.20 | 134.70 | 24.20 | 113.8 | 20.4 |
| Sodium Oleate | 7.65 | 5.50 | 30.61 | 5.50 | 61.7 | 11.1 |
| Disodium EDTA Dihydrate | 0.14 | 0.10 | 0.56 | 0.10 | 0.56 | 0.1 |
| Sodium Citrate Dihydrate | 0.14 | 0.10 | 0.56 | 0.10 | 0.56 | 0.1 |
| Total (blend) | 139.10 | 100 | 556.60 | 100 | 557 | 100 |
| Size 0 White Capsule | — | — | 96.0 | — | 96.0 | — |
| Size 4 White Capsule | 38.0 | — | — | — | — | — |
| Total (drug product capsule) | 177.10 | — | 652.60 | — | 653 | — |

[1]"As is" basis, the compounding formula is based on obtaining 7.2 wt % based on free base content with a 72:28 ratio of Maisine to Gelucire

Example 8—Manufacturing of Capsules Containing the Compound (II) Formulation

This example describes an exemplary manufacturing process for capsules that contain a Compound (II) formulation that comprises Compound (II) hydrochloride, Maisine 35-1, Gelucire 44/14, sodium oleate, and EDTA.

The manufacturing process begins with melting Maisine 35-1. The liquid Maisine 35-1 is then added to a mixing kettle that has been heated to 40-45° C. The sodium oleate, pre-screened, is added, and the mixture is stirred at 40-45° C. for a minimum of 30 minutes. Disodium EDTA and sodium citrate are slowly added, and the mixture is stirred at 40-45° C. for a minimum of 30 minutes. Next, Compound (II) HCl is added, and the suspension is stirred at 40-45° C. for a minimum of 4 hours. Gelucire 44/14, which had also been pre-melted, is added to the mixture with stirring. The resultant blend is stirred for at least 20 minutes at 40-45° C. The formulation remains slightly turbid (presumed to be finely dispersed sodium chloride). The hot, bulk blend is transferred to the encapsulation hopper with in-line filtration. Standard white hard gelatin capsules are filled with the liquid blend at 40-45° C. The capsules are then banded using a gelatin/Polysorbate 80 banding solution, cooled to ambient temperature, and then dried for at least 12 hours. The bulk capsules are filled into HDPE bottles.

While the invention has been described with reference to exemplary embodiments, it is to be understood that the invention is not limited thereto.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A formulation comprising:

a compound having a structure:

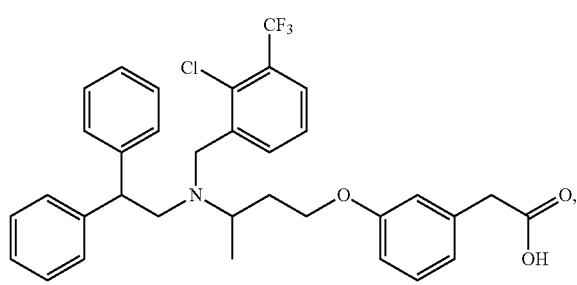 [SMILES: CC(CCOc1cccc(CC(=O)O)c1)N(Cc1cccc(C(F)(F)F)c1Cl)CC(c1ccccc1)c1ccccc1]

or a pharmaceutically acceptable salt thereof; and a lipophilic vehicle comprising at least one lipid excipient and at least one surfactant, wherein the compound, or the pharmaceutically acceptable salt thereof, is soluble in the lipophilic vehicle, wherein the lipophilic vehicle comprises at least two selected from the group consisting of PEG-200, PEG-300, PEG-400, a PEG castor oil, a lauroyl PEG glyceride, a stearoyl PEG glyceride, an oleoyl PEG glyceride, a caprylocapryl PEG glyceride, a PEG-20 glyceryl stearate, a glycerol oleate, a glycerol linoleate, a glycerol stearate, propylene glycol monocaprylate, polyglyceryl-3 dioleate, diethylene glycol monoethyl ether, d-alpha-tocopheryl polyethylene glycol 1000 succinate, polyoxyethylene (20) sorbitan monooleate, and polyoxyethylene (20) sorbitan monolaurate, and wherein the formulation is suitable for oral administration.

2. The formulation of claim 1, wherein a pH of the formulation is from about pH 4 to about pH 8.

3. The formulation of claim 1, wherein an amount of the compound, or the pharmaceutically acceptable salt thereof, in the formulation decreases by less than about 2% after storage for 6 months at a temperature of 40° C. and a relative humidity of 75%.

4. The formulation of claim 1, wherein the compound is a hydrochloride salt of:

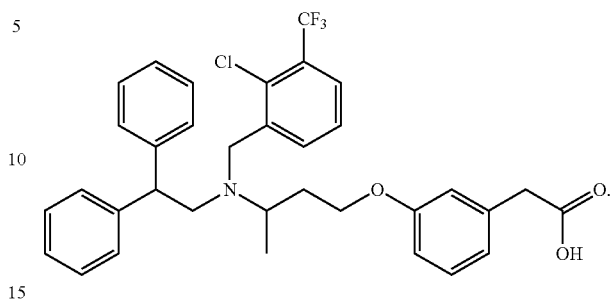

5. The formulation of claim 1, wherein the formulation is a semi-solid suspension.

6. The formulation of claim 1, wherein the formulation is self-emulsifying.

7. The formulation of claim 6, wherein the formulations has increased oral bioavailability in comparison to a formulation of the compound that is not self-emulsifying.

8. The formulation of claim 1, wherein the lipophilic vehicle comprises polyoxyethylene (20) sorbitan monooleate, the PEG castor oil, and a phosphatidylcholine.

9. The formulation of claim 1, wherein the lipophilic vehicle comprises the glycerol oleate, polyoxyethylene (20) sorbitan monooleate, the PEG castor oil, and a phosphatidylcholine.

10. The formulation of claim 8, further comprising an antioxidant.

11. The formulation of claim 10, wherein the antioxidant is butylated hydroxyanisole.

12. The formulation of claim 9, further comprising an antioxidant.

13. The formulation of claim 12, wherein the antioxidant is butylated hydroxyanisole.

14. The formulation of claim 8, wherein the PEG castor oil is PEG-35 castor oil.

15. The formulation of claim 9, wherein the PEG castor oil is PEG-35 castor oil.

16. The formulation of claim 10, wherein the PEG castor oil is PEG-35 castor oil.

17. The formulation of claim 11, wherein the PEG castor oil is PEG-35 castor oil.

18. The formulation of claim 12, wherein the PEG castor oil is PEG-35 castor oil.

19. The formulation of claim 13, wherein the PEG castor oil is PEG-35 castor oil.

20. The formulation of claim 1, wherein the glycerol linoleate is at least one of glyceryl monolinoleate, glyceryl dilinoleate, and glyceryl trilinoleate.

* * * * *